(12) United States Patent
Rowat et al.

(10) Patent No.: US 10,302,408 B2
(45) Date of Patent: May 28, 2019

(54) MECHANICAL PHENOTYPING OF SINGLE CELLS: HIGH THROUGHPUT QUANTITATIVE DETECTION AND SORTING

(71) Applicant: The Regents of the University of California, Oakland, CA (US)

(72) Inventors: Amy Rowat, Santa Monica, CA (US); David J. Hoelzle, South Bend, IN (US); Clara Chan, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/438,201

(22) PCT Filed: Nov. 5, 2013

(86) PCT No.: PCT/US2013/068571
§ 371 (c)(1),
(2) Date: Apr. 23, 2015

(87) PCT Pub. No.: WO2014/071398
PCT Pub. Date: May 8, 2014

(65) Prior Publication Data
US 2015/0268029 A1   Sep. 24, 2015

Related U.S. Application Data

(63) Continuation-in-part of application No. 13/802,684, filed on Mar. 13, 2013, now Pat. No. 9,423,234.
(Continued)

(51) Int. Cl.
*G01N 27/12* (2006.01)
*G01B 7/16* (2006.01)
(Continued)

(52) U.S. Cl.
CPC ............. *G01B 7/22* (2013.01); *B01L 3/5027* (2013.01); *C12M 47/04* (2013.01); *G01L 1/14* (2013.01);
(Continued)

(58) Field of Classification Search
USPC ................... 422/502, 503, 82.01, 98; 506/10
See application file for complete search history.

(56) References Cited

U.S. PATENT DOCUMENTS 3,845,386 A   10/1974   Davies et al.
4,284,500 A   8/1981    Keck
(Continued)

FOREIGN PATENT DOCUMENTS

CA   2257287 A1    12/1997
EP   1 249 261 A3  11/2002
(Continued)

OTHER PUBLICATIONS

William C. Tang, Dissertation: Electrostatic Comb Drive for Resonant Sensor and Actuator Applications, Nov. 1990.*
(Continued)

*Primary Examiner* — Dean Kwak
(74) *Attorney, Agent, or Firm* — Tom Hunter; Weaver Austin Villeneuve & Sampson LLP

(57) ABSTRACT

This invention provides methods and devices for the high-throughput characterization of the mechanical properties of cells or particles. In certain embodiments the devices comprise a micro fluidic channel comprising: an oscillating element on a first side of said channel; and a detecting element on a second side of said channel opposite said oscillating element, wherein said detecting element is configured to detect a force transmitted through a cell or microparticle by said oscillating element. In certain embodiments the devices comprise a microfluidic channel comprising an integrated oscillator and sensor element on one first side of said channel, wherein said sensor is configured to detect a force transmitted through a cell or microparticle by said oscillator.

15 Claims, 43 Drawing Sheets

Related U.S. Application Data

(60) Provisional application No. 61/722,689, filed on Nov. 5, 2012.

(51) Int. Cl.
| | | |
|---|---|---|
| *G01N 29/02* | (2006.01) | |
| *G01N 29/036* | (2006.01) | |
| *G01N 29/22* | (2006.01) | |
| *B01L 3/00* | (2006.01) | |
| *C12M 1/00* | (2006.01) | |
| *G01L 1/14* | (2006.01) | |
| *G01N 27/22* | (2006.01) | |

(52) U.S. Cl.
CPC ........... *G01N 27/22* (2013.01); *G01N 29/022* (2013.01); *G01N 29/036* (2013.01); *G01N 29/222* (2013.01); *B01L 2300/0663* (2013.01); *B01L 2300/0816* (2013.01); *B01L 2300/0877* (2013.01); *B01L 2400/0487* (2013.01); *G01N 2291/02466* (2013.01); *G01N 2291/02827* (2013.01)

(56) References Cited

U.S. PATENT DOCUMENTS

| | | | |
|---|---|---|---|
| 4,374,488 A | 2/1983 | Peterson | |
| 4,734,192 A | 3/1988 | Champion et al. | |
| 4,902,481 A | 2/1990 | Clark et al. | |
| 5,486,457 A | 1/1996 | Butler et al. | |
| 5,579,107 A | 11/1996 | Wright et al. | |
| 5,589,589 A | 12/1996 | Sponheimer et al. | |
| 6,030,531 A | 2/2000 | Gershenson | |
| 6,103,479 A | 8/2000 | Taylor | |
| 6,192,768 B1 * | 2/2001 | Wallman | B01F 15/0241 |
| | | | 73/863 |
| 6,565,813 B1 | 5/2003 | Garyantes | |
| 6,696,240 B1 | 2/2004 | Kloepfer et al. | |
| 6,864,100 B1 | 3/2005 | Ribbe et al. | |
| 7,022,528 B2 | 4/2006 | Avdeef et al. | |
| 7,094,346 B2 | 8/2006 | Osenar et al. | |
| 7,297,269 B2 | 11/2007 | Osenar et al. | |
| 7,393,269 B2 | 7/2008 | Rambosek et al. | |
| 7,629,115 B2 | 12/2009 | Gu et al. | |
| 7,846,389 B2 | 12/2010 | Owen et al. | |
| 7,846,743 B2 | 12/2010 | Tai et al. | |
| 8,501,117 B1 * | 8/2013 | Bedair | G01N 5/02 |
| | | | 422/500 |
| 9,423,234 B2 | 8/2016 | Rowat et al. | |
| 2002/0027100 A1 | 3/2002 | Gershenson | |
| 2002/0094533 A1 | 7/2002 | Hess et al. | |
| 2003/0012692 A1 | 1/2003 | Lemee et al. | |
| 2003/0038091 A1 | 2/2003 | Gershenson | |
| 2003/0038092 A1 | 2/2003 | Gershenson | |
| 2003/0104512 A1 | 6/2003 | Freeman et al. | |
| 2003/0124716 A1 | 7/2003 | Hess et al. | |
| 2003/0180807 A1 | 9/2003 | Hess et al. | |
| 2004/0018615 A1 | 1/2004 | Garyantes | |
| 2004/0069714 A1 | 4/2004 | Ferguson | |
| 2004/0096622 A1 | 5/2004 | Razavi et al. | |
| 2005/0214737 A1 | 9/2005 | Dejneka et al. | |
| 2006/0057559 A1 | 3/2006 | Xu et al. | |
| 2006/0141539 A1 | 6/2006 | Taylor | |
| 2006/0194307 A1 | 8/2006 | Yasuda et al. | |
| 2007/0107495 A1 | 5/2007 | Kim et al. | |
| 2007/0190653 A1 | 8/2007 | Heinrich | |
| 2007/0243523 A1 | 10/2007 | Ionescu-Zanetti et al. | |
| 2007/0289917 A1 | 12/2007 | Mylin et al. | |
| 2008/0110247 A1 | 5/2008 | Shaw et al. | |
| 2008/0233850 A1 | 9/2008 | Woo et al. | |
| 2009/0018668 A1 | 1/2009 | Galbraith | |
| 2009/0280518 A1 | 11/2009 | Adamo et al. | |
| 2009/0298191 A1 | 12/2009 | Whitesides et al. | |
| 2009/0306364 A1 | 12/2009 | Beer et al. | |
| 2009/0311738 A1 | 12/2009 | Kuiper et al. | |
| 2010/0321045 A1 | 12/2010 | Ku et al. | |
| 2011/0053152 A1 | 3/2011 | Goldkorn et al. | |
| 2011/0097571 A1 | 4/2011 | Tee et al. | |
| 2011/0111412 A1 | 5/2011 | Tai et al. | |
| 2011/0124095 A1 | 5/2011 | Manalis et al. | |
| 2012/0329141 A1 * | 12/2012 | Cho | B01L 3/502746 |
| | | | 435/287.1 |
| 2014/0087412 A1 * | 3/2014 | Fouras | B01L 3/502761 |
| | | | 435/29 |
| 2014/0128285 A1 | 5/2014 | Rowat et al. | |
| 2014/0235500 A1 | 8/2014 | Rowat et al. | |

FOREIGN PATENT DOCUMENTS

| | | |
|---|---|---|
| EP | 1 677 094 A2 | 7/2006 |
| EP | 0 912 892 B1 | 9/2008 |
| EP | 2 107 120 A1 | 10/2009 |
| EP | 2 199 384 A1 | 6/2010 |
| EP | 1 973 635 B1 | 6/2011 |
| EP | 2 420 824 A2 | 2/2012 |
| GB | 2 337 261 A | 11/1999 |
| JP | 02-087042 A2 | 3/1990 |
| KR | 20-2009-0005164 U | 5/2009 |
| WO | WO 90/00922 A1 | 2/1990 |
| WO | WO 90/07545 A2 | 7/1990 |
| WO | WO 90/07575 A1 | 7/1990 |
| WO | WO 92/06774 A1 | 4/1992 |
| WO | WO 92/07243 A1 | 4/1992 |
| WO | WO 95/11736 A1 | 5/1995 |
| WO | WO 97/08306 A1 | 3/1997 |
| WO | WO 97/45730 A1 | 12/1997 |
| WO | WO 99/39829 A1 | 8/1999 |
| WO | WO 99/45035 A1 | 9/1999 |
| WO | WO 99/45036 A1 | 9/1999 |
| WO | WO 99/67639 A1 | 12/1999 |
| WO | WO 00/17624 A2 | 3/2000 |
| WO | WO 00/25922 A2 | 5/2000 |
| WO | WO 01/39858 A1 | 6/2001 |
| WO | WO 02/30561 A2 | 4/2002 |
| WO | WO 02/094414 A1 | 11/2002 |
| WO | WO 03/080226 A1 | 10/2003 |
| WO | WO 2004/009840 A1 | 1/2004 |
| WO | WO 2004/034036 A2 | 4/2004 |
| WO | WO 2005/081722 A2 | 9/2005 |
| WO | WO 2005/102528 A1 | 11/2005 |
| WO | WO 2006/124318 A2 | 11/2006 |
| WO | WO 2006/124318 A3 | 11/2006 |
| WO | WO 2007/022026 A2 | 2/2007 |
| WO | WO 2007/037903 A2 | 4/2007 |
| WO | WO 2007/060580 A1 | 5/2007 |
| WO | WO 2007/117987 A2 | 10/2007 |
| WO | WO 2007/136472 A1 | 11/2007 |
| WO | WO 2008/035159 A2 | 3/2008 |
| WO | WO 2008/049083 A2 | 4/2008 |
| WO | WO 2008/061317 A1 | 5/2008 |
| WO | WO 2008/115628 A1 | 9/2008 |
| WO | WO 2008/115663 A1 | 9/2008 |
| WO | WO 2008/157257 A1 | 12/2008 |
| WO | WO 2009/157627 A1 | 12/2009 |
| WO | WO 2010/010355 A2 | 1/2010 |
| WO | WO 2010/045389 A1 | 4/2010 |
| WO | WO 2010/124001 A1 | 10/2010 |
| WO | WO 2010/132890 A1 | 11/2010 |
| WO | WO 2010/135603 A2 | 11/2010 |
| WO | WO 2011/021984 A1 | 2/2011 |
| WO | WO 2011/119492 A2 | 9/2011 |
| WO | WO 2011/163058 A2 | 12/2011 |
| WO | WO 2013/056253 A1 | 4/2013 |
| WO | WO 2014/071398 A1 | 5/2014 |

OTHER PUBLICATIONS

U.S. Office Action dated May 5, 2016 issued in U.S. Appl. No. 14/351,115.
U.S. Office Action dated Aug. 1, 2014 issued in U.S. Appl. No. 13/802,684.
U.S. Final Office Action dated Dec. 10, 2015 issued in U.S. Appl. No. 13/802,684.

(56) References Cited

OTHER PUBLICATIONS

U.S. Notice of Allowance dated Apr. 19, 2016 issued in U.S. Appl. No. 13/802,684.
PCT International Search Report and Written Opinion dated Mar. 28, 2013 issued in PCT/US2012/060297.
PCT International Preliminary Report on Patentability and Written Opinion dated Apr. 24, 2014 issued in PCT/US2012/060297.
PCT International Search Report and Written Opinion dated Feb. 26, 2014 issued in PCT/US2013/068571.
PCT International Preliminary Search Report and Written Opinion dated May 14, 2015 issued in PCT/US2013/068571.
Chinese Office Action [Description in English] dated May 23, 2016 issued in Application No. CN 201380069416.2.
Bayraktar et al. (Jan. 23-27, 2011) "A MEMS Based Gravimetric Resonator for Mass Sensing Applications," *IEEE MEMS*, pp. 817-820.
Bernabini et al. (2011) "Micro-impedance cytometry for detection and analysis of micron-sized particles and bacteria," *Lab Chip*, 11:407-412.
Bow et al. (2011) "A Microfabricated Deformability-Based Flow Cytometer with Application to Malaria," *Lab on a Chip*,11:1065-1073.
Calbo et al. (2011) "A Functional Role for Tumor Cell Heterogeneity in a Mouse Model of Small Cell Lung Cancer," *Cancer Cell*, 19(2):244-256.
Chen et al. (2011) "Classification of cell types using a microfluidic device for mechanical and electrical measurement of single cells," *Lab on a Chip*,11:3174-3181.
Cheng et al. (2007) "Cell detection and counting through cell lysate impedance spectroscopy in microfluidic devices," *Lab on a Chip*, 7:746-755.
Cross et al. (2007) "Nanomechanical analysis of cells from cancer patients," *Nature Nanotechnology*, 2:780-783.
Eroglu et al. (Jun. 5-9, 2011) "A Laterally Resonating Gravimetric Sensor With Uniform Mass Sensitivity and High Linearity," *IEEE Transducers' 11*, Beijing, China. pp. 2255-2258.
Fabry et al. (1999) "Implications of heterogeneous bead behavior on cell mechanical properties measured with Magnetic Twisting Cytometry," *Journal of Magnetism and Magnetic Materials*, 194:120-125.
Gossett et al. (2012) "Hydrodynamic stretching of single cells for large population mechanical phenotyping," *Proc. Natl. Acad. Sci. USA* 109(20):7630-7635.
Green et al. (2010) "An Integrated Instrument for Rapidly Deforming Living Cells Using Rapid Pressure Pulses and Simultaneously Monitoring Applied Strain in Near Real Time," *Review of Scientific Instruments*, 81(12):125102, 6pp.
Guck et al. (2000) "Optical deformability of soft biological dielectrics," *Physical Review Letters*, 84:5451-5454.
Higgins et al. (Dec. 18, 2007) "Sickle cell vasoocclusion and rescue in a microfluidic device," *Proc Natl Acad Sci, USA* 104:20496-500.
Hur et al. (2011) "Deformability-based cell classification and enrichment using inertial microfluidics," *Lab on a Chip*, 11:912-920.
Ilic et al. (Nov./Dec. 2001) "Single cell detection with micromechanical oscillators," *Journal of Vacuum Science & Technology B*, 19(6):2825-2828.
Kasza et al. (2007) "The cell as a material," *Curr. Opin. Cell Biol.*, 19:101-107.
Khine et al. (2005) "A single cell electroporation chip," *Lab on a Chip*, 5:38-43.
Lam et al. (2007) "Chemotherapy exposure increases leukemia cell stiffness," *Blood*, 109:3505-35088.

Liu et al. (2007) "Real-time high-accuracy micropipette aspiration for characterizing mechanical properties of biological cells," *IEEE International Conference on Robotics and Automation*, Roma, Italy, pp. 1930-1935.
Mukundan et al. (2009) "MEMS Electrostatic Actuation in Conducting Biological Media," *Journal of Microelectricalmechanical Systems*, 18:405-413 [NIH Public Access Author Manuscript—21pp].
Mukundan et al. (2009) "Modeling and Characterization of Electrostatic Comb-Drive Actuators in Conducting Liquid Media," *Journal of Micromechanics and Microengineering*, 19:065008 (9pp).
Paj erowski et al. (2007) "Physical plasticity of the nucleus in stem cell differentiation," *Proc Natl Acad Sci, USA* 104:15619-15624.
Qi et al. (2012) "Probing single cells using flow in microfluidic devices," *The European Physical Journal Special Topics*, 204(1):85-101.
Raafat, Mohamed Salem (2010) "Self-Sorting of Deformable Particles in a Microfluidic Circuit," *Thesis (S.M.)—Massachusetts Institute of Technology, Dept. of Mechanical Engineering*, 57 pages.
Rogers et al. (2005) "Recent progress in soft lithography," *Materials Today*, 8:50-56.
Schoenwald et al. (2010) "Integration of atomic force microscopy and a microfluidic liquid cell for acqueous imaging and force spectroscopy," *Review of Scientific Instruments*, 81(5):053704(6pp).
Secomb et al. (Aug.1996) "Analysis of Red Blood Cell Motion through Cylindrical Micropores: Effects of Cell Properties," *Biophys Journal*, 71(2):1095-1101.
Seiffert et al. (2010) "Controlled fabrication of polymer microgels by polymer-analogous gelation in droplet microfluidics," *Soft Matter*, 6:3184-3190.
Sraj et al. (2010) "Cell deformation cytometry using diode-bar optical stretchers," *Journal of Biomedical Optics*, 15(4):047010(1-7).
Suresh (Jul. 2007) "Biomechanics and biophysics of cancer cells," *Acta Biomaterialia*, 3:413-438.
Swaminathan et al. (2011) "Mechanical stiffness grades metastatic potential in patient tumor cells and in cancer cell lines," *Cancer Research*, 71(15):5075-5080 [in press 2012].
Thoumine et al. (1999) "Microplates: A new tool for manipulation and mechanical pertubation of individual cells," *Journal of Biochemical and Biophysical Methods*, 39:47-62.
Tseng et al. (2002) "Micromechanical mapping of live cells by multiple-particle-tracking microrheology," *Biophysical Journal*, 83:3162-3176.
Vanapalli et al. (Jan. 5, 2009) "Microfluidics as a functional tool for cell mechanics," *Biomicrofluidics, American Institute of Physics*, 3(1):012006, pp. 1-15.
Waggoner et al. (2007) "Micro- and nanomechanical sensors for environmental chemical, and biological detection," *Lab on a Chip*, 7(10):1238-1255.
Zhang et al. (2002) "Effect of cubic nonlinearity on autoparametrically amplified resonant MEMS mass sensor," *Sensors and Actuators A*, 102(1-2):139-150.
Zhang et al. (2005) "Application of parametric resonance amplification in a single-crystal silicon micro-oscillator based mass sensor," *Sensors and Actuators A*, 122(1):23-30.
U.S. Final Office Action dated Feb. 8, 2017 issued in U.S. Appl. No. 14/351,115.
U.S. Office Action dated Oct. 5, 2017 issued in U.S. Appl. No. 14/351,115.
U.S. Final Office Action dated Jul. 27, 2018 issued in U.S. Appl. No. 14/351,115.
Chinese Office Action [Description in English] dated Mar. 15, 2017 issued in Application No. CN 201380069416.2.
Chinese Office Action [Description in English] dated Sep. 26, 2017 issued in Application No. CN 201380069416.2.

* cited by examiner

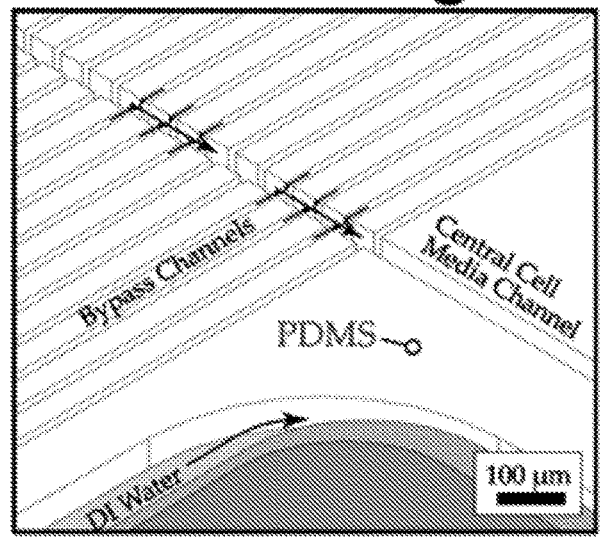
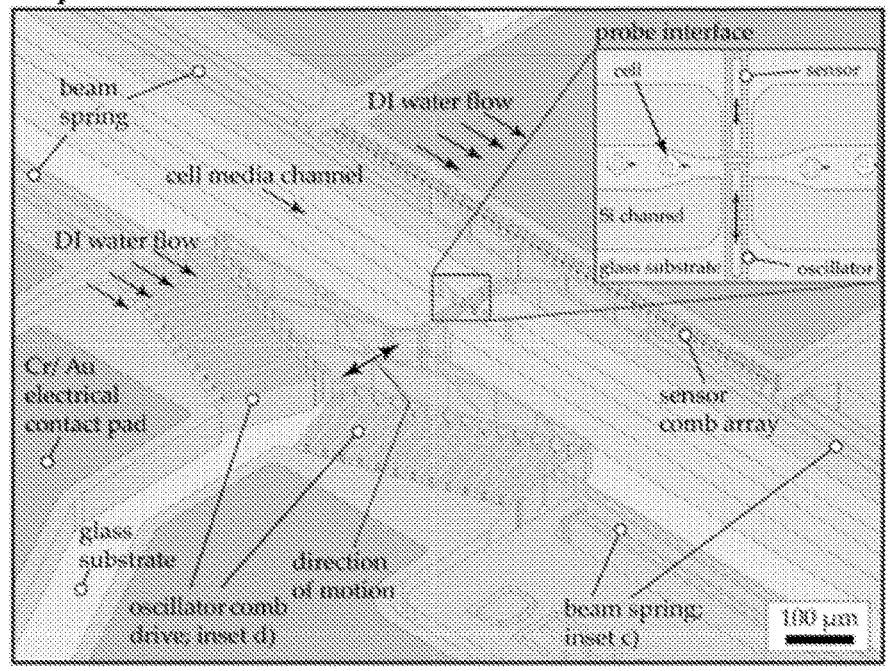
*Fig. 8, cont'd.*

D) Beam Spring System
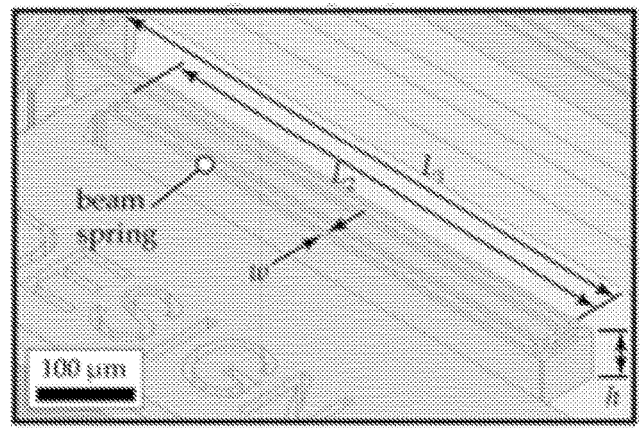
E) Oscillator Comb Drive
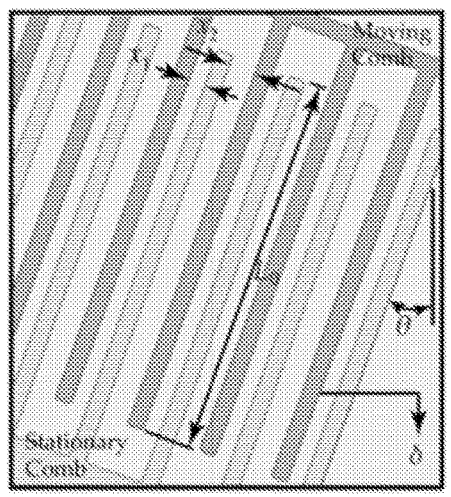
*Fig. 8, cont'd.*

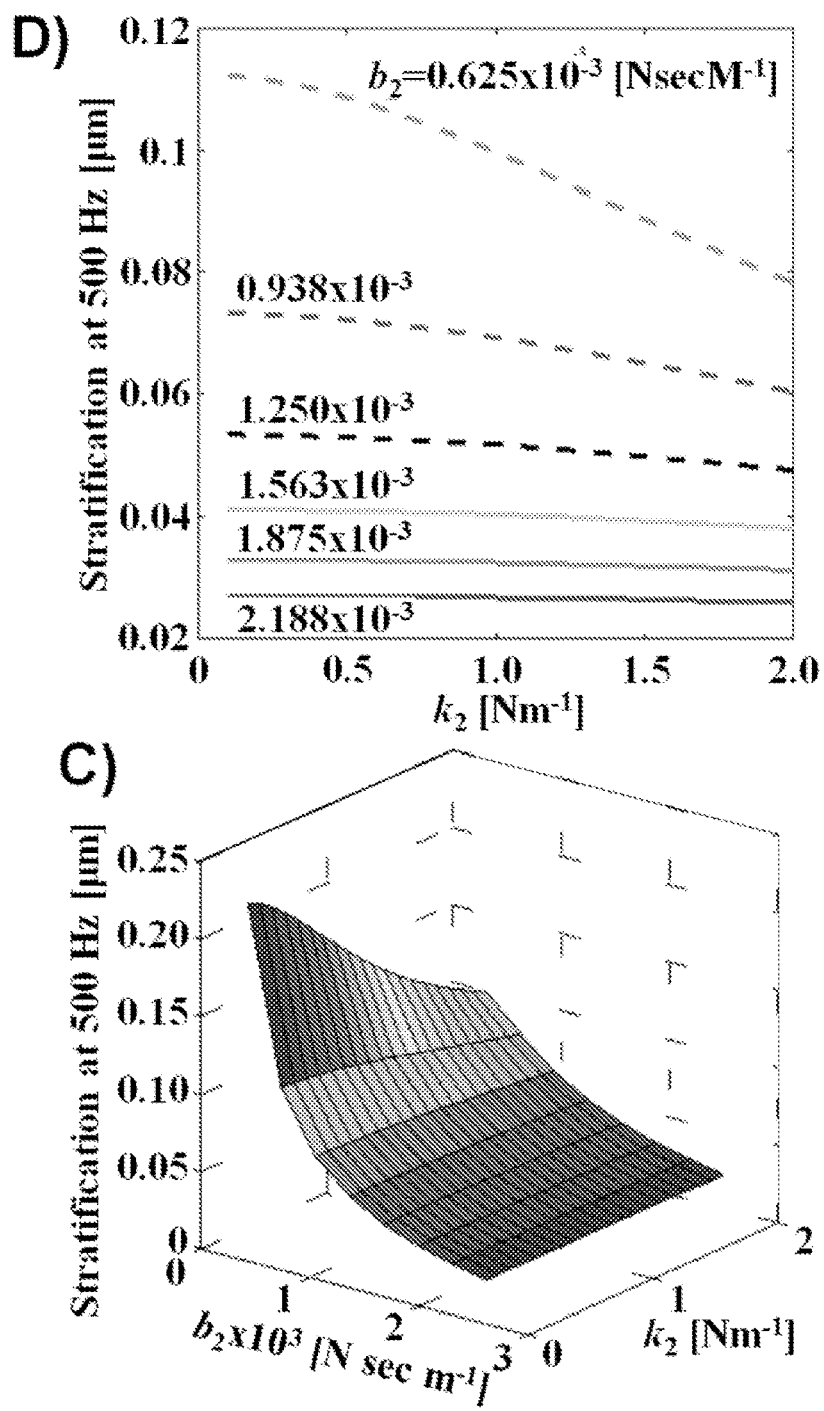
Fig. 10, cont'd.

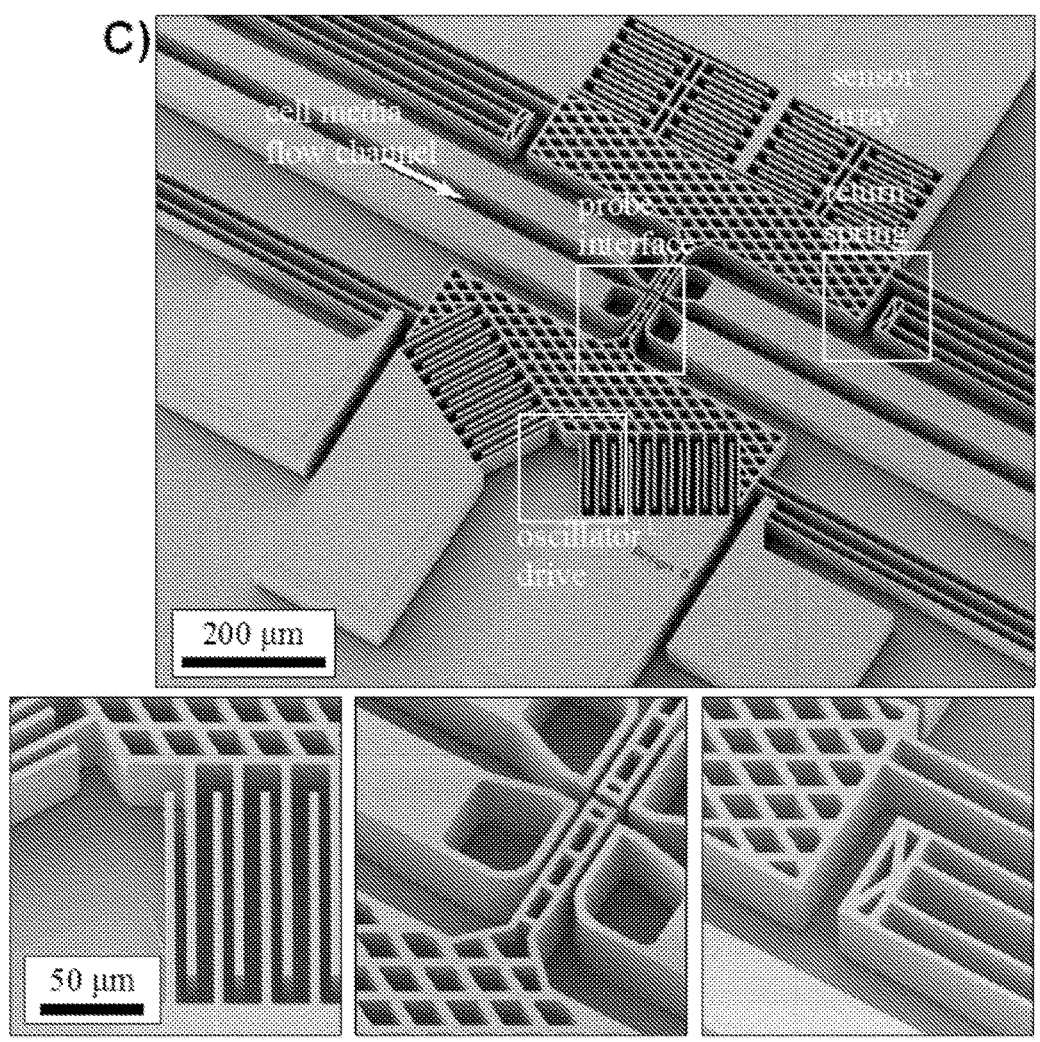
*Fig. 14, cont'd.*

*Fig. 33, cont'd.*

MECHANICAL PHENOTYPING OF SINGLE CELLS: HIGH THROUGHPUT QUANTITATIVE DETECTION AND SORTING

CROSS-REFERENCE TO RELATED APPLICATIONS

This application is a U.S. 371 National Phase of PCT/US2013/068571, filed on Nov. 5, 2013, which is a continuation-in-part of U.S. Ser. No. 13/802,684, filed on Mar. 13, 2013, which claims priority to U.S. Ser. No. 61/722,689, filed on Nov. 5, 2012, all of which are incorporated herein by reference in their entirety for all purposes.

STATEMENT OF GOVERNMENTAL SUPPORT

[Not Applicable]

BACKGROUND

Cells are soft, viscoelastic materials whose main structural components are proteins and membranes and whose mechanical phenotype can be significantly altered during pathological transformations. For example, during neoplastic progression, cytoskeletal reorganization results in a measurable decrease in the cell's mechanical modulus (Suresh (2007) *Acta Biomaterialia,* 3: 413-438; Cross, et al. (2007) *Nat. Nanotechnol.,* 2: 780-783), more commonly known as stiffness. Drug treatment can also result in an altered cellular mechanical phenotype: human leukemia cells treated with certain chemotherapy drugs exhibit an increased modulus (Lam, et al. (2007) *Blood,* 109: 3505-3508). Preliminary results from our laboratory also show that we can detect mechanical transformations of ovarian cancer cells after treatment with microRNA that reverts the cancerous phenotype towards a healthy phenotype, as evaluated by conventional proliferation and apoptosis assays; treated cells are less deformable than base ovarian cancer cells by a statistically significant margin. Thus, a promising fresh perspective for evaluating cancer treatment is to exploit the mechanical signature of cells.

Yet to fully exploit mechanical profiling of cells (e.g., for cancer or other applications) is believed desirable to quantitatively measuring large number of cells (e.g., $>10^2$, or $>10^3$, or $>10^4$, or $>10^5$ cells within a day) for statistically significant analysis of cell subpopulations. It is believed this generally requires processing a large number of cells with a throughput that no previous methodology can offer. Current methods for mechanical phenotyping, such as Atomic Force Microscopy (AFM), provide detailed and accurate cell modulus measurements of a small subset of an entire cell population. However, due to slow detection speeds, sample size is typically limited to less than 100 cells/day using current systems that provide quantitative data (see, e.g., FIG. 1). By contrast, a common and powerful technique for cell characterization, Fluorescence Activated Cell Sorting (FACS), operates at detection rates on the order of $10^4$ cells per second and provides population statistics for levels of specific proteins that are assessed by fluorescent markers.

SUMMARY

Devices and methods are provided herein that permit rapid quantitative screening of large numbers of cells based on various mechanical (or other) parameters (e.g., elastic modulus, shear stiffness, viscosity, relaxation after deformation, various electrical properties, and the like). In certain embodiments the instruments and methods facilitate identification of compounds that induce cell death or revert a cell's metastatic phenotype. In certain embodiments the instruments and methods to identify treatments that target subpopulations of cells, including those that are premalignant, drug-resistant, or may cause cancer recurrence are provided.

In certain embodiments a device for the mechanical characterization of cells or microparticles, microorganisms, or organelles is provided where the device comprises a microfluidic channel comprising: an oscillating element on a first side of the channel; and a detecting element on a second side of the channel opposite the oscillating element, wherein the detecting element is configured to detect a force transmitted through a cell or microparticle by the oscillating element. In certain embodiments a device for the mechanical characterization of cells or microparticles is provided where the device comprises a microfluidic channel comprising: an integrated oscillator and sensor element on one first side of the channel, wherein the sensor is configured to detect a force transmitted through a cell or microparticle by the oscillator. In certain embodiments, the oscillating element oscillates at a frequency ranging from about 5 Hz, or from about 20 Hz, or from about 15 Hz, or from about 20 Hz, or from about 30 Hz, or from about 40 Hz, or from about 50 Hz, or from about 60 Hz or from about 80 Hz, or from about 100 Hz, or from about 200 Hz, or from about 300 Hz, or from about 400 Hz, or from about 500 Hz up to about 4 kHz or up to about 3 kHz, or up to about 2 kHz, or up to about 1 kHz. In certain embodiments, the oscillating element oscillates at a frequency ranging from about 5 Hz, or from about 20 Hz, or from about 15 Hz, or from about 20 Hz, or from about 30 Hz, or from about 40 Hz, or from about 50 Hz, or from about 60 Hz or from about 80 Hz, up to about 100 Hz, or up to about 150 Hz, or up to about 200 Hz, or up to about 250 Hz, or up to about 300 Hz, or up to about 350 Hz, or up to about 400 Hz, or up to about 450 Hz, or up to about 500 Hz. In certain embodiments, the oscillating element oscillates at a frequency ranging from about 200 Hz up to about 600 Hz. In certain embodiments, the oscillating element oscillates at a frequency of about 400 Hz. In certain embodiments, the width of the channel is sufficient to pass a single cell (e.g., a single cell at a time). In certain embodiments, the width of the channel is sufficient to pass a micron-scale hydrogel or small organism (e.g., *C. elegans,* bacteria, etc.). In certain embodiments, the width of the channel ranges from about 1 μm, or from about 5 μm, or from about 10 μm up to about 300 μm, or up to about 200 μm, or up to about 100 μm, or up to about 90 μm, or up to about 80 μm, or up to about 70 μm, or up to about 60 μm, or up to about 50 μm. In certain embodiments, the width of the channel ranges from about 5 μM to about 100 μm. In certain embodiments, the width of the channel ranges from about 5 μM to about 70 μm. In certain embodiments, the oscillating element comprises a comb drive. In certain embodiments, the detecting element comprises a comb. In certain embodiments, the oscillating element is configured to oscillate in response to a varying potential. In certain embodiments, the detecting element is configured to detect displacement of comb fingers by detecting changes in comb capacitance. In certain embodiments, the comb comprising the oscillating element and/or the comb comprising the detecting element further comprise beam springs that return comb fingers to a neutral position. In certain embodiments, the device comprises a second channel or fluid line that carries deionized and/or distilled water across the combs and/or associated electronics. In certain embodiments, the device comprises a second channel or fluid line that carries a fluid (e.g., an oil) with a lower dielectric constant than the fluid in the first channel. In certain embodiments, the device comprises a fabricated block within which is formed, embedded or molded the channel. In certain embodiments the block material from which the device is fabricated is selected from the group consisting of polydimethylsiloxane (PDMS), polyolefin plastomer (POP), perfluoropolyethylene (PFPE), polyurethane, polyimides, and cross-linked NOVOLAC® (phenol formaldehyde polymer) resins, borosilicate glass, SF11 glass, SF12 glass, polystyrene, Pyrex 7740, PMMA, and polycarbonate. In certain embodiments the device or system containing said device comprising a pump or pressure system to move cells and/or reagents through or into the microchannels and/or the microcavities.

In certain embodiments methods method of mechanically characterizing a cell, a particle, a microorganism, or an organelle are provided where the methods comprise: passing the cell, particle, microorganism, or organelle through the microfluidic channel of a device as described and/or claimed herein; operating the oscillating element to apply a force to the cell, particle, microorganism, or organelle; and detecting capacitance changes in the detecting element to provide a measure of the response of cell, particle, microorganism, or organelle to the force wherein the response provides a measure of the mechanical properties of the cell, particle, microorganism, or organelle. In certain embodiments the device is operated with a fundamental frequency of about 400 Hz and a carrier frequency of about 0.5 MHz.

In certain embodiments, the cell (or particle) response to force can be monitored by high speed imaging to detect the contour of the cell (or particle) and relaxation behavior.

Definitions

The term comb-drives refers to actuators (e.g., capacitive actuators), often used as linear actuators that utilize electrostatic forces that act between two electrically conductive combs. Comb drive actuators typically operate at the micro- or nanometer scale and are generally manufactured by bulk micromachining or surface micromachining a silicon wafer substrate. Attractive electrostatic forces are created when a voltage is applied between the static and moving combs causing them to be drawn together. In a longitudinal design (e.g., 0° orientation as described herein), the capacitance changes linearly with comb displacement, but force is a function of voltage. In latitudinal designs (e.g., 90° orientation as described herein), the force has a cubic relationship with displacement and an inversely proportional relationship between capacitance and displacement. Hybrid designs, like the 20° hybrid design described herein here, have a more complex relationship. The combs are typically arranged so that they never touch (because then there would be no voltage difference). Typically the teeth are arranged so that they can slide past one another until each tooth occupies the slot in the opposite comb. In certain embodiments restoring springs, levers, and crankshafts can be added to provide a restoring force, and/or if the comb drive's linear operation is to be converted to rotation or other motions

BRIEF DESCRIPTION OF THE DRAWINGS

FIG. 15A: Etch mask for Design 1. FIG. 15B: Etch mask for Design 3.

FIG. 16A: Masked region from FIG. 15 defines the non-etched region. FIG. 16B: Etched regions are ~42 micron lower than the masked regions; assessed by profilometry of representative features. In the actual fabrication protocol, a thin (50 μm thick) Si wafer adhered to glass is etched through. A wet etch release releases moving members from the glass, permitting MEMS device movement.

FIG. 20A: Study of all comb angles 0-90°. The jagged edge is where the maximum displacement is reached. FIG. 20B: Level sets for the 0°, 30°, and 90° designs.

FIG. 24B is a zoomed in portion of FIG. 24A. Driving signal will have a first harmonic frequency at approximately 400 Hz and a second harmonic from the carrier frequency at 0.5 MHz, off plot, and will be significantly attenuated.

FIG. 36A) There is an approximate inverse relationship between the damping coefficient, ζ, and nondimensional bandwidth, $$\frac{\omega_{BW}}{\omega_n}.$$

The plot is recast as a log-log plot to demonstrate the two operable ranges. Oscillators in air or vacuum operate well within the underdamped region where $\zeta<10^{-1}$ and bandwidth is largely insensitive to $\zeta$. Underwater oscillators operate in the $\zeta\in(5, 15)$ range where $\zeta$ deleteriously affects the operable frequency range. FIG. 36B) There is an approximate linear relationship between spring constant and bandwidth. Viscous damping changes the slope of the linear relationship. Logically a larger bandwidth is more readily achieved when the damping is minimal. The design detailed in the Examples has a damping of $b\sim1.25\times10^{-3}$ μN sec μm$^{-1}$.

FIG. 37A) Demonstration of equilibria of (6) for a design in which k~10 μN μm$^{-1}$ and $\theta=20°$. Spring force scales approximately linearly with displacement while electrostatic force, $F(x, \overline{V})$ scales as a cubic polynomial. For $\overline{V}<V_{max}$ there are two equilibria, one stable and one unstable. As the voltage is increased towards $V_{max}$, the two equilibria converge to a single displacement, $x_{max}$, which is the theoretical maximum static displacement for a given design. FIG. 37B) There is an optimal $\theta_{max}$ that maximizes the displacement $x_{max}$ for any given k. As the spring constant increases, the comb drive must generate a larger force within the constraint of $\overline{V}\in(0V, 8V)$ and therefore $\theta$ must be larger.

FIG. 39A) Oscillator response to an applied voltage $V(t)=½\overline{V}(1+\cos \omega t)$ at varying frequencies $\omega$. The time axis is normalized by frequency. FIG. 39B) Maximum displacement and phase shift of an underwater oscillator as a function of frequency. The standard definitions of magnitude and frequency do not apply for non-linear system; here we utilize maximum displacement and normalized time-shift ($x_{max}(\omega)$ and $\theta(\omega)$) from FIG. 39A. FIG. 39C) A large displacement may be maintained across a large frequency range by modulating $\overline{V}$ at high frequencies. We demonstrate a particular underwater oscillator design that can achieve large displacements (>9 μm) at high-frequencies (>1 kHz).

FIG. 40A) Achievable $x_{max}$ displacements for a given k and actuation frequency ω. FIG. 40B) Optimal drive angle $\theta_{max}$ for a given k and actuation frequency ω.

DETAILED DESCRIPTION

Figure 1:
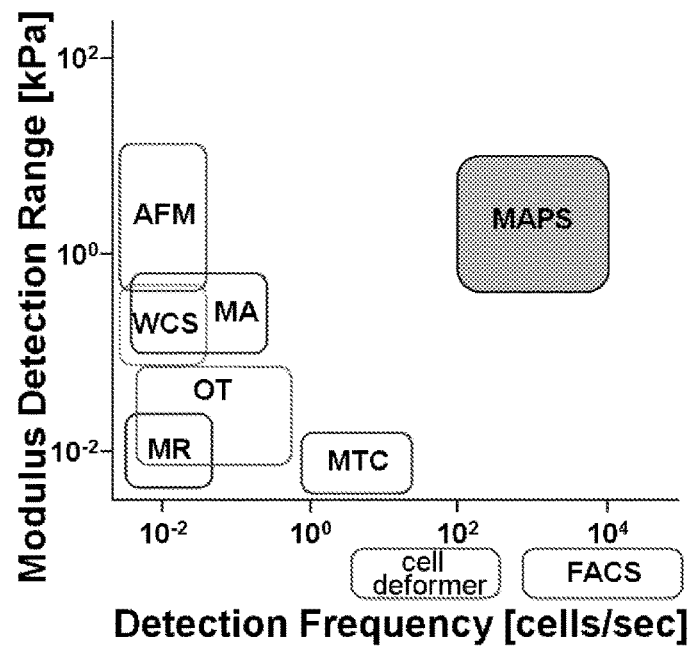
FIG. 1 illustrates detection frequency and modulus detection range for the systems described herein as compared to other mechanical measurement systems. As illustrated in this Figure, the MaPS system(s) described herein markedly advance detection frequency and therefore will be capable of efficiently screening large drug libraries and enable cell sorting based on the mechanical phenotype. Key: Atomic Force Microscopy (AFM) (Cross, et al. (2007) Nat. Nanotechnol., 2: 780-783), Whole Cell Stretching (WCS) (Thoumine, et al., (1999) J. Biochem. Biophys. Meth., 39: 47-62), Micropipette Aspiration (MA) (Liu, et al. (2007) In IEEE International Conference on Robotics and Automation, Roma, Italy, pp. 1930-1935), Microrheology (MR) (Lam, et al. (2007) Blood, 109: 3505-3508; Tseng et al. (2002) Biophys. J. 83: 3162-3176), Optical Tweezers (OT) (Sraj et al. (2010) J. Biomed. Optics, 15: 047010; Guck, et al. (2000) Phys. Rev. Letts. 84: 5451-5454), and Magnetic Twisting Cytometry (MTC) Fabry et al. (1999) J. Magnetism Magnetic Mat. 194: 120-125. The Cell Deformer and FACS do not measure the cell modulus, but are shown off-plot for comparison.

To bring unprecedented detection speeds and comprehensive population statistics to the mechanical phenotyping of individual cells within a large population, a Mechanical Profiling and Sorting (MaPS) platform is provided. This microfluidic platform has probe-based detection for rapid measurement of cells under flow. In certain embodiments the MaPS integrates a microfluidic network with an in situ mechanical probe and sensor for direct measurement of the elastic modulus of individual cells. Whereas other mechanical phenotyping devices require computationally intensive image analysis, cellular adhesion to a substrate, or merely provide qualitative, comparative "deformability" data, the MaPS device described herein is a plug-and-play device with a quantitative readout that requires no fluorescent labeling. MaPS thus has great potential to quantitatively determine the efficacy of cancer treatment at the level of individual cells. Importantly, MaPS can be adapted to investigate other physical attributes of cells, such as their electrical properties or relaxation behavior in response to an imposed deformation.

In certain embodiments the detection mechanisms in the MaPS devices described herein are based on analog signal processing and are therefore very fast. An active sorting mechanism can be directly integrated into the device to quickly sort a cell into one of multiple sub-populations by making a decision based on the deformability/modulus of the cell and then quickly activating the sorter appropriately. Beyond screening chemotherapy drug libraries, recent results suggest that cell deformability/elastic modulus can be used to grade the metastatic potential of ovarian cancer cell lines (Xu et al. (2012) *PLoS ONE* 7(10): e46609; Swaminathan et al. (2012) *Cancer Res.* 71(15): 5075-5080). Softer malignant cells are more invasive as compared to stiffer malignant cells (Id.). Without being bound to a particular theory, it is believed that these findings have direct functional implications since softer cells can more easily transit through tortuous vascular and lymphatic networks to seed at a secondary site.

Invasion assays typically require at least several hours for cells to traverse the filter and for subsequent evaluation by microscopy. By contrast, to evaluate the same sample volume using the MaPS devices described herein requires mere minutes. MaPS is also uniquely capable of assessing heterogeneity in the mechanical properties of individual cancer cells within a neoplasm. Such phenotypic diversity can provide prognostic insight (Calbo, et al. (2011) *Cancer Cell*, 19: 244-256). Furthermore, there has been shown to be a distinct mechanical signature for pathologies such as malaria (Bow, et al. (2011) *Lab on a Chip*, 11: 1065-1073) and sickle cell anemia (Higgins, et al. (2007) *Proc. Natl. Acad. Sci. USA*, 104: 20496-20500). Stem cells also undergo significant changes in their molecular composition during differentiation and these changes are measurable through their mechanical properties (Pajerowski et al. (2007) *Proc. Natl. Acad. Sci. USA*, 104: 15619-15624). There is great promise that the MaPS described useful in the diagnosis and assessment of these pathological and physiological transformations as well.

Mechanical Phenotyping with High Throughput.

In various embodiments the MaPS systems described herein permit mechanical phenotyping at a rate of greater than about 10$^2$ cells per second, or greater than about 10$^3$ cells per second, or greater than about 10$^4$ cells per second. The throughput can be scaled up, for example by using multiple channels, and it is believed that capacities of greater than about 10$^5$ cells per second, or greater than about 10$^6$ cells per second, or greater than about 10$^7$ cells per second, greater than about 10$^8$ cells per second are achievable. This facilitates the rapid and effective evaluation of the extent to which the mechanical phenotype is a marker for the physiological and pathological state of cells in various contexts.

Figure 2A:
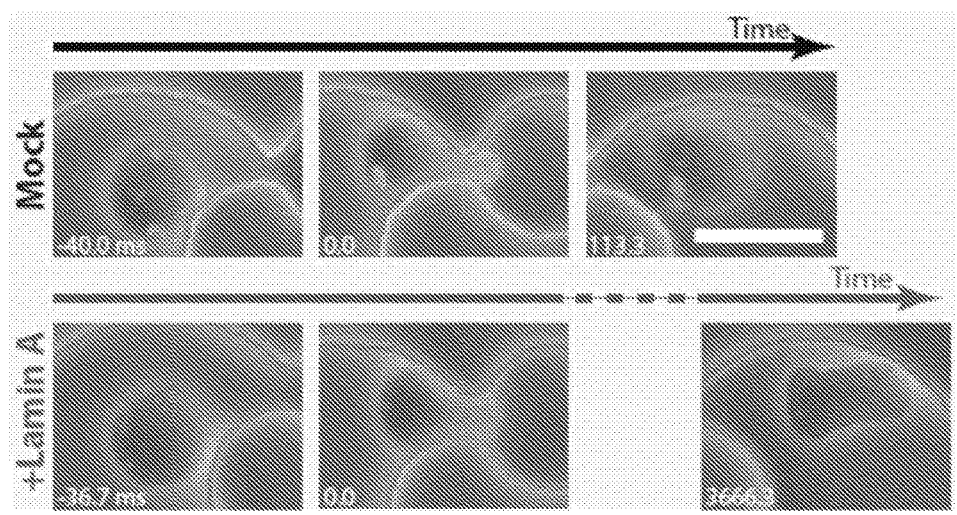
FIGS. 2A-2C illustrate the results from a preliminary study using the cell deformer microfluidic assay to differentiate HL60 cells that overexpress the nuclear scaffolding protein, lamin A, versus the mock controls.
Figure 2B:
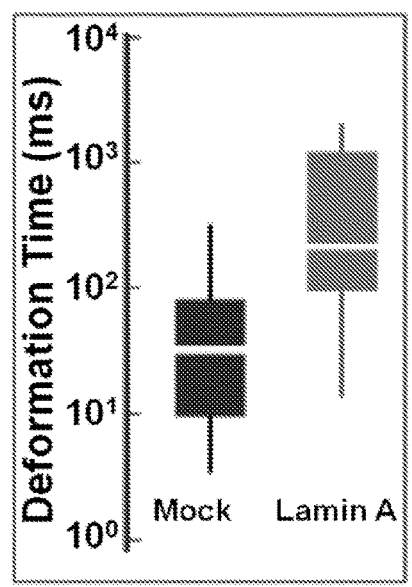
Figure 2C:
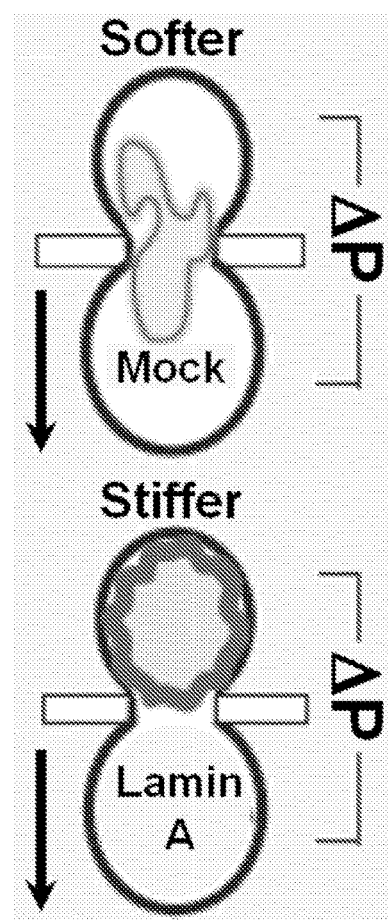
Figure 3:
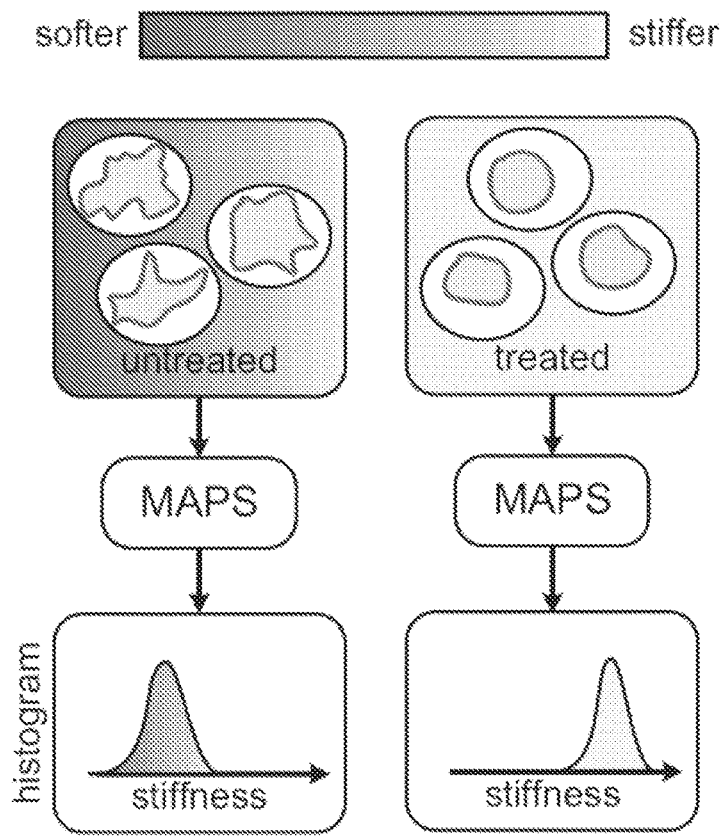
FIG. 3 illustrates how MaPS can be used to screen drug libraries efficiently. Cells treated with drugs are expected to exhibit an increased modulus, e.g., as shown in Lam, et al. (2007) Blood, 109: 3505-3508.
Figure 4:
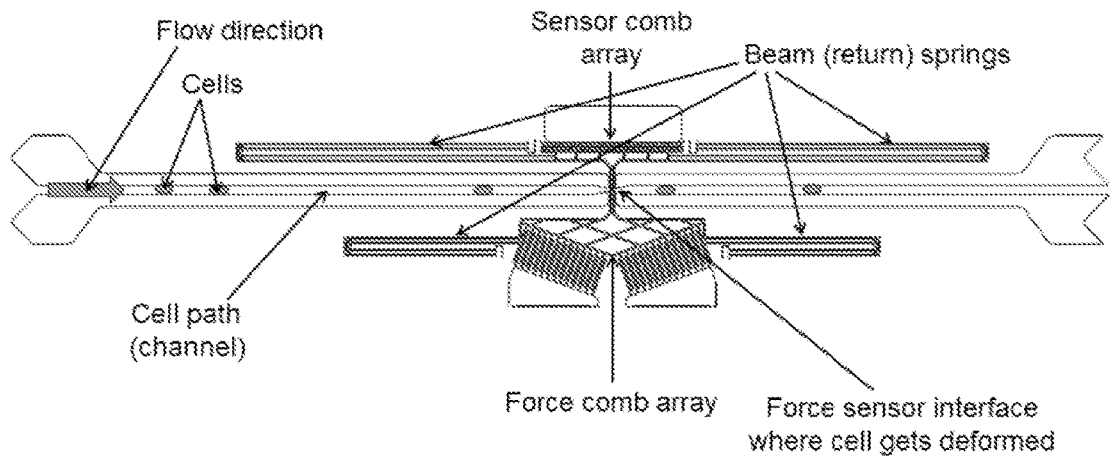
FIG. 4 illustrates a MaPS device integrating a MEMS oscillator and sensor within a microfluidic channel network.
Figure 5:
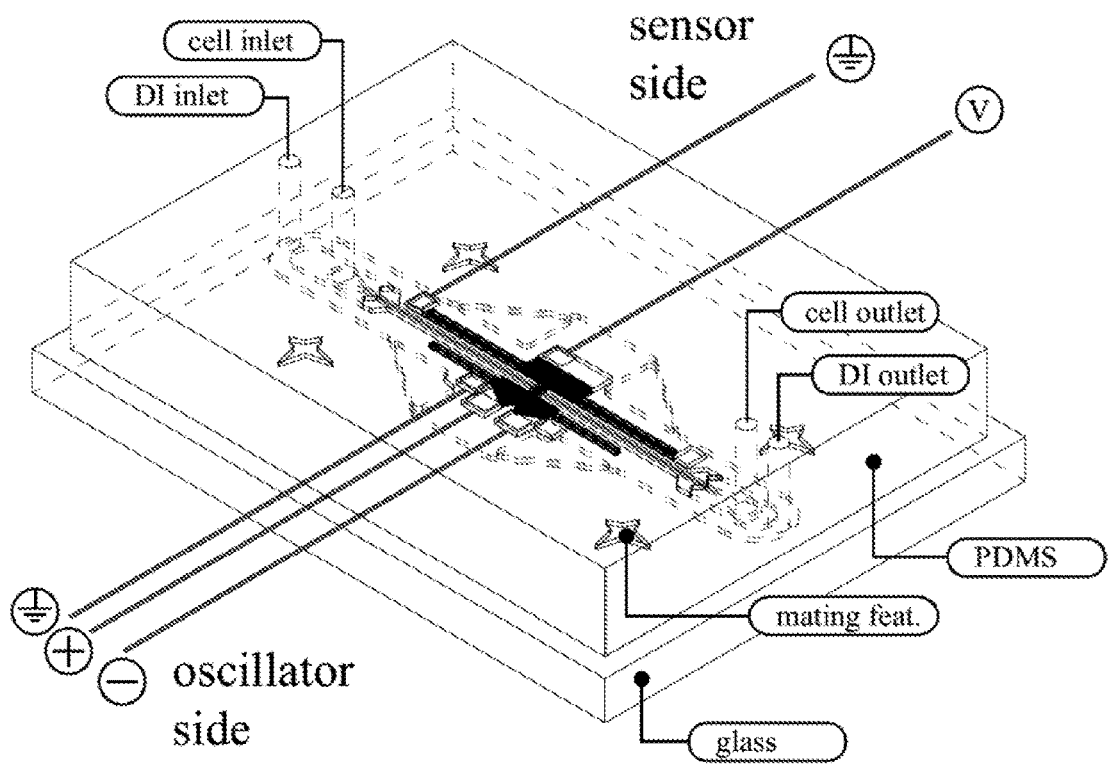
FIG. 5 illustrates the integration of a MEMS oscillator and sensor within a microfluidic channel network in a MAPs device.
Figure 6:
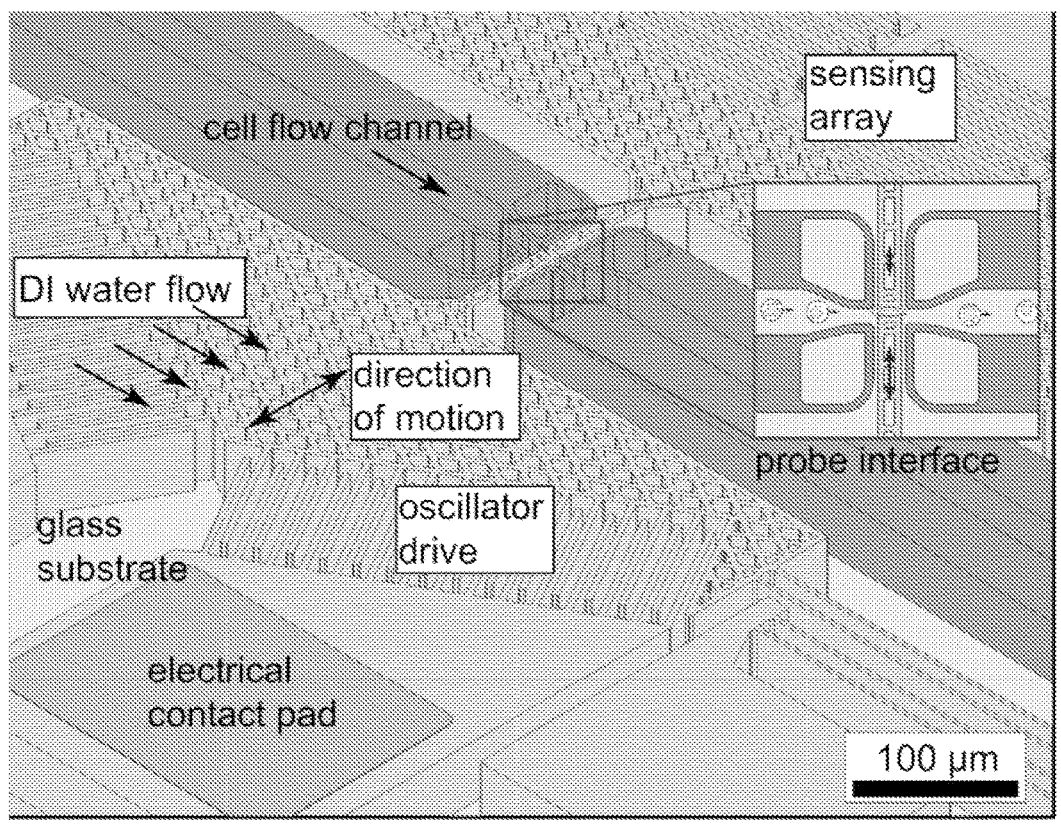
FIG. 6 illustrates an active MEMS device structure within the larger MaPS system. An oscillating drive probes cells as they passage over the probe interface. Force is transferred to the sensor probe as a function of the modulus of the cell. More detail given in FIG. 7.
Figure 7:
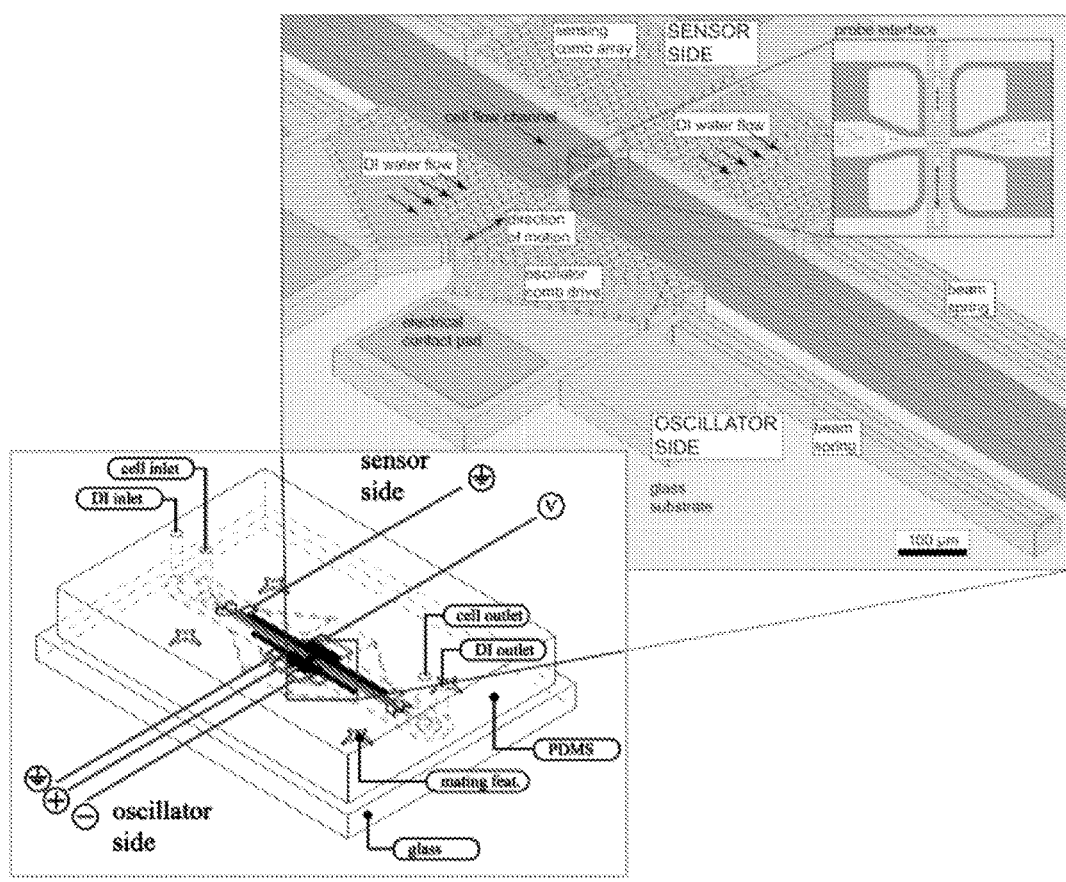
FIG. 7 illustrates a composite of FIG. 5 and FIG. 6 with more detail.
Figure 8:
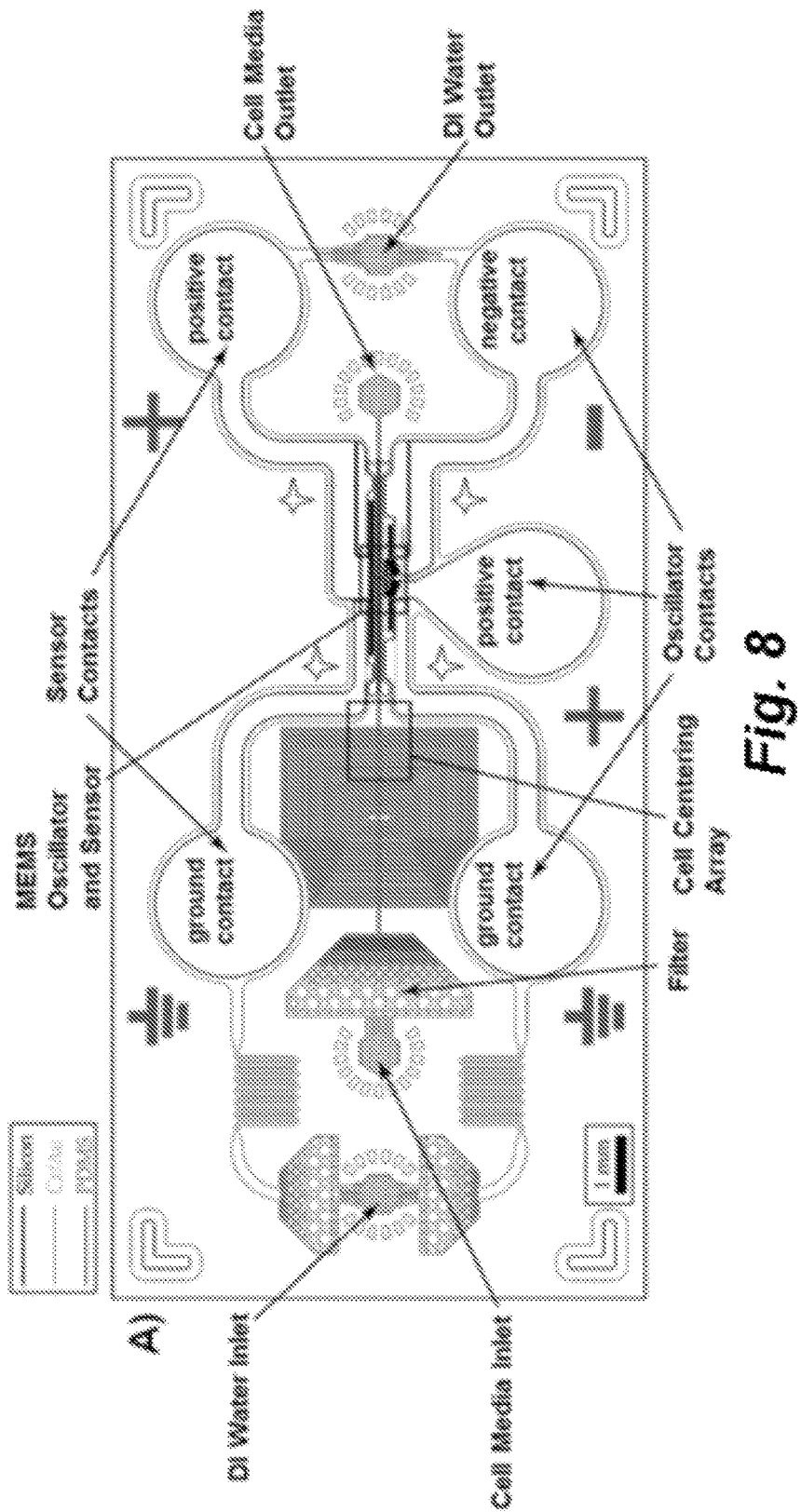
FIG. 8, panels A-E, illustrates a MaPS system in accordance with certain aspects of the devices described herein. As illustrated in Panel A, the microfluidic network has three parallel channels. Two DI water channels insulate electrical components and a cell media channel delivers cells to the MEMS device. The cell media channel has a filter to separate aggregates of cells and a centering circuit to align cells into a single-file. The MEMS device consists of an oscillator and sensor probe to measure displacement. The oscillator and sensor are driven and sensed, respectively, with comb arrays. Panels B-E illustrate various elements of the MAPs system. Panel B: Cell centering array. Panel C: MEMS oscillator and sensor. Panel D: Beam spring system. Panel E: Oscillator comb drive.

To achieve this aim, in certain embodiments the MaPS integrates an active microelectromechanical system (MEMS) with oscillator and sensor probes into a microfluidic device (see, e.g., FIG. 4 and FIG. 8). The approaches described herein builds on the strengths of existing methods for probing cell elastic modulus. However, the MaPS systems described herein enable both sensitive force probe measurements of individual cells and the ability to probe a large number of cells by continuously flowing cells past the force probe within a microfluidic network. Existing probe-based methods, such as AFM, are used to obtain precise measurements of the force-deformation response of individual cells that are fixed in position. On the other hand, microfluidic devices are capable of higher detection rates, but lack quantitative precision in mechanical measurements. For instance, the deformability of over 500 cells can be probed by flowing cells through the narrow constrictions of a microfluidic device (Rowat, et al. (2013) *J. Biol. Chem.* doi: 10.1074/jbc.M112.441535) (see, e.g., FIGS. 2A-2C), or by subjecting them to the forces generated by fluid interactions at elevated flow inertias (Hur et al. (2011) *Lab on a Chip*, 11: 912-920). While flow-based methods can achieve detections rates of over $10^2$ cells per second (Id.), these methods rely on computationally intensive image processing which is not implementable in real-time.

In contrast, MaPS exploits the flow of cells through the channels of a microfluidic device, together with a MEMS-based measurement system that processes analog signal data, and can therefore operate at significantly higher detection frequencies of $10^3$ cells per second. With detection rates that are comparable to FACS, this novel mechanical phenotyping approach has broad applicability in cancer prognosis and treatment and in other contexts.

Exploiting Flow in Microfluidic Channels to Manipulate Cells.

MaPS exploits the flow through microfluidic channels to move cells past the force and sensor probes at unprecedented rates. The main fluid line of MaPS is the cell flow channel (see, e.g., FIG. 4). Cells flow through the flow channel and an oscillator probe and sensing probe (e.g., as described below) measure the mechanical response of the cell(s) to applied force(s).

Figure 9:
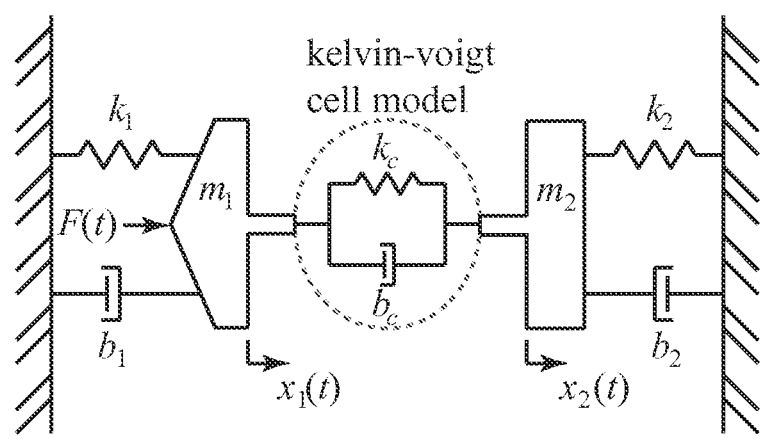
FIG. 9 illustrates a simplified model of a MEMS oscillator and sensor.

The compliance of soft materials such as cells can be calculated by measuring the displacement of a calibrated structure with a similar compliance in contact with the test material. In static contact, the relative displacements of the cell, $\delta_c$, and calibrated structure, $\delta_s$, are realized as a displacement divider:

$$\frac{\delta_c}{\delta_s} = \frac{k_s}{k_c}$$

where the ratio of displacements is the inverse ratio of the effective spring constants of the two materials, $k_c$ and $k_s$. The spring constants assume a geometry and material modulus. Calibrated beam structures have well defined models for effective spring constant calculations. Cells are less straight forward. In one illustrative approach, a linearized Hertz contact model (Landau and Lifshits, *Theory of Elasticity*: Pergamon Press, 1965) (elastic sphere in contact with flat plates) to infer an effective spring stiffness from a cell modulus and also assume that the cell response depends on contact velocity, assuming the form of the kelvin-voigt model (FIG. 9).

Analogous to many common mechanical phenotyping methods, MaPS detects the cell mechanical phenotype by deflecting the cell with a calibrated probe. The primary detection mechanism is a microelectromechanical system (MEMS) probe. Through modeling of different design parameters, in certain embodiments, the chosen MEMS design incorporates two probes positioned on opposing sides of a microfluidic channel (see, e.g., FIG. 4). On one side, an oscillating probe oscillates with a frequency on the order of 200 Hz up to 2 kHz, or from about 300 Hz up to about 1 kHz, or from about 400 Hz up to about 600 Hz, and in certain embodiments around 500 Hz and a displacement on the order of from about 4 to about 25 µm, or from 5 to about 10 µm, and in certain embodiments, about 10 µm. Directly opposite, a displacement sensor tuned to be sensitive to the forcing inputs e.g., to a 500 Hz forcing input measures the displacement imposed by the oscillator forcing the cell into the sensor. The oscillator and sensor are used herein when referring to these components.

In various embodiments the oscillator probe oscillates at a frequency such that passing cells are probed multiple (e.g., approximately 1-5) times during the brief ~10 msec time period during which the cell is flowing past the probe interface. In the absence of any cell, the displacement of the oscillator probe into the fluid-filled channel will simply displace fluid. However, when a cell passes across the probe interface, the force generated by the moving oscillator probe will be transmitted through the cell to the opposing sensing probe; the resulting displacement of the sensing probe will depend on the elastic modulus of the passaging cell.

The cell detection frequency can be tuned by regulating the density of cells in suspension and the fluid flow rates using syringe (or other) pumps. Manipulating the flow of cells through micron-scale channels also provides exquisite control over the position of cells at the probe interface of the MEMS device for detection. In certain embodiments, sheath flow can be used to focus cells into a single streamline for detection in the systems described herein.

Force Probe for kHz Detection Rates.

In certain embodiments the two probes for driving and sensing use an array of interdigitated combed fingers, or comb drives. To actuate a probe, a voltage (potential) is placed across the comb pairs to generate an attractive force. To operate as a position sensor, the position dependent capacitance can be measured across comb pairs. Both the actuated and sensor probes can be returned to their neutral position by slender beam springs (see. e.g., FIGS. 4-8). Beam architecture can be designed to only permit movement along the direction of motion and not appreciably in perpendicular frames. In various embodiments the entire MEMS device can be micromachined from a single die, e.g., of doped silicon. To achieve rapid detection, the position of the oscillator can be driven at a fundamental frequency of, e.g., 500 Hz as indicated above.

The complete oscillator, sensor, and cell system can be modeled by assuming that the oscillator and sensor each act as a mass, spring, damper system and the cell acts as a kelvin-voigt material (see, e.g., FIG. 9). The oscillator and sensor are each fixed to a solid substrate through their respective springs and the oscillator is driven by an applied exogenous force. The spring constant and mass of the oscillator and sensor can be designed by tuning the probe geometry. The frequency response of the oscillator/cell/sensor system is evaluated over the range of anticipated driving frequencies to guide the design.

Figure 10:
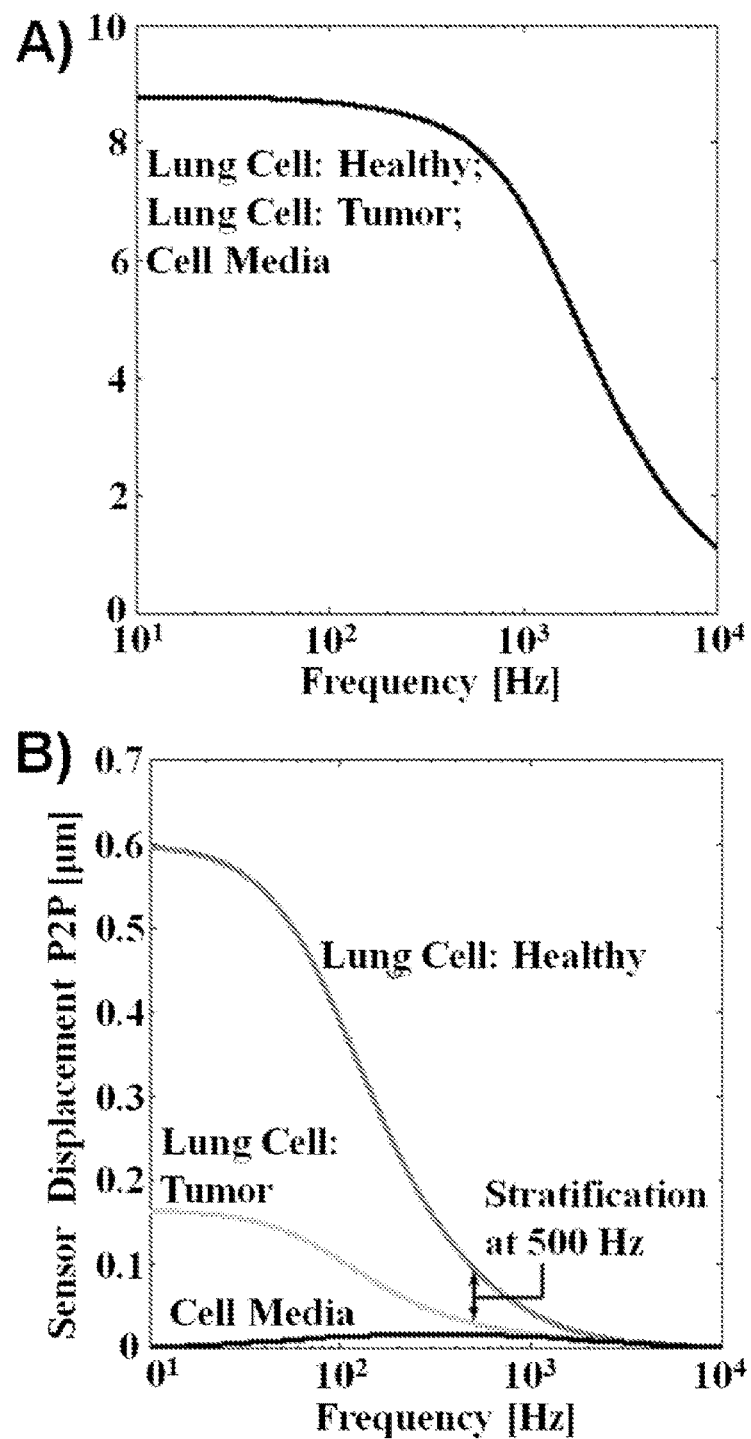
FIG. 10, panels A-D, illustrates the results of a frequency response study of a MaPS device. Panel A: Oscillator frequency response for $k_2=0.5$ N m$^{-1}$. Panel B: Sensor frequency response for $k_2=0.5$ N m$^{-1}$. Panels C and D: Demonstration of simulations from a design study that accommodates a wide range of $k_2$ values to select a sensor spring constant $k_2$. Panel C: Displacement stratification at 500 Hz actuation frequency between a healthy lung cell and a tumorous lung cell for a range of expected sensor damping coefficients and designed spring constants. Panel D: Level sets from Panel C.

One contemplated application of MaPS is high-throughput diagnosis of neoplastic cells (tumorous or non-tumorous cancer cells). In this context, one important metric is the estimated stratification of sensor displacement signals between a healthy cell and neoplastic cell (Cross et al. (2010) *Nature Nanotechnology*, 2: 780-783) at frequencies on the order of, e.g., 500 Hz. FIG. 10, panel A, illustrates the oscillator frequency response for $k_2$=0.5 N m$^{-1}$, while FIG. 10, panel B, illustrates the sensor frequency response for $k_2$=0.5 N m$^{-1}$. FIG. 10, panels C and D illustrate a design space for spring constant $k_2$ over a range of anticipated damping coefficients as empirically determined from previous design iterations. Sensor displacements are small and therefore sensor fidelity is of importance. A sensor spring constant of $k_2$=0.50 N m$^{-1}$ yields a frequency bandwidth and measurement stratification sufficient to discriminate amongst cell mechanical phenotypes.

MEMS Components

Oscillator and Sensor.

In an illustrative embodiment, the oscillator and sensor are etched from of a single die of low-resistivity silicon bonded to a glass substrate. Moveable structures are perforated to permit the moving members to be released from the glass substrate by a timed acid etch of the underlying glass substrate. Large monolithic structures (e.g., >20 µm feature size) remain bonded to the glass. In one embodiment, each spring is comprised of eight long slender beams cut from the silicon and the system of beams is designed to have a specified spring constant.

The oscillator and sensor can be driven and sensed by an array of parallel plates in the form of combed fingers. Arrays such as these, termed comb drives, are common in MEMS actuators and sensors (Dong et al. (2007) *J. Micromechanics Microengineering*, 17: 154-1161; Sun et al. (2002) *Sensors and Actuators A*, 102: 49-60; Sun et al. (2002) *J. Micromechanics Microengineering*, 12: 832-840). Actuators are driven by applying a voltage potential across the comb pairs to generate an attractive electrostatic force; displacement is sensed by measuring a change in capacitance. There are two basic designs: 1) longitudinal design ($\theta$=0° in FIG. 8, panel E) where the moving combs traverse parallel to the comb faces and 2) latitudinal design ($\theta$=90° FIG. 8 panel E) where the moving combs traverse perpendicular to the comb faces. Characteristically, longitudinal drives apply relatively weaker forces but achieve relatively higher displacements than latitudinal drives. In certain embodiments the oscillator design used in the MaPs devices is a hybrid of the longitudinal and latitudinal designs with 0 ranging from about 5° up to about 40°, or from about 10° up to about 30°, or from about 15° up to about 25°. In one illustrative, but non-limiting embodiment $\theta$=20° (FIG. 8, panel E). This configuration achieves large-displacements (almost 3× greater range than a latitudinal design) and high-force (2.5× greater than a longitudinal design at the neutral position and 25× greater at full displacement). Furthermore, the displacement dependent nonlinearity that leads to the deleterious 'pull-in' instability in a latitudinal design is severely diminished (Sun et al. (2002) *Sensors and Actuators A*, 102: 49-60).

Figure 11:
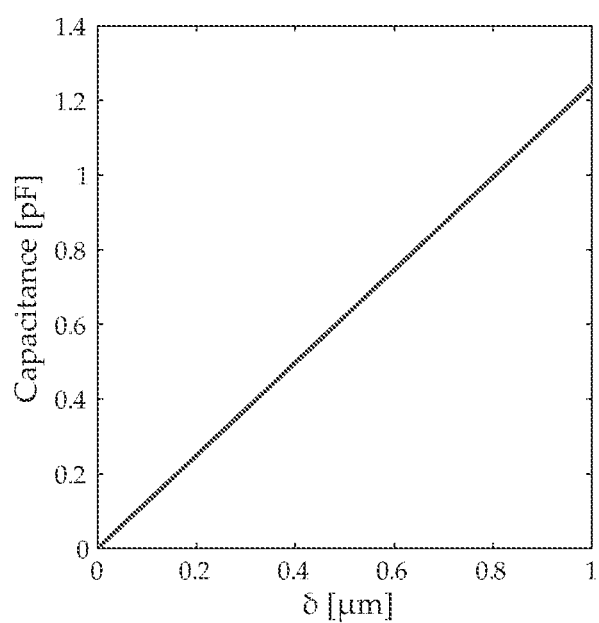
FIG. 11 shows that sensor capacitance is a linear function of sensor displacement for certain design versions (e.g., design version 2). However, in certain configurations/designs, the relationship need not be linear.

The sensor can have a longitudinal comb array design because, in certain embodiments, the sensor spring, $k_2$, is designed to be an order of magnitude weaker than the oscillator to sense soft cellular materials and the signal (e.g., a 100 kHz square-wave signal) utilized by the capacitance measurement circuit, may in certain embodiments, impose a small force on the sensor. A longitudinal design minimizes the forces. Sensor capacitance is a linear function of sensor displacement (see, e.g., FIG. 11). One illustrative capacitance sensor (MS3110BDPC-USB, Irvine Sensors, Irvine, Calif.) has a resolution of approximately 89 aF, providing approximately 1400 lines of resolution for discriminating between a cancerous versus healthy cell, by the analysis plots in FIG. 11 and FIG. 10, panel B.

Microfluidic Network

The MEMS oscillator and sensor are typically integrated into a microfluidic network. The microfluidic network is designed to perform two functions: 1) deliver a single-file stream of cells to the MEMS device for measurement and 2) immerse the oscillator and sensor electronics in water (e.g., DI water) with minimal mixing of water and cell media. In certain illustrative, but non-limiting embodiments the microfluidic network primarily consists of a PDMS (or other soft lithography material) "cap" with relieved channel architecture that seals around the MEMS devices. A small section of the fluidic network can be defined by etched silicon members.

Cell Media Channel

As illustrated in FIG. 8, in certain embodiments the cell media channel consists of an inlet port, cell filter to disaggregate clumps of cells and filter out debris, a cell centering region, a constriction to deliver cells to the MEMS probe interface, and an outlet port. The cell centering circuit uses the carrier fluid as the actual sheath flow (Aoki et al. (2009) *Microfluidics and Nanofluidics*, 6: 571-576). Multiple parallel bypass channels extract carrier fluid but not larger objects such as cells in the first half of the network and then reinject the extracted fluid axially in the second half of the network. This bypass design effectively reduces fluid velocity around a stream of uniformly distributed cells and then centers the cells by a sequence of low-velocity fluid flows impinging perpendicularly on the cell stream. See FIG. 31 for experimental results demonstrating the centering of a cell stream.

DI Water Channel

To provide physiologically relevant measurements, the device can be operated in an aqueous environment as described above. However, cell media typically has an ionic concentration on the order of ~150 mmol and can cause a serious charging effect if the MEMS device is operated with a simple DC or low-frequency (e.g., <10 kHz) sinusoidal voltage. However, electrostatic comb drives can be operated in ionic solutions if a signaling scheme is employed that flips the bias on the dissolved ions faster than the ions can physically rearrange (Mukundan et al. (2009) *J. Micromechanics and Microengineering*, 19: 065008; Mukundan and Pruitt (2009) *J. Microelectricalmechanical Systems*, 18: 405-413; Sounart et al. (2005) *J. Microelectricalmechanical Systems*, 14: 125-133; Sameoto et al. (2004) *J. Micromechanics and Microengineering*, 14: 1359-1366). In certain embodiments the polarity of the signal switches at a rate on the order of ~10-100 MHz for high ionic concentration fluids, which approaches the limit of conventional function generators. Researchers have demonstrated severely degraded electrostatic force at 150 mmol concentration. In contrast, MEMS devices submerged in DI water can be effectively operated at much lower frequencies, e.g., ~100-500 kHz, without force degradation (see, e.g., Mukundan et al. (2009) *J. Micromechanics and Microengineering*, 19: 065008).

Accordingly, in certain embodiments, the MaPS design integrates provides a microfluidic network has at least two fluid paths (fluid lines). A distilled or deionized (DI) water path that electrical components are immersed in a steady stream of substantially pure (e.g., DI) water, where the optimal frequency is only ~0.5 MHz and a cell media path that contains the cells. The water and cell media paths will mix near the force probe regions, however the microfluidic networks contemplated herein typically operate in the laminar flow regime and mixing occurs by diffusion only. Consequently, the DI water and cell media will not mix appreciably on the time scale of fluid residence within the MaPS.

Salient Features

There are a few microfluidic design details that aid MaPS performance. The PDMS "cap" is molded over a two-level master pattern with a main level that defines the major features and a thin (e.g., ~5 µm high) relief level that provides extra clearance between moving MEMS members and the PDMS walls. The relief is designed to effectively decrease the viscous damping terms, $b_1$ and $b_2$, in FIG. 9.

In various embodiments electrical contacts (e.g., tabs) protrude through punched holes in the PDMS. The contactors can be spring loaded to maintain electrical contact and the holes can be sized to snugly hold the contactor in place and not leak fluid.

MPaPS Systems

Figure 12:
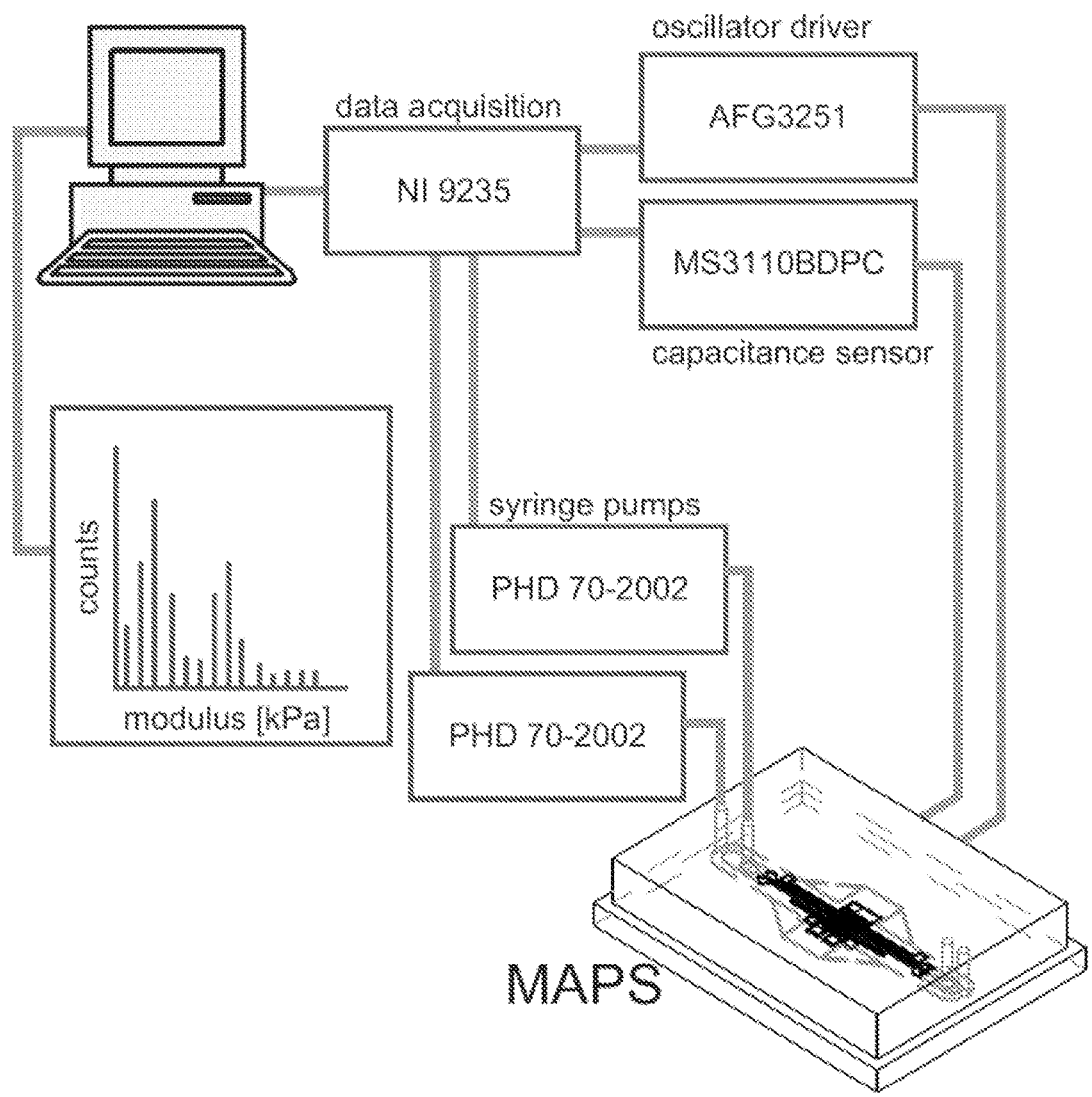
FIG. 12 provides a schematic illustration of one integrated system for controlling and sensing events in the MaPS.

An overview of high-level components comprising an illustrative, but non-limiting embodiment of a MaPS system is shown in FIG. 12. On the macroscale, MaPS is interfaced with a computer (microprocessor) with a data-acquisition (DAQ) board, a high-frequency signal generator, capacitance sensing hardware, and controllable pumps (e.g., syringe pumps). On the microscale, MaPS consists of a microfluidic network that separates, centers, and delivers cells to a detection location and an oscillating MEMS actuator and sensor for mechanical phenotyping of cells conveyed in cell media as the carrier fluid, e.g., as described above. In parallel to a cell media conveying stream, a distilled or deionized (DI) water stream can be used to insulate electrical components from high ionic concentration cell media. The system is scaled/operated in a laminar flow regime, thereby minimizing convective mixing to maintain segregated streams.

Electrical System and Peripherals

Figure 13:
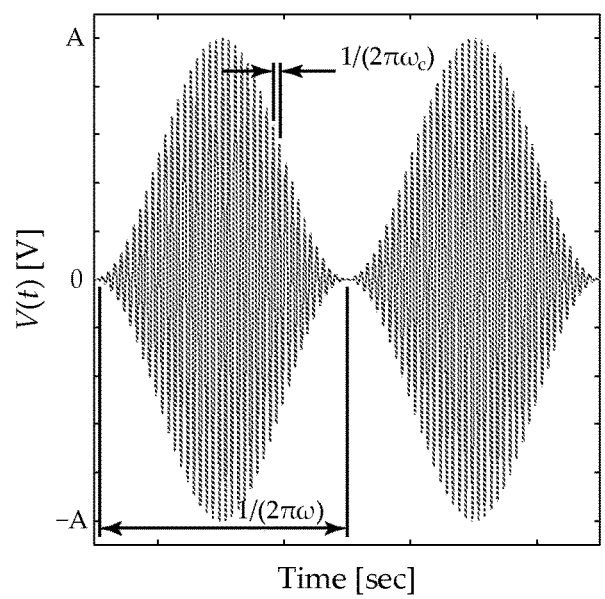
FIG. 13 illustrates an amplitude modulated forcing function.

The MaPS with features on the microscale is interfaced with macroscale hardware to drive electrical signals and fluids. The electrical signals are specifically designed to drive a system with charged surfaces immersed in an aqueous medium. Similar to Mukundan and Pruitt (2009) *J. Microelectricalmechanical Systems*, 18: 405-413, MaPS can use a high-frequency signal scheme to mask ionic effects. However, instead of a sinusoid with constant amplitude, in certain embodiments MaPS uses an amplitude modulation (AM) signaling scheme in which the fundamental frequency (order of 500 Hz) is modulated with a high-frequency (order of 500 kHz) carrier frequency:

$$V(t) = A(\tfrac{1}{2} + \tfrac{1}{2}\sin\omega t)\sin\omega_c t \quad (1.1)$$

where A is the signal magnitude and $\omega$ and $\omega_c$ are the fundamental and carrier frequency, respectively (FIG. 13).

Force is approximately proportional to the voltage squared ($F(t) \propto V(t)^2$). Expanding $V(t)^2$ out to a sum of sinusoids, that Eqn. (1.1) is mapped to a DC component, a high-magnitude component at $\omega$, a component at $2\omega$ with one-fourth the magnitude of that at $\omega$, and five inconsequential high-frequency terms (H.F.T.) near $2\omega_c$.

$$F(t) \propto A^2\left(\frac{3}{16} + \frac{1}{4}\sin\omega t + \frac{1}{16}\sin\left(2\omega t - \frac{\Pi}{2}\right) + H.F.T.\right)$$

The fundamental frequency is within the bandwidth of the oscillator and the oscillator will respond immediately to this lower-frequency signal with essentially zero-phase lag (FIG. 10, panel C). The carrier frequency is sufficiently above the oscillator and sensor bandwidth and will be fully attenuated. The capacitance sensor (e.g., Irvine Sensors MS3110BDPC-USB, Costa Mesa, Calif.) applies a 100 kHz square wave to the sensor array. Although intended to measure array capacitance, this also applies an attractive force to the array. The DC component is mapped to a comb force, in this example, with a magnitude of 0.125 µN which deflects the array by 0.25 µm and the harmonics at and above 100 kHz are all attenuated.

Operation

In various embodiments the oscillator/sensor measurement system is based on analog and digital signal processing. Preliminary results from dynamic simulations of the MEMS device indicate that a capacitance measurement system is capable of detecting relevant differences in moduli between cells. The measured signal of a "healthy" human cell with elastic modulus of ~2 kPa, is about four times greater than that of a cancerous cell (e.g., human promyelocytic leukemia cells (e.g., HL-60 cells)), ~0.5 kPa (Suresh (2007) *Acta Biomaterialia*, 3: 413-438). In various embodiments the sensor displacement can be measured with a capacitance sensing board (e.g., Irvine Sensors MS3110BDPC) that is integrated with a commercial software system. Other MaPS components can also be interfaced with the computer software for unified control. In certain embodiments the oscillator can be driven by a signal generator (e.g., Tektronix AFG3251). This fully flexible voltage source can enable the user to interchangeably and simultaneously probe different depths, e.g., as described below. In certain embodiments syringe pumps (Harvard Apparatus), or other pumps or fluid delivery devices can be used to control fluid flow rates. In certain embodiments pressure-driven flow can be used to regulate fluid flow rates. Data can be acquired and logged using a data acquisition system (e.g., NI 9235). A software package (for example, written in LABVIEW®) can provide a graphical user interface that permits full control of all integrated systems (see, e.g., FIG. 12).

In certain illustrative embodiments the device can be operated with a fundamental frequency of, e.g., 400 Hz or 500 Hz, and a carrier frequency of 0.5 MHz. This signal scheme is fundamentally identical to amplitude modulated (AM) radio signals. Importantly, the DC offset of the forcing signal can be tuned to regulate the probe deflection distance (e.g., through a range of ~0 µm to ~6 µm). This enables the user to probe different depths into the cell, for example, to measure either the cytoskeletal or nuclear mechanical properties. The ability to control probe depth can also accommodate a larger range of cell (or particle) sizes (e.g., approximately 1 µm to about 1 mm, or about 1 µm or about 2 µm, or about 3 µm, or about 4 µm, or about 5 µm up to about 500 µm, or up to about 250 µm, or up to about 150 µm, or up to about 100 µm, or up to about 50 µm, or up to about 40 µm, or up to about 30 µm, or up to about 20 µm, or up to about 15 µm, or up to about 5 µm) than static microfluidic devices that are constrained to a predefined channel architecture.

To achieve higher detection rates multiple MEMS probes can be integrated into a single microfluidic network with a branched architecture. In certain configurations of such embodiments cells travel in one inlet and then branch out to different MEMS sensors.

In certain embodiments all MEMS oscillators can be driven by the same driving signal distributed in a parallel architecture. Sensor capacitance gauges can be measured independently. Displacement measurements from the interdigitated combed fingers at the sensor probe can mapped to a transmitted force using a known spring stiffness. Sensor can data is logged by a computer and displayed with a simple user interface for interpretation; for example, a histogram-format similar to FACS is a convenient way to visualize the modulus measurements that are obtained for >100 cells/sec (FIG. 12). In certain embodiments the software package will feature statistical tools to assess population means and variances. Such comprehensive statistical analysis of mechanical properties across large populations of individual cells is not possible using current mechanical phenotyping technologies. The MaPS systems and devices described herein thus represent a significant advance in diagnostic capabilities.

Fabricating MaPS.

In various embodiments the MaPS device integrates a MEMS actuator within a microfluidic channel. The MEMS device can be fabricated through a series of standard lithographic processes to create micron-scale moving structures whose position can be regulated with 100 nm spatial resolution to probe individual cells. More than 200 individual MEMS devices can be fabricated on a single four-inch silicon wafer. One illustrative etch mask for etching the MEMS features (displayed in gray in FIG. 6) is displayed in FIG. 15 and illustrative results from etch experiments are displayed in FIG. 16.

In one illustrative approach, the MaPS is fabricated in two parallel workflows, both utilizing lithographic micromachining. The MEMS device mounted on glass and the microfluidic network are fabricated independently and then aligned and bonded in the final fabrication step to finish the MaPS device. Illustrative MEMS, microfluidic, and MEMS/microfluidic integration fabrication procedures are described below.

MEMS Fabrication

Figure 41:
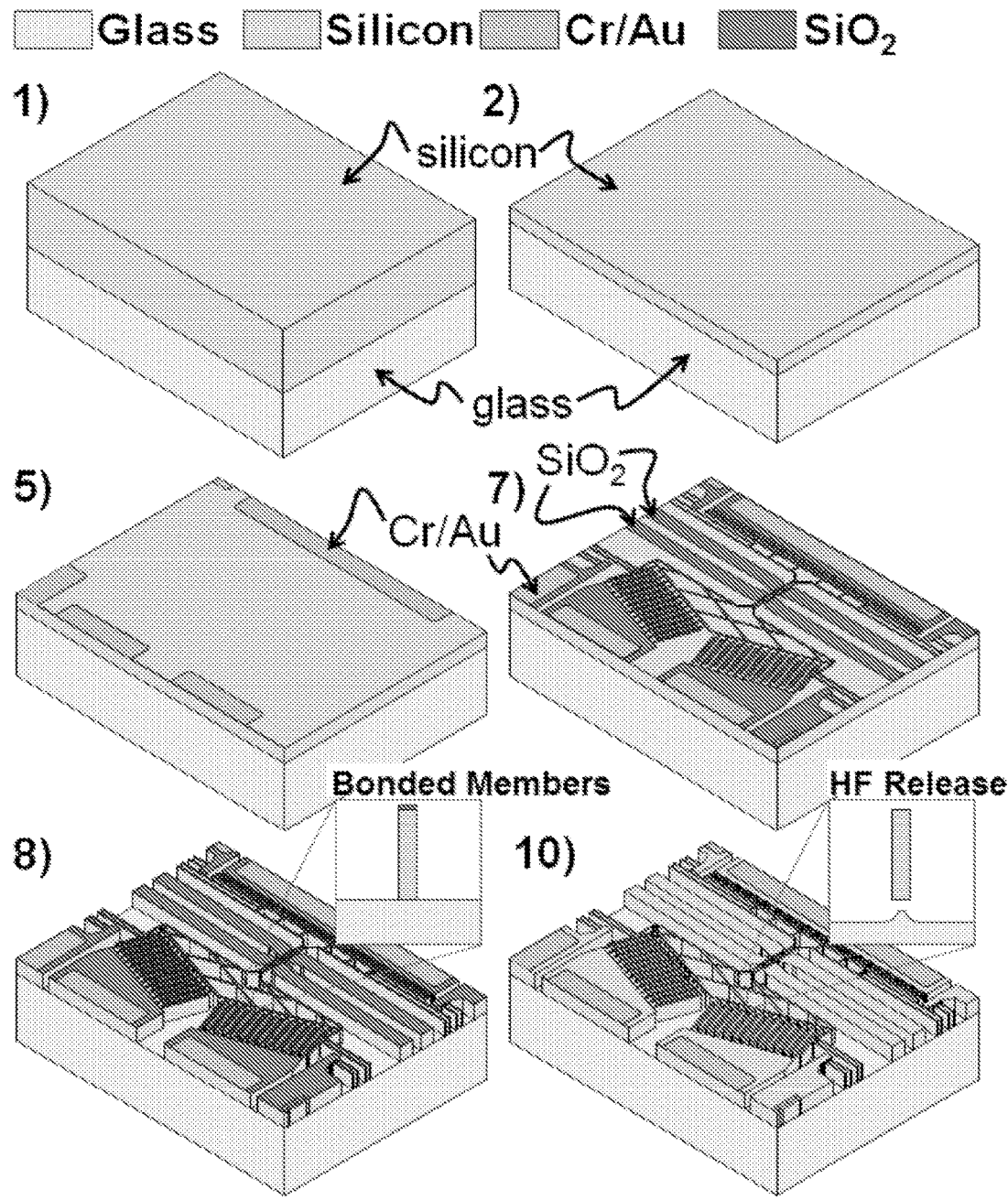
FIG. 41 schematically illustrates major lithographic steps in MEMS fabrication. 1) Anodically bond an Si wafer to a glass wafer. 2) Thin the Si side to 50 μm. 5) Pattern gold contact pads. 7) Pattern an SiO$_2$ etch mask. 8) DRIE etch Si members. 10) Release moving members with a timed HF etch.

One illustrative and non-limiting approach to MEMS fabrication is schematically illustrated in FIG. 41 and detailed below:

1) A low-resistance (0.005-0.020 Ω-cm) p-type silicon wafer with <1-0-0> orientation (Ultrasil, Hayward, Calif.) is anodically bonded (e.g., using a Karl-Suss bonder) to a Pyrex 7740 glass wafer (Plan Optik, Elsoff, Germany) (see, e.g., step 1 in FIG. 41).

2) The Si side is thinned, e.g., to 50 μm lapping and polishing to the industry standard finish (RMS~1 nm; performed by Aptek Industries, San Jose, Calif.) (see, e.g., step 2 in FIG. 41).

3) A Cr/Au film is deposited on the silicon surface by electron beam evaporation (CHA Solution; 8.5 nm Cr, 392 nm Au).

4) An etch mask is patterned by spin coating with photoresist (e.g., SPR700-1.2), exposing to UV, and developing to open the features to be etched. Note that devices are oriented such that the oscillator and sensor move parallel to the <1-0-0> plane.

5) Cr/Au film is selectively etched in a timed acid etch (TFA Gold Etchant (Transene, Danvers, Mass.) followed by CR-7S (Cyantek, Fremont, Calif.)).

6) A 750 nm $SiO_2$ film is deposited by PECVD (Plasmatherm 790).

7) The device layer etch mask is fabricated by photolithography and dry etching.

8) DRIE silicon features through to the glass (Unaxis DRIE) (see, e.g., step 8 in FIG. 41).

9) Individual dies are separated by wafer dicing.

10) Moveable MEMS members are released from the glass layer by a timed HF wet etch of the glass layer (1:1 $HF:H_2O$, solution stirred at 100 rpm). This step also removes the remaining $SiO_2$ etch mask (see, e.g., step 10 in FIG. 41).

11) The MEMS devices are dried by critical point drying.

Figure 14:
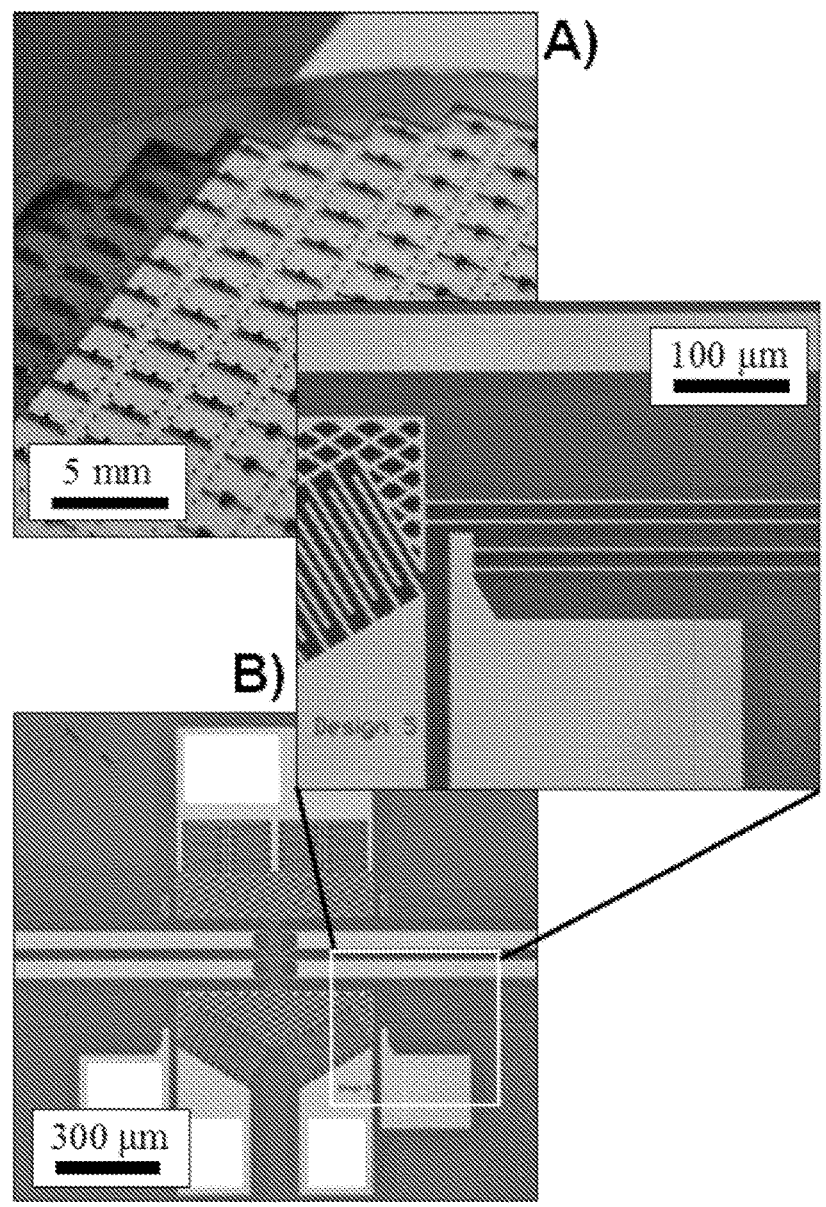
FIG. 14, panels A-C, illustrates fabricated MEMS components of one illustrative, but non-limiting embodiment of a MaPS device. Panel A: 380 individual MEMS devices fabricated on a single 100 mm glass wafer. Panel B: Reflected light microscope images of the Si members etched through to the glass. Panel C: Scanning electron microscope images of the MEMS device demonstrating the complete device and critical features.

Fabrication images demonstrate the high fabrication fidelity achievable by the designed workflow (FIG. 14). Importantly, micromachining has been developed primarily for high-resolution integrated circuit manufacture and therefore features on the order of the cell length scale are easily achievable by tools in standard cleanrooms. As measured by optical and scanning electron microscopy, all features can be fabricated within half a micron of the designed feature sizes (see, e.g., FIG. 14, panel C). Silicon members directionally etched by DRIE have minimal scalloping. Nanometer scale defects from ion bombarding and then reflecting off the surface of the glass at the Si/glass interface can be observed through SEM. However, given the length scale of the defects in comparison to size of the features it is unlikely that these superficial defects affect MEMS performance.

PDMS Microfluidic Channel Fabrication

In various embodiments the PDMS (or other soft-lithographic material) "cap" that seals the device and defines the microfluidic network architecture can be fabricated by standard soft lithographic methods (Rogers and Nuzzo (2005) *Materials Today*, 8: 50-56). Briefly, SU-8 (MicroChem Corp., Newton, Mass.) negative photoresist is spun on a Si wafer to a desired thickness; the photoresist forms the negative of the microfluidic channels so the desired thickness will be the desired channel height. The photoresist is selectively exposed to UV light to crosslink the polymer and then heated in a post-exposure bake. Unexposed photoresist is dissolved in a developed solution and remaining photoresist is fully hardened with a hard bake. PDMS prepolymer and cross-linking agent (Sylgard 184, Dow Corning, Midland, Mich.) are poured over the microfabricated negative, degassed, and then baked to cross-link. Individual PDMS dies are cut from the poured PDMS block and access ports are punched in the PDMS using a biopsy punch.

In certain embodiments the MaPS design utilizes a two-tier PDMS mold. The main tier, 50 μm in height, defines the microfluidic network architecture while a shorter 10 μm tier creates a recess above the movable MEMS members to facilitate their motion. The two-tier architecture can be fabricated using two photoresist applications and exposures (see, e.g., Doll (2009) *Lab on a Chip*, 9: 1449-1454).

While the foregoing discussion references PDMS as the soft lithographic material, numerous other materials are also suitable and the device(s) described herein are not limited to particular materials or configurations. In this regard, it is noted other elastomers are suitable. Such elastomers include, but are not limited to alkylated chlorosulfonated polyethylene (e.g., ACSIUM®), polyolefin elastomers (e.g., ENGAGE®), chlorosulfonated polyethylene (e.g., HYPALON®), perfluoroelastomer (e.g., KALREZ®), neoprene-polychloroprene, ethylene-propylene-diene terpolymers (EPDM), chlorinated polyethylene (e.g., TYRIN®), various siloxane polymers (e.g., polydimethylsiloxane, etc) and the like.

Calibrating MaPS.

The MaPs system can be validated using, for example, human promyelocytic leukemia (HL60) cells that are known to exhibit differences in mechanical moduli upon drug treatment (Lam, et al. (2007) *Blood*, 109: 3505-3508). To develop a more detailed, empirical relationship between model cell mechanics and measured sensor data, the MaPS can be calibrated using polymeric "model cells."

Polyacrylamide particles can be purchased or fabricated that have a defined elastic modulus (e.g., ~0.1 to ~10 kPa) and size (e.g., ~10 to ~30 μm) that is similar to cells. The model cells can be fabricated using a separate microfluidic device to generate drops of water-in-oil emulsions: the aqueous contains the necessary precursors to form a polyacrylamide gel. By increasing the density of chemical crosslinks within the polyacrylamide particles model cells can be generated with increasing elastic moduli. By tuning the channel width and flow rates particle size can be tuned (Seiffert and Weitz (2010) *Soft Matter,* 6: 3184-3190). Such fabrication methods can be used to generate microgel particles composed of various biopolymers, such as fibrin, collagen, or alginate that may better recapitulate the viscoelastic properties of cells. Such gels can also provide an important calibration step for MaPS. While the bulk properties of hydrogels correlate well to the mechanical properties of micron-scale gel particles (Id.), model cell mechanical properties can also be validated using, for example, AFM (CNSI) and micropipette aspiration.

Various Illustrative Configurations

Using the teachings provided herein, numerous variations of the devices and methods will be available to one of skill in the art. For example, a number of different designs are illustrated in the examples. In various embodiments wafers of MEMS devices are fabricated with a number of configurations of MaPs on them.

Figure 15A:
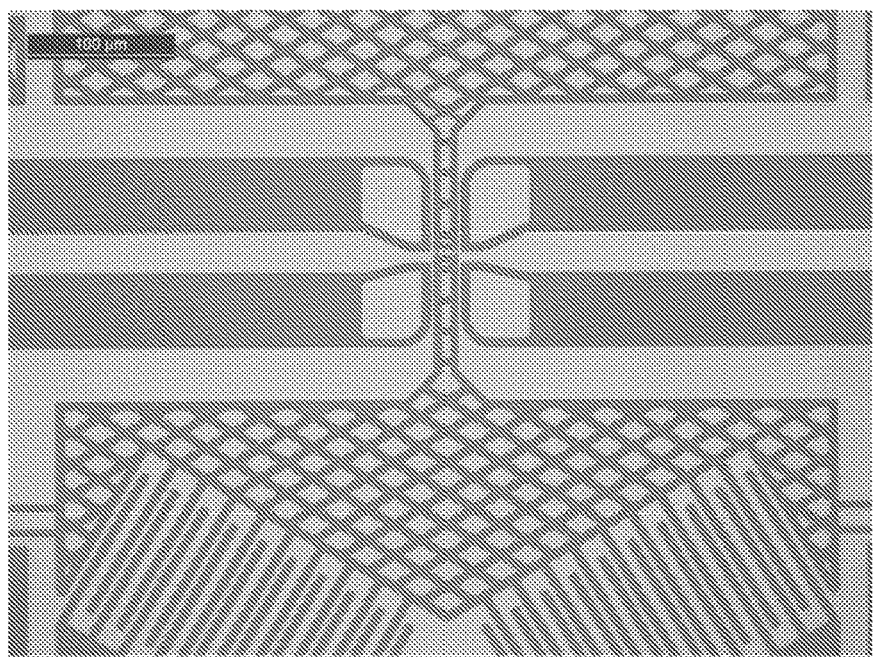
FIGS. 15A and 15B illustrate a silicon oxide etch mask on a silicon substrate. Etch mask protects regions from etching; subsequent deep etch remove silicon, revealing the features illustrated in FIG. 6. Preliminary results for 15A are shown in FIG. 16.
Figure 15B:
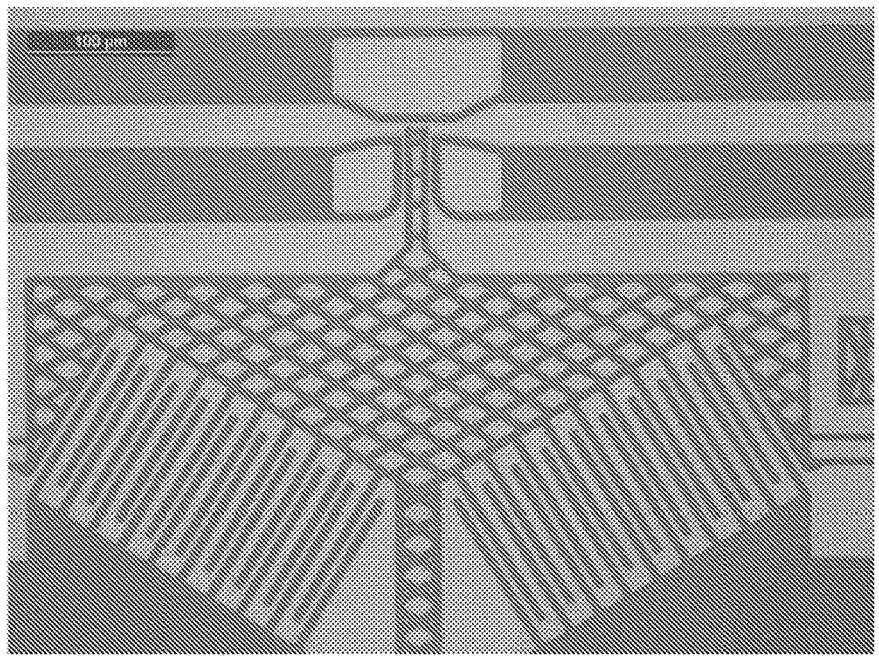
Figure 16A:
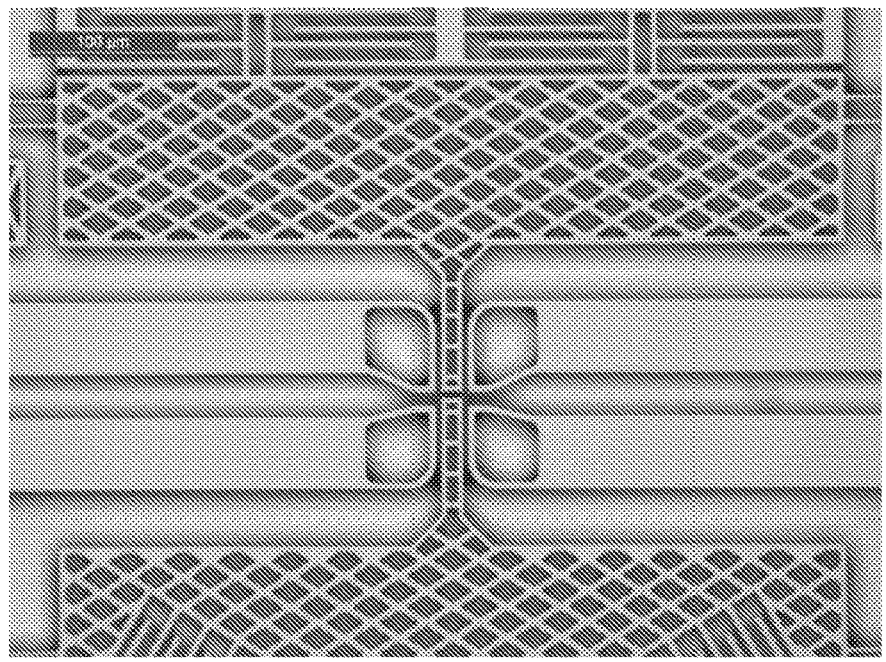
FIGS. 16A and 16B illustrate etched high-aspect ratio features in silicon.
Figure 16B:
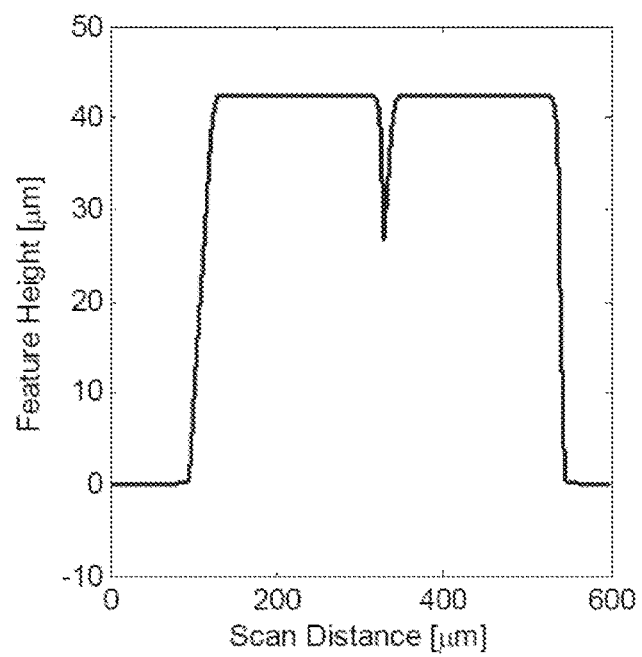

In certain embodiments the oscillator and sensor can be integrated into a single component. Unlike the architecture in FIG. 15, panel A, and FIG. 17, panel A, in which the probe and sensor are on opposite sides of the channel, illustrative designs in which the oscillator and sensor are integrated into one body are shown in FIG. 15, panel B, FIG. 18 (design A3), panel a, and FIG. 19, panel B (design A6). Results produced by etch mask shown in 15, panel A, are illustrated in FIG. 16).

In the integrated oscillator/sensor embodiments, instead of measuring the force transmitted through a cell, a measure is made of how much a passaging cell disrupts the normal oscillation pattern that is driven by the oscillator drive signal. The position pattern can be measured by the integrated sensor and the fundamental frequency components of the output signal can be analyzed with data acquisition software. In certain embodiments measurement of oscillatory patterns can be performed by either a phase-lock amplifier or wavelet analysis.

Many equally valid probe shapes at the cell probe interface can be designed. In certain embodiments a slightly concave, but fairly flat, design was chosen, but the devices described herein need not be limited to such a shape.

Figure 20A:
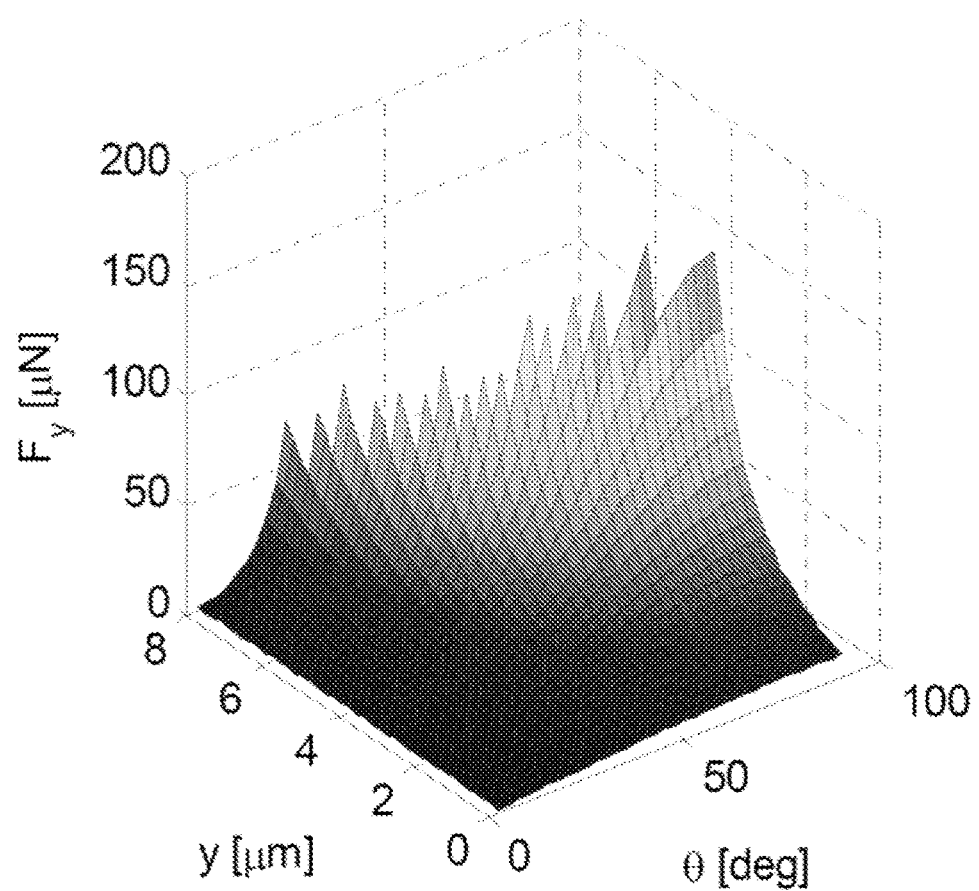
FIGS. 20A and 20B illustrate an analysis of force achievable from a comb drive array at different comb angles. A θ=0° orientation is equivalent to the longitudinal orientation and 90° is the latitudinal orientation. We chose a 30° orientation because it is capable of twice the displacement of the 90 deg, but also achieves many multiples more force than a 0 deg design for across the displacement range (y-axis).
Figure 20B:
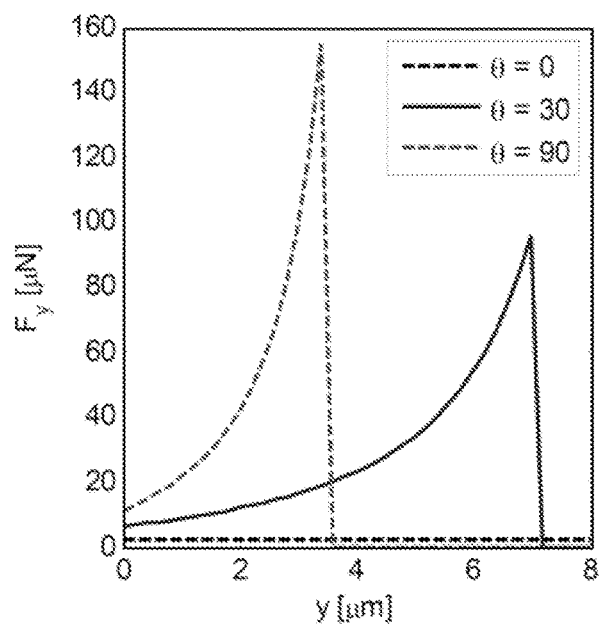

In addition, comb angle can be varied. In certain embodiments a 30 degree angle for oscillator combs and a 90 degree angle for the sensor combs is illustrated. These designs were chosen to provide the best performance for certain specific applications, but other comb orientations are feasible as well. These have been considered and analyses performed, see, e.g., FIGS. 20A and 20B.

In various embodiments the probe tip may be capable of other types of measurements or stimuli applied to cells. For instance, the impedance of a cell can also be measured when the probe is contacting the cell. Cell impedance has been used for classifying cell type, providing an extra detection function (Chen, et al. (2011) *Lab on a Chip,* 11: 3174-3181). In certain embodiments of the MaPS devices described herein, the moving bodies are grounded and are made of doped (electrically conductive) silicon. However, there are lithographic methods to selectively dope silicon to reduce electrical impedance along certain pathways. The manufacturing protocols described herein can incorporate the selective doping of undoped silicon wafers to direct electrical signals and permit probing of the impedance of cells. Also, metallic layers can be added to the silicon surface to direct electrical signals. Almost identically, except using higher voltage differences, individual cells can be electroporated to increase the electrical conductivity and permeability of the cells. MaPS provides be a more efficient method to electroporate selected individual cells than current technologies (Khine, et al. (2005) *Lab on a Chip,* 5: 38-43).

Figure 24A:
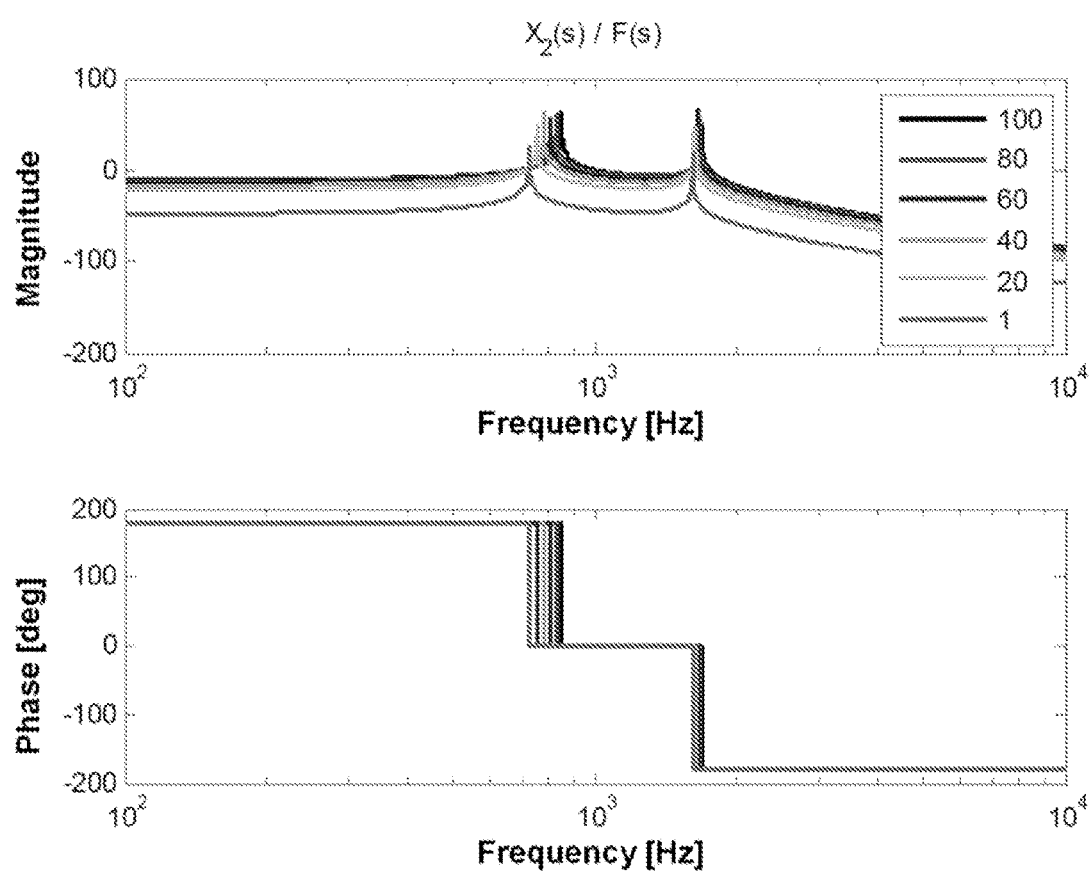
FIGS. 24A and 24B illustrate representative frequency response plots of comb drive system (Magnitude in dB). This plot provides frequency response between the electrostatic forcing signal and the position of the sensor probe for varying cell moduli. 100% is a healthy cell and the different level sets are percentages of the healthy moduli.
Figure 24B:
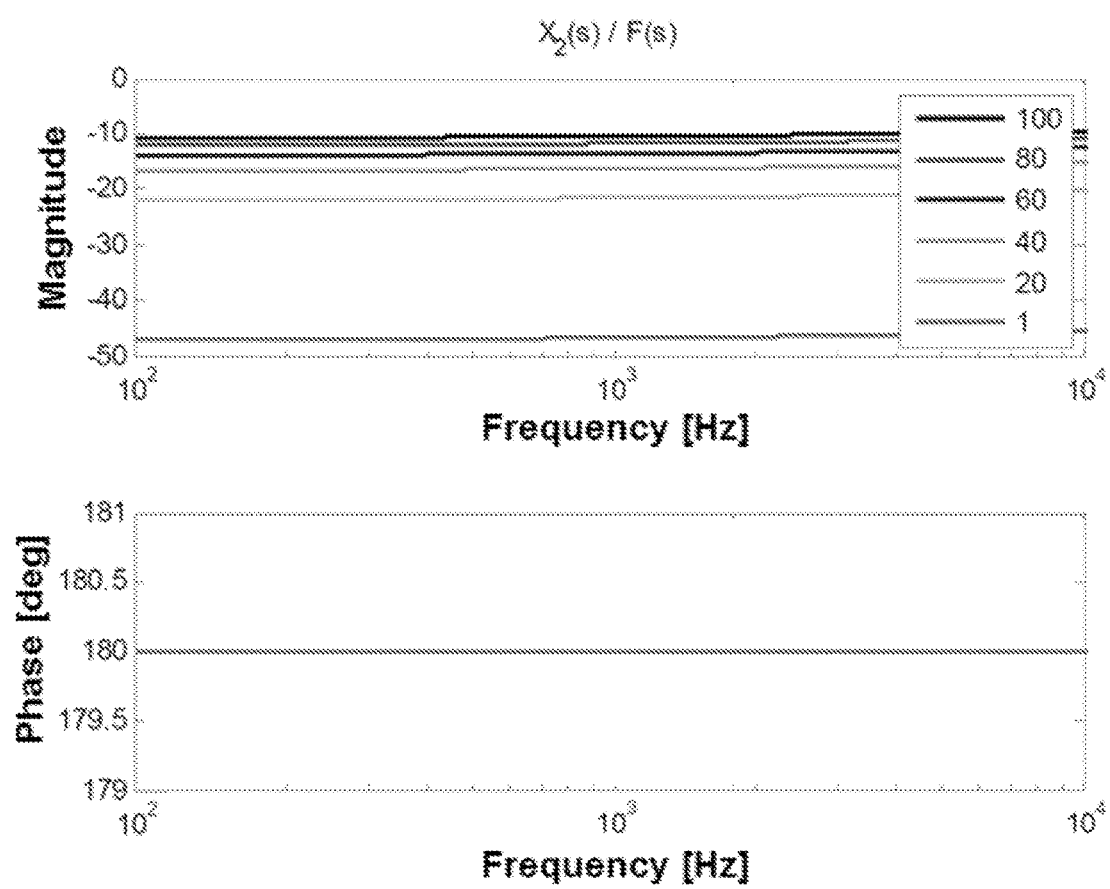

The stated frequencies of ~400 Hz for the main driving signal and 0.5 MHz for the carrier frequency reflect effective starting values. It is recognized that these may vary. Frequency simulations of the device predict that a main driving signal in the range of 200 Hz to 700 Hz is feasible and a frequency of over $10^4$ Hz for the carrier frequency will permit actuation in aqueous media and not affect the movement of mechanical components, see frequency analysis in FIG. 24 and Table 1.

TABLE 1

Design set and simulated output values.

| Design # | $K_1$ (Nm$^{-1}$) | $K_2$ (Nm$^{-1}$) | N comb fingers | Stratification (100-1%) (μm) |
| --- | --- | --- | --- | --- |
| A1 | 1 | 0.2 | 30 | 0.2846 |
| A2 | 1 | 0.2 | 20 | 0.2846 |
| A3 | 0.5 | — | 20 | 0.294 |
| A4 | 0.8 | 0.2 | 30 | 0.3506 |
| A5 | 0.8 | 0.2 | 20 | 0.3506 |
| A6 | 0.35 | — | 20 | 0.566 |

In addition, the description of a driving frequencies, described above, e.g., ~400 Hz assumes a sinusoidal signal shape. Other driving signal shapes are contemplated. For instance, since the attraction forces are nonlinear it may be advantageous to compensate for this nonlinear behavior by having a nonregular, but periodic signal shape, using the inverse dynamics. FEA measurements of the position dependent force have been determined for the purpose of developing a proper driving signal shape. In certain embodiments a dual mode probing waveform (shape) can be used opposed to just a single sinusoidal driving signal. This could be used to probe alternating depths at alternating cycles. This would be a compound sinusoid where the 400 Hz driving signal would probe to one depth on one cycle and another depth on the next cycle, then repeat. While, in certain embodiments DI water is used as the low ionic content fluid to immerse the drive electronics. In certain embodiments non-aqueous options are available. Such options include, but are not limited to oils and solvents.

The foregoing variants are intended to be illustrative, but non-limiting. Using the teaching provided herein, numerous other configurations, materials, and modes of operation will be available ton one of skill in the art without undue experimentation.

Other Illustrative Uses

MaPS has the potential to become a versatile tool that plays a transformative role in mechanical phenotyping. MaPS can perform quantitative, high-throughput assessment of mechanical phenotypes with unprecedented throughput and efficiency. It is believed that MaPS will open up new avenues to exploit mechanical phenotyping for combinatorial screening of treatments from both drug and natural compound libraries, as well as microRNAs. Since the degree of invasiveness of human ovarian cancer cell manifests in changes in the cellular mechanical phenotype (Swaminathan et al. (2012) *Cancer Res.* 71(15): 5075-5080), MaPS should has the potential to screen based on the metastatic efficiency of cells. Furthermore, MaPS has potential to reveal heterogeneity among the mechanical properties of individual cells within a large population and possible functional implications (Calbo, et al. (2011) *Cancer Cell,* 19: 244-256). A similar transformation emerged with the advent of flow cytometry and FACS, which the evaluation of large numbers of individual cells, and variability within a population. Such studies will provide insights into the genetic and epigenetic origins of heterogeneity within a population of cancer cells, including drug resistance as well as prognostic stratification. Moreover, MaPS is well poised to be equipped with the ability to sort cells based on mechanical phenotype, thus enabling experiments on subpopulations of cells, for example, that display drug resistance; such high throughput functionality is unrealizable in current mechanical phenotyping technologies.

The foregoing uses and embodiments are illustrative and not limiting. For example, while the one application described above is the phenotyping of cell mechanics and sorting based on this criteria, other applications include, but are not limited to, microparticle characterization and sorting, microbial or plant cell characterization, fluid viscosity measurements, and the like. In various embodiments characterization may be based on mechanical, electrical, physical properties, and the like.

Additional illustrative, but non-limiting applications include the following: For example. MAPs can be used to evaluate radiation exposure. The mechanical properties of white blood cells altered upon exposure to gamma irradiation (see, e.g., Selim et al. (2009) *Romanian J. Biophys.,* 19: 171-185). Monitoring the mechanical properties of blood cells using MaPs can provide a label-free method to detect magnitude and time since exposure. Similarly, changes in mechanical properties of red blood cells occur with Diabetes mellitus (see, e.g., Goldstein et al. (2004) *Graefes Arch. Clin. Exp. Ophthalmol.* 242: 937-943; Cho et al. (2008) *J. Diabetes Sci. Technol.,* 2: 1130-1138; Mantskava et al. (2006) *Clin. Hemorheol. Microcirc.* 35: 307-310; Singh and Shin (2009) *Indian J. Exp. Biol.* 47: 7-15). It is believed that MaPS can thus be used as a screening tool for screening for diabetes. MaPS also provides a means to detect and isolate stem cells. High quality stem cells are essential for therapeutic applications. Pluripotent stem cells can be distinguished from differentiated cells by their mechanical properties (see, e.g., Gossett et al. (2012) *Proc. Natl. Acad. Sci. USA,* 109: 7630-7635; Engler et al. (2006) *Cell,* 126: 677-689; Pajerowski et al. (2007) *Proc. Natl. Acad. Sci. USA,* 104: 15619-15624) and MaPS can be used to detect these differences.

Changes in the mechanical properties of red blood cells occur upon *Plasmodium falciparum* infection (see, e.g., Marinkovic et al. (2009) *Am. J. Physiol. Cell* Physiol. 296: C59-64). MaPS can thus be thus be used to screen for malaria, with the potential to identify early stage infections.

Decreased deformability of red blood cells occurs with sickle cell disease (see, e.g., Higgins et al. (2007) *Proc. Natl. Acad. Sci. USA,* 104: 20496-20500). Mechanotyping using MaPS can provide a readout for screening gene therapy approaches that may prohibit stiffening of cells upon deoxygenation.

It is also believed that MaPS can be used to provide real-time cancer diagnosis in a clinical setting. For example, the mechanical compliance of individual cells can be used to determine the invasive potential of ovarian cancer cells (see, e.g., Xu et al. (2012) *PLoS One,* 7: e46609, 2012; Swaminathan et al. (2012) *Cancer Res.* 71: 5075-5080). Moreover, there are distinct differences in the mechanical properties of drug-resistant versus drug-sensitive variants of ovarian cancer (Lam et al. (2007) *Blood,* 109: 3505-3508). Distinguishing drug-resistant cancer subtypes is typically achieved by molecular (protein, gene expression) analysis. However, in many cases patients receive chemotherapy treatment they do not respond to; the resultant costs are high, both for the patients and for the healthcare system. MaPS can be used to identify such drug resistant cancer subtypes and modify therapeutic regimen accordingly.

With its real-time mechanotyping abilities, MaPS can be used to evaluate composition of human biopsies in a clinical setting. A major challenge during surgery is to insure the tumor has been cleanly removed, and that the border cells are not malignant. Atomic force microscopy reveals a distinct mechanical signature across a human breast biopsy sample, with the cancer cells in the interior being softer than the peripheral cells (see, e.g., Plodinec et al. (2012) *Nat. Nanotechnol.* 7: 757-765). MaPS can enable real-time analysis of biopsy samples that are dissociated into a suspension of single cells for guiding surgical decisions. Current methods typically rely on histology, proliferation, or biochemical analyses of cells.

In certain embodiments the MaPS systems described herein can be used in cancer treatment and drug screening. Alteration of mechanical properties upon treatment of cancer cells with drugs suggests the potential of mechanotyping to guide treatment decisions. For example, leukemia cells show a 10-fold increase in transit time? after treatment with chemotherapy agents (see, e.g., Lam et al. (2007) *Blood,* 109: 3505-3508). Recent results also show evidence of altered cell deformability upon overexpression of microRNA treatment. These results correlate with decreased cell proliferation as demonstrated by complementary assays. MaPS has potential to offer real-time mechanotyping that can provide complementary guidance towards treatment decisions in a clinical setting.

In certain embodiments it is believed the MaPS systems described herein can be used in the evaluation of Alzheimer's disease. Amyloid precursor protein (APP) is the precursor of beta amyloid, a peptide whose aggregation results in the formation of amyloid plaques that are found in the brains of Alzheimer's patients. Neuronal cells treated with amyloid-β42 (Aβ42) protein oligomers showed significant cellular stiffening, as determined by atomic force microscopy (see, e.g., Lulevich et al. (2010) *Proc. Natl. Acad. Sci. USA,* 107: 13872-13877). There is currently no good screen for effective treatments against Alzheimers. A high throughput method to screen cells could be used to identify compounds that prevent beta amyloid aggregation, or even the cleavage of APP which results in beta amyloid formation.

The MaPS systems described herein can be used in the design and formulation of drug delivery systems and in the quality control during manufacturing of such systems. Hydrogel microcapsules have been widely used for controlled delivery of drug therapeutics. Solute diffusion in a hydrogel depends on the degree of swelling of the hydrogel, which is a function of the polymer composition and cross-linking density/mesh size of the networks. For example, stiffer chitosan coated microcapsules show lower drug release rates (see, e.g., Veiga et al. (2011) *J. Appl. Polymer. Sci.,* 123(2): 842-849). Therefore mechanical characterization of hydrogel capsules using MaPS can be used to guide the design and formulation of drug delivery systems as well to monitor their quality during fabrication.

In addition to applications that involve measuring cell stiffness/deformability, the MaPs devices described here can also be used to directly manipulate single cells. In certain embodiments, the force probe (e.g., comb) can be used to displace objects, such as solid particles or liquids. For example, the well-controlled spatial oscillations of the probe can be applied to displace fluid and thereby sort cells. When the probe is placed just upstream from a junction in the fluid path (e.g., a Y-junction in a microfluidic channel), the perpendicular displacement of fluid, solid particle, or cell under flow could displace the object/fluid/cell into a separate channel. When activated in response to a given input condition, such a configuration could be used to actively sort particles or cells.

The MaPS devices can also be used for single cell electroporation. In certain embodiments, the fabrication protocol can be designed such that electrical lines are selectively doped within the silicon MEMS oscillator. This enables MaPS to both mechanically probe a cell and to impose an electric field to selectively electroporate cells. As analog signally pathways are fast in MEMS devices, the electric field can be selectively applied so that only some cells are electroporated, while the others are not. This allows allow biologist to artificially heterogenize a cell population.

In various embodiments the MaPS devices described here can be used for cell trapping. In certain embodiments, MaPS can be transitioned into a low-throughput device and the oscillator and sensor can be used as a cell trapping device that can facilely traps and releases cells. During entrapment, the cell could be briefly exposed to a stimuli. Reagent lines can be added to the larger MaPS architecture so as to deliver a metered dose of reagent to the trapped cell. This allow individual cells in a population to be given a metered dose. Thus, in certain embodiments, MaPS can be used to grade a population of cells with different reagent dosages. Other trapping embodiments could include extended mechanical tests to explore the creep and fatigue properties of a cell population.

The foregoing uses are intended to be illustrative and non-limiting. Using the teaching provided herein numerous other MaPS configurations and uses therefore will be available to one of skill in the art.

EXAMPLES

The following examples are offered to illustrate, but not to limit the claimed invention.

Example

Illustrative Embodiments

Figure 17:
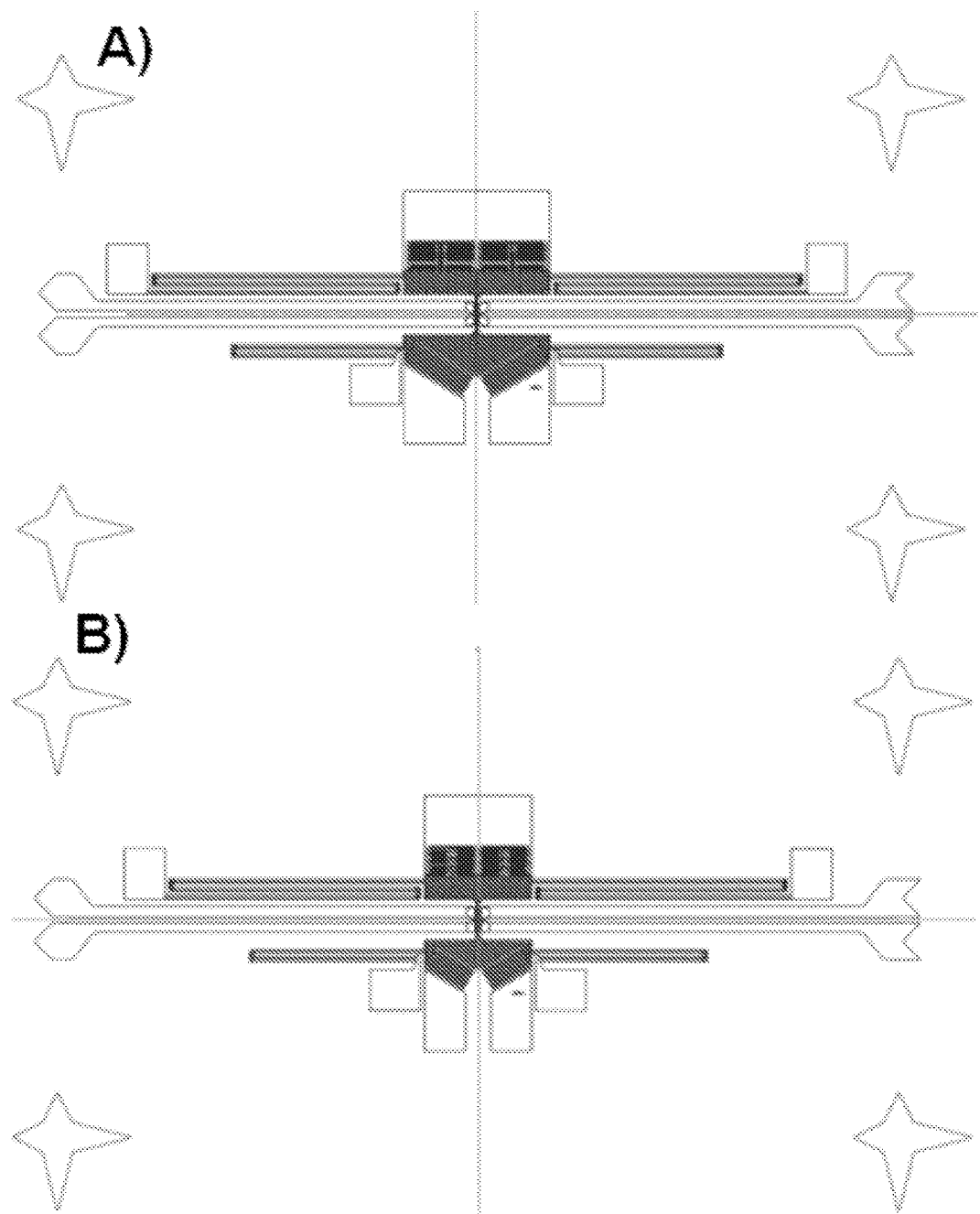
FIG. 17 illustrates MEMS device layer patterns for Designs A1 (panel a) and A2 (panel b).
Figure 18:
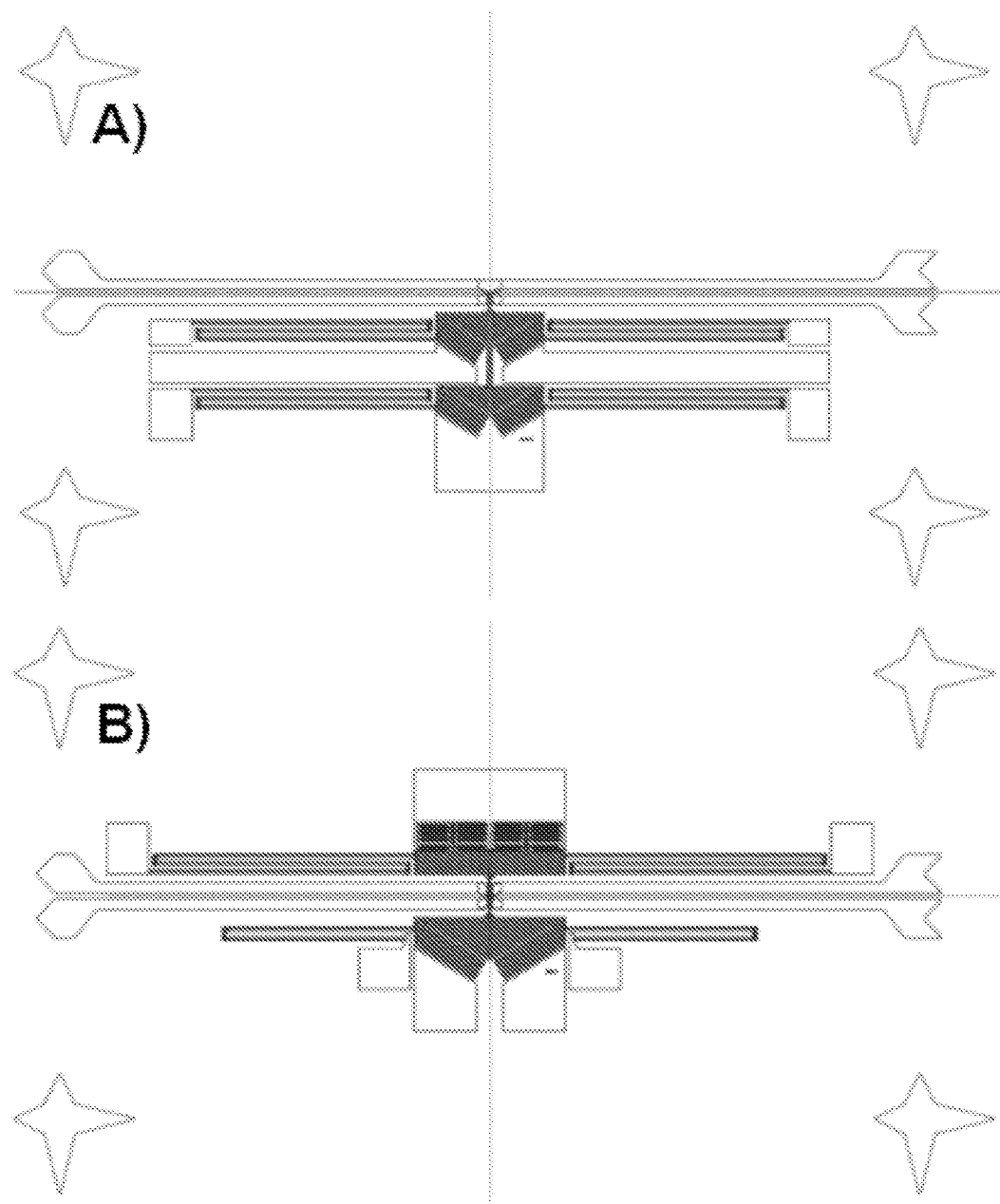
FIG. 18 illustrates MEMS device layer patterns for Designs A3 (panel a) and A4 (panel b).
Figure 19:
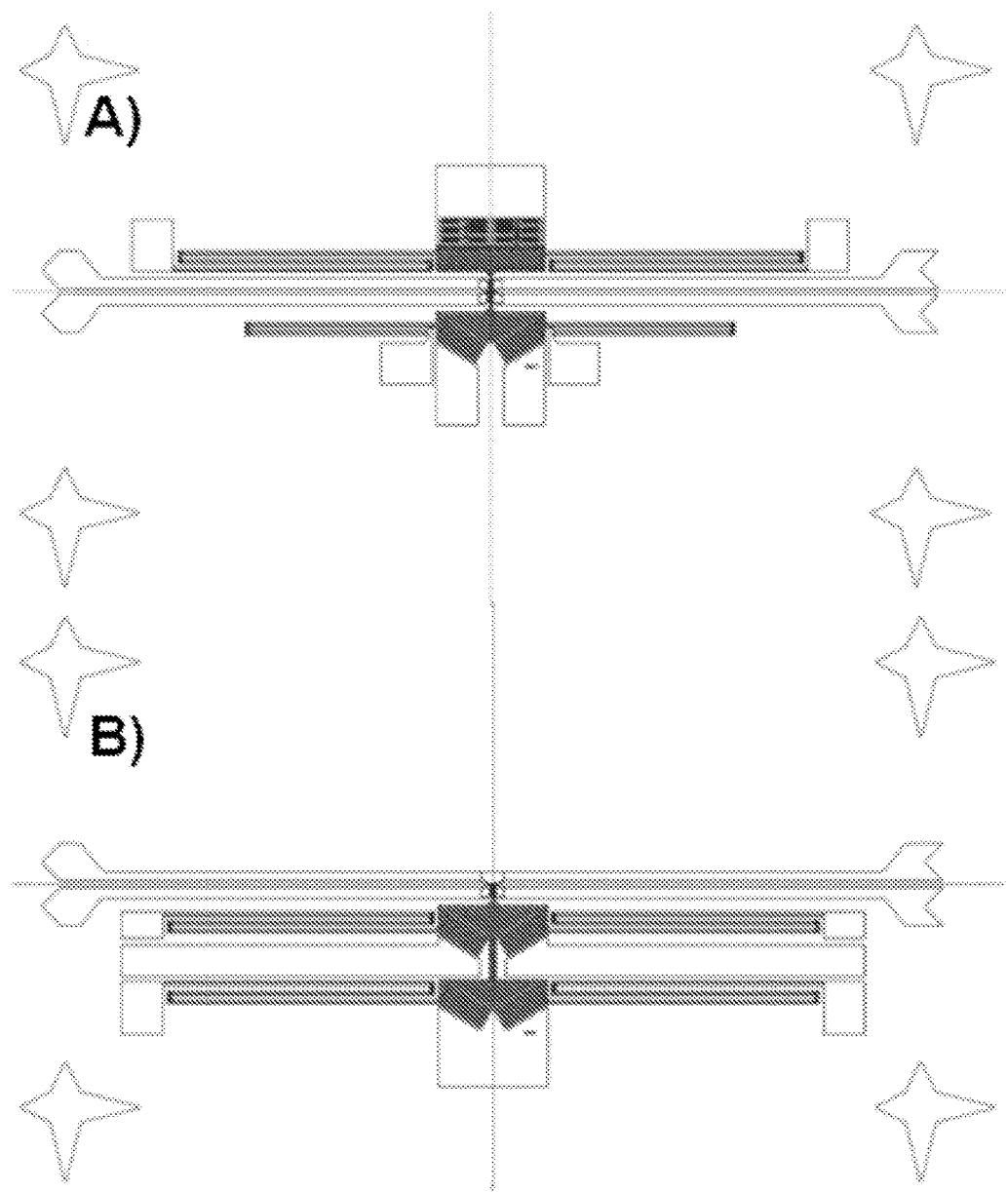
FIG. 19 illustrates MEMS device layer patterns for Designs A5 (panel a) and A6 (panel b).
Figure 21:
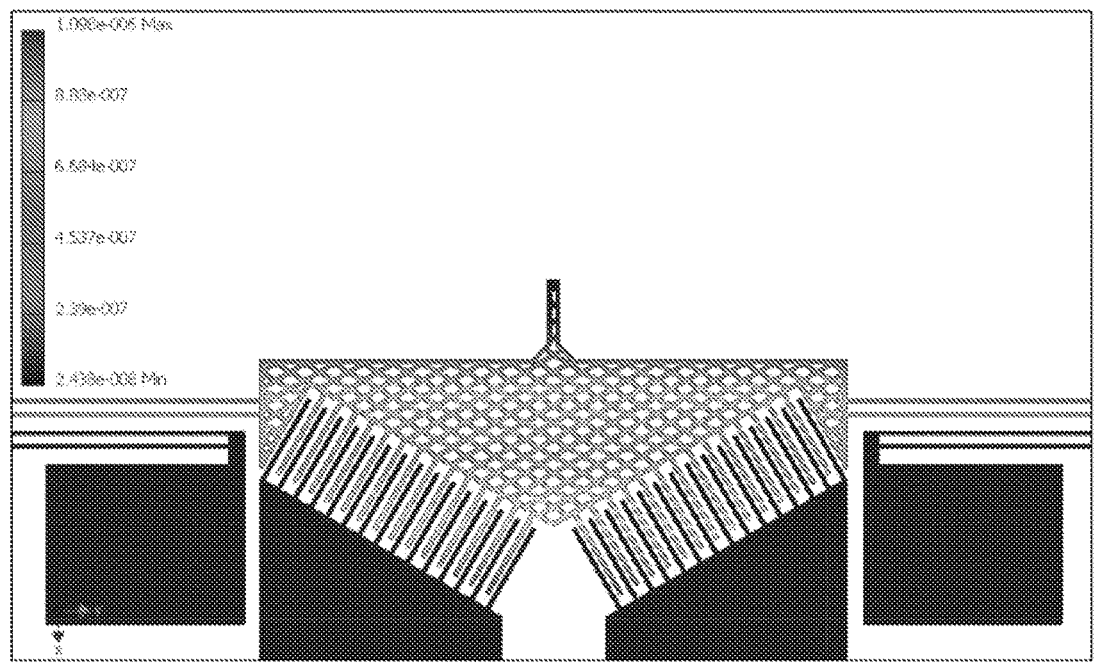
FIG. 21 shows the deflection from gravity of the oscillating probe (units mm). Maximum deflection is small (<50 nm) and will not detract from performance.
Figure 22:
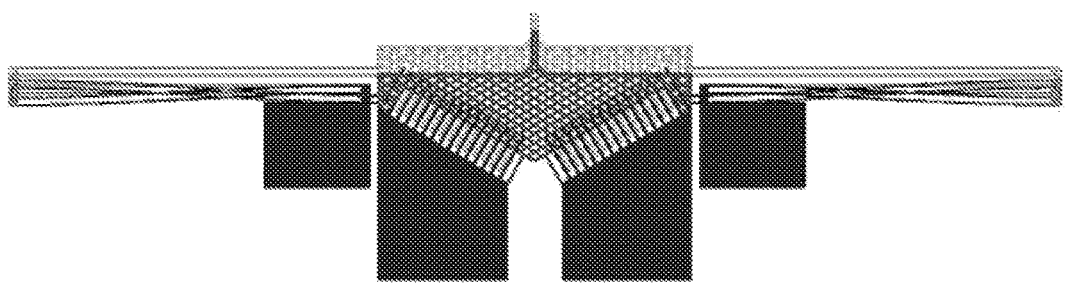
FIG. 22 shows the first resonant structural mode at 2641 Hz. This value, assessed by FEA, matches well with first principles analysis of the dynamics (data not shown). The system is typically not driven with a signal near 2600 Hz, so resonant modes are not excited.
Figure 23:
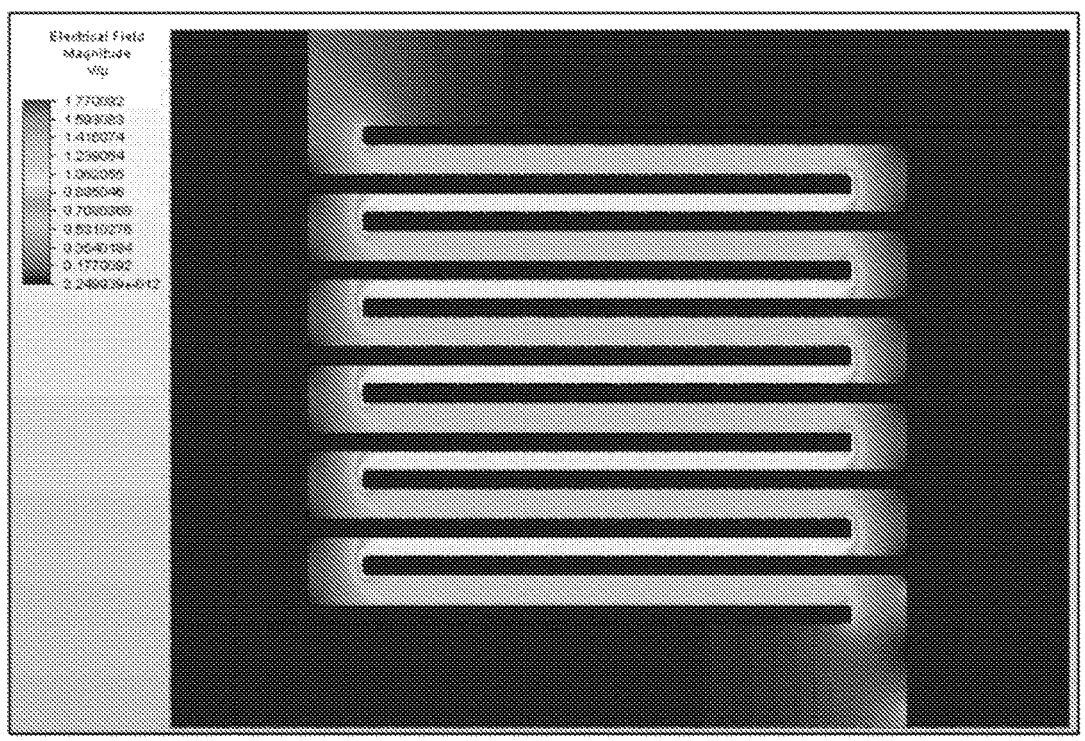
FIG. 23 illustrates electrostatic field strength between the fingers of a reduced size model comb drive system. Field strength decays as a cubic function, therefore close combs created a significantly larger field strength than combs that are just a little further away.
Figure 25:
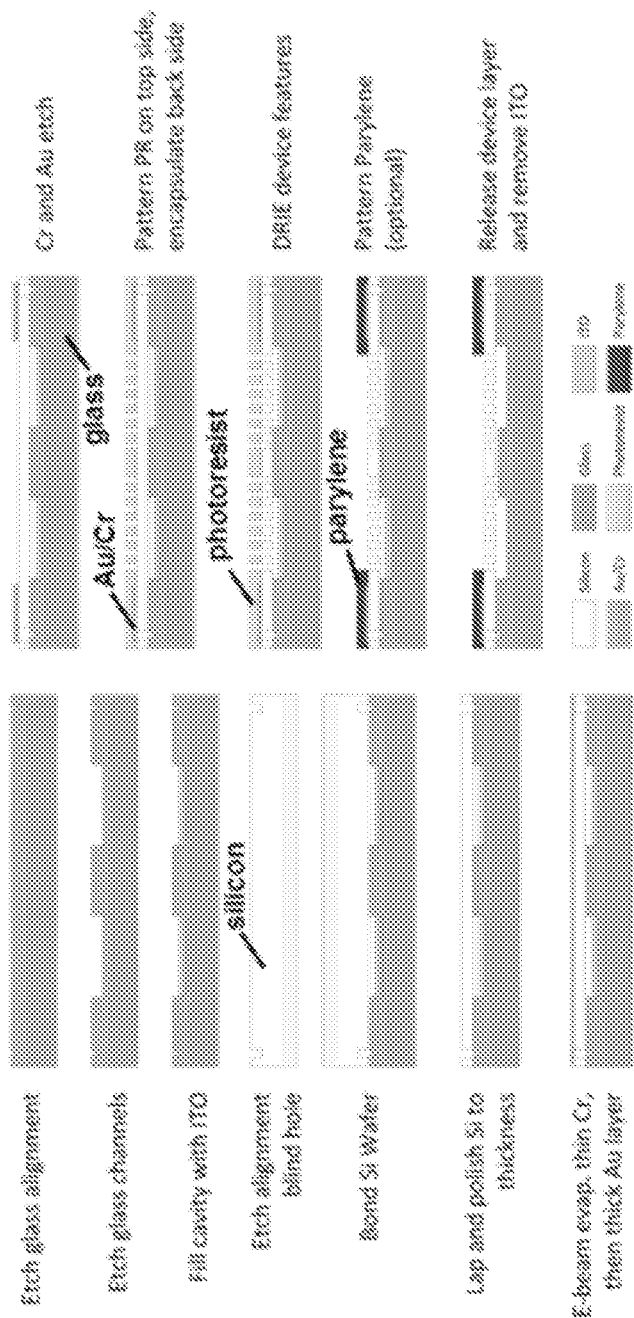
FIG. 25 illustrates one fabrication protocol for a MEMS device as described herein.
Figure 26:
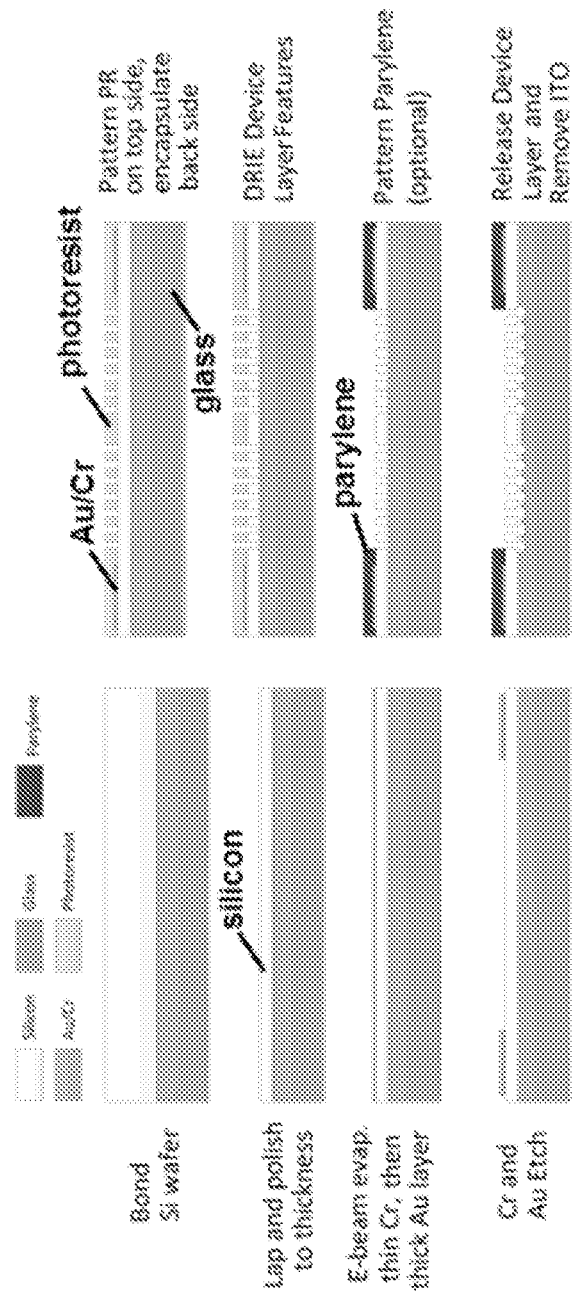
FIG. 26 illustrates a simplified fabrication protocol for a MEMS device as described herein. The simplified procedure does not have a channel etched into the glass substrate. In certain embodiments a channel in the glass can be provided to release the moving features of the MEMS device from the glass substrate (this would allow HF acid to move into the cavity and etch the glass/Si interface more quickly).

To expedite MaPS development, a set of six MEMS architectures were initially designed and designated A1 through A6 (see, e.g., FIGS. 17, 18, and 19). The set is designed to span a range of expected cell elastic moduli and to operate with slightly different dynamic ranges and sensor sensitivities. To characterize the static, dynamic, and electrical aspects of these MEMS device designs, finite element analysis (FEA) computer modeling was performed. These results provide further insight into the dynamic range and sensitivity of each device design, and also shed light on possible complications (see, e.g., FIGS. 21, 22, and 23). For example, it was determined that gravity will not deflect the force probe out of plane more than 50 nm (FIG. 21) and that structural resonances will not be excited at desired operating frequencies (FIG. 22). In addition to these simulations, a fabrication workflow for all six designs was formulated (see workflow options in FIGS. 25 and 26).

Example 2

Performance Evaluation

MEMS Finite Element Analysis

Figure 27:
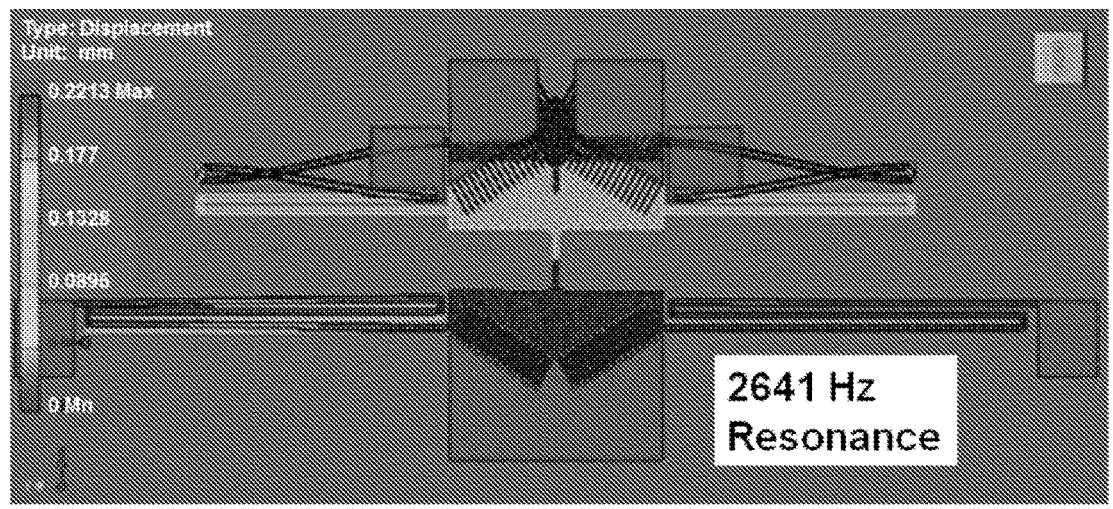
FIG. 27 illustrates FEA prediction of the first resonant mode of the oscillator (DV1).

Various MEMS component functions have been simulated using finite element analysis (FEA) models to predict MEMS properties. FEA calculations agree very well with first principles calculations of MEMS static and dynamic properties, giving confidence for future successful operation. By FEA, the spring constant of one embodiment of the oscillator and sensor are 0.993 N m$^{-1}$ and 0.205 N m$^{-1}$, respectively, whereas the values are 1 N m$^{-1}$ and 0.2 N m$^{-1}$ by first principles analysis. Dynamic FEA demonstrates that the first resonant mode was at 2641 Hz for the oscillator (see, e.g., FIG. 27). First principles analysis predicted 1887 Hz (DV1), which is considerably different from the FEA analysis, however, both resonance frequencies are considerably higher than the intended operation frequency of 500 Hz and therefore it is believed that resonance will not be an issue. Design version 2 is design to have a first resonant mode at 5970 Hz (by first principles analysis), which is even further away from the operating frequency.

Figure 28:
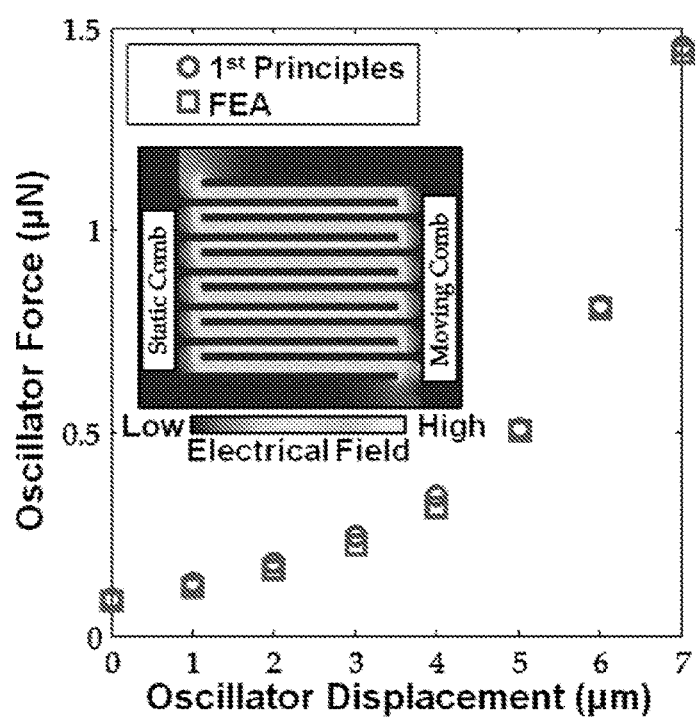
FIG. 28 illustrates first principles and corresponding FEA prediction of oscillator force as a function of oscillator position (DV1).
Figure 29:
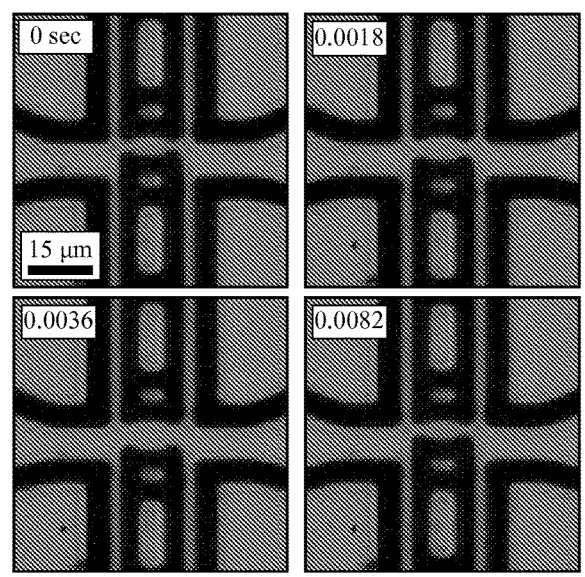
FIG. 29 shows the cycle of the MEMS oscillator at 128 Hz (DV1).

Electrostatic force FEA simulations agree very well with the first principles calculations of electrostatic force for the oscillator drive comb array (FIG. 28, Design variation 1). The relationship between electrostatic force, voltage potential across the comb members, and oscillator deflection is described by a nonlinear function. It is particularly important to ascertain the deflection at which the nonlinearity in the electrostatic force overcomes the linear force profile of the spring; beyond this deflection point the oscillator "pulls in" and does not release until the voltage potential is removed (Sun et al. (2002) Sensors and Actuators A, 102: 49-60). Given the strong agreement in models, it is possible to predict, and hence to prevent "pull in".

MEMS Oscillator Frequency Response

Figure 31:
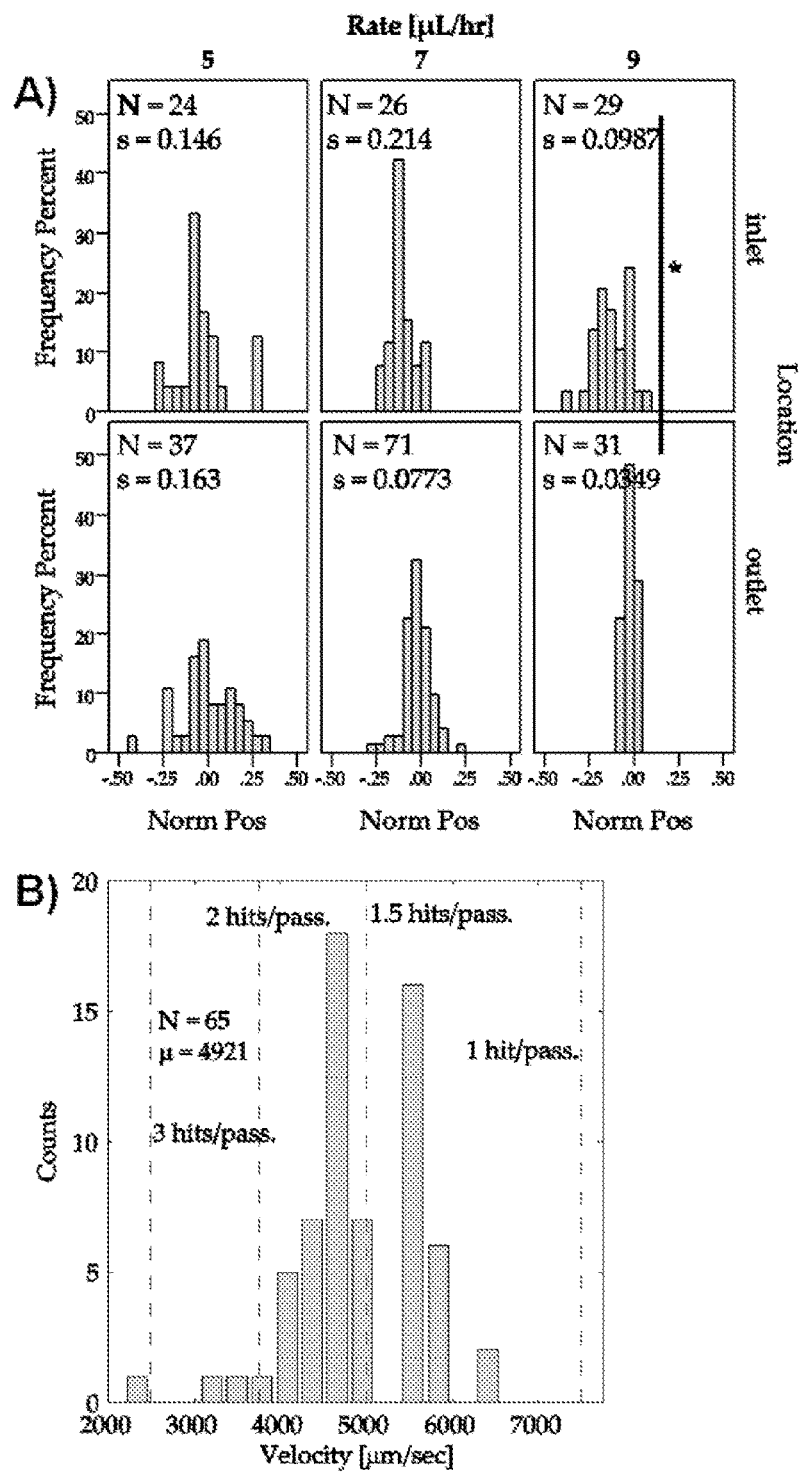
FIG. 31, panels A and B, illustrates data for a bypass array cell centering design. Panel A: Cell locations along the width of the channel at in the inlet and outlet of the bypass array for different flow rates. At 9 μL/hr the distribution narrows considerably (N=sample size; s=standard deviation). Statistically significant differences in standard deviation denoted by *; p<0.05 by Levine's test. Panel B: Measured cell velocity. The average cell will receive 1.5 oscillator hits per passage; mean μ=4921 μm/sec.

The MEMS oscillator side is actuated by applying the voltage signal given in Eq. 1.1 for a range of frequencies $f=2\pi\omega$ and a constant carrier frequency $f_c=2\pi\omega_c=500$ kHz. The fundamental frequencies are $f=2\pi\omega=[1, 1.41, 2, \ldots, 4096]$. To best emulate the microfluidic environment, the MEMS device was first wetted in methanol (methanol has less than half the surface tension of water) and then flushed with DI water so that the device was completely submerged in a well of DI water. FIG. 31 demonstrates one cycle of the oscillator when the system is driven at a fundamental frequency of 128 Hz as captured by a high-speed camera (Phantom MiroEX1, Vision Research, Wayne, N.J.) mounted to an inverted microscope port.

Figure 30:
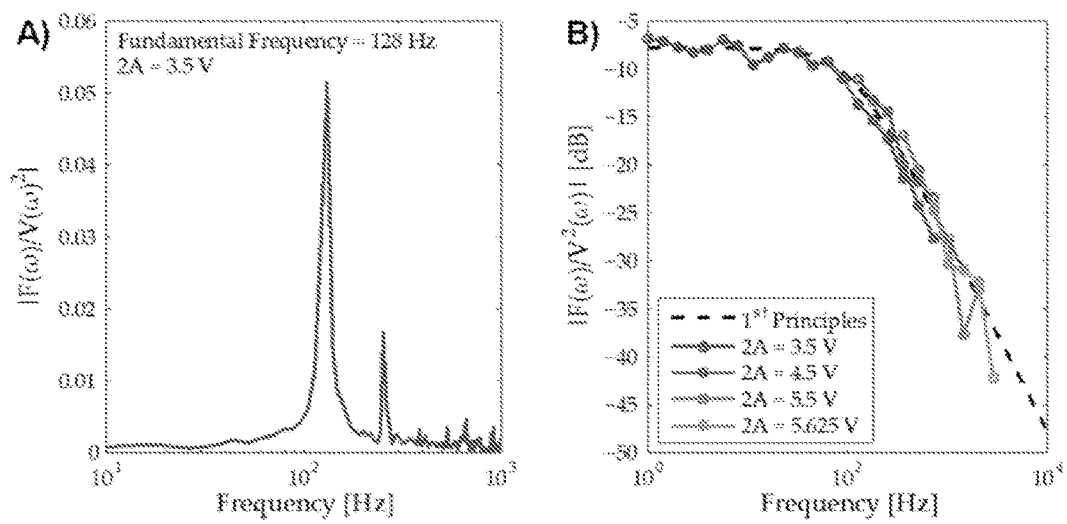
FIG. 30, panels A and B, show MEMS oscillator frequency response data (DV1). Panel A: Fourier transform of the time signal acquired for a fundamental driving frequency of 128 Hz with a sinusoid amplitude of 2 A=3.5 V. Panel B: Magnitude of the maximal frequency component of Fourier transform of each fundamental frequency tested. Data normalized by $F(\omega) \propto V^2(\omega)$. The system is very linear, as evidenced by the data for all operating magnitudes being parameterized by a single curve.

Time traces of the position of the oscillator are extracted from the high-speed video of the frequency experiments using a custom image correlation program. This program provides the position of the oscillator in pixels as a function of time. From this time signal, basic signal processing tools—namely the fast Fourier transform—are applied to decompose the movements into corresponding frequency components (FIG. 30B). The magnitude of the frequency components for each fundamental frequency tested are plotted as a function of fundamental frequency (FIG. 30A). The magnitude is normalized by $A^2$ since the driving electrostatic force is proportional to $A^2$. The oscillator frequency response is typical of an over-damped second-order system. The data corresponds well to a first principles model of a mass-spring-damper system with parameter: mass=4.75×10$^{-9}$ kg; damping coefficient=0.8×10$^{-3}$ N sec m$^{-1}$; and spring constant=0.8 N m$^{-1}$. From the principles of system theory, the oscillator responds "perfectly" without phase lag to input signals below 100 Hz and then the magnitude of the response decreases and the phase lags for the driving frequencies above 100 Hz. We were able to achieve full displacement oscillations for fundamental frequencies up to 512 Hz by increasing the driving sinusoid magnitude to 2 A=5.625 V.

Cell Centering in the Cell Media Channel

Ideally, the stream of cells entering the probe interface location of MaPS will be centered within the width of the channel and evenly spaced along the length of the channel. Note, however, that the cell media channel constrict immediately before the probe interface to consistently deliver cells to the probe location; although it is unclear whether "back-end" centering must be performed. A variety of different 'back-end' cell centering channels have been tested experimentally. A multiple bypass channel design, as depicted in FIG. 8B, effectively forces a cells towards the center of the channel width. Cells entering the bypass array have a fairly uniform distribution of their position along the width the channel (FIG. 31A). During the 3000 μm pass from inlet to outlet, the distribution sharpens and the cells are effectively centered along the width (FIG. 31A). The centering performance increases with flow rate and is expected to operate near the highest flowrate tested—9 μL/hr. Data was acquired through flow test operated on an inverted microscope with a high-speed camera (Phantom MiroEX1, Vision Research, Wayne, N.J.) recording cell position along the width of the channel at the inlet and outlet of the bypass array. Another consideration is the velocity of the passaging cells. For a given oscillator frequency, there is an inverse relationship between the number of times that the oscillator contacts the cell and the velocity of the cell. We have measured the velocity of passaging cells using the same inverted microscope/camera setup. At a 500 Hz oscillator frequency and a media flowrate of 9 μL/hr, we predict that all cells will be probed at least one time by the oscillator, and the average cell will be probed 1.5-2 times by the oscillator (FIG. 31B).

MEMS Component Designs for Design Version 2

Figure 32:
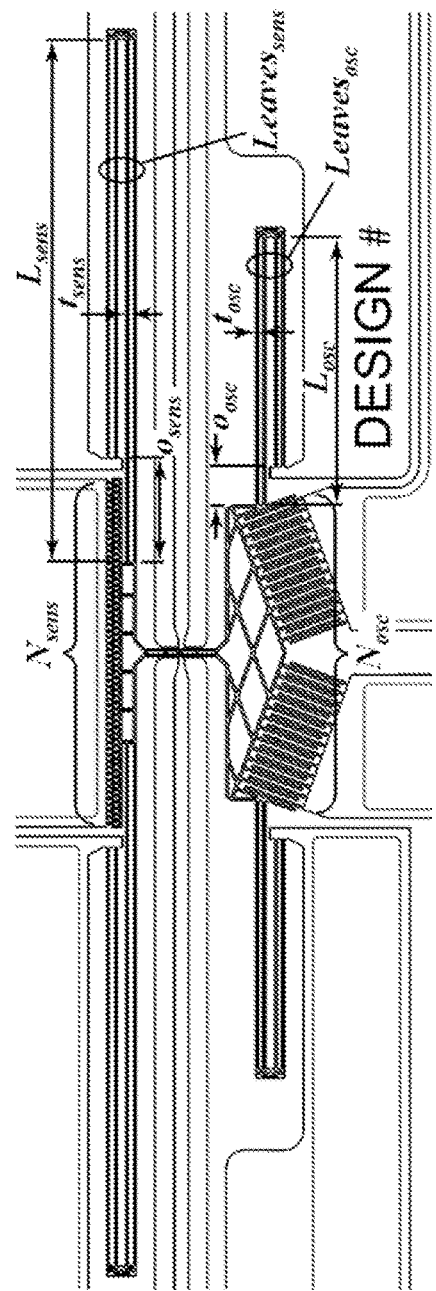
FIG. 32 illustrates various design parameters used to achieve a range of Sensor sensitivities and sensing capacitances. Dimensions for each design are given in Table 2. Note the parameter "Leaves" specifies the number of leaves (beam pairs) per side for either the oscillator or sensor. In the illustrated example both the oscillator and sensor have 2 leaves per side. Design B5 has three leaves for the sensor.

FIG. 8 demonstrates a complete MEMS device with large contact pads to interface with an electrical system on the macroscale. FIG. 32 illustrates the parameters designs B1-B5 (of design version 2). Properties of each design are given in Table 2.

TABLE 2

Illustrative design parameters for design version 2 (see FIG. 32).

| Design # | $k_1$ (N m$^{-1}$) | $k_2$ (N m$^{-1}$) | N (finger pairs) (osc/sens) | L (μm) (osc/sens) | O (offset, μm) (osc/sens) | t (μm) (osc/sens) | Leaves (osc/sens) |
|---|---|---|---|---|---|---|---|
| B1 | 10 | 0.50 | 26/114 | 563/1098 | 80/218.16 | 5/3.5 | 2/2 |
| B2 | 10 | 0.50 | 26/74 | 563/1044 | 80/91.9 | 5/3.5 | 2/2 |
| B3 | 10 | 0.80 | 26/114 | 563/951 | 80/218.16 | 5/3.5 | 2/2 |
| B4 | 10 | 0.80 | 26/74 | 563/899 | 80/91.9 | 5/3.5 | 2/2 |
| B5 | 10 | 0.20 | 26/74 | 563/1227 | 80/131.92 | 5/3.5 | 2/3 |

Figure 33:
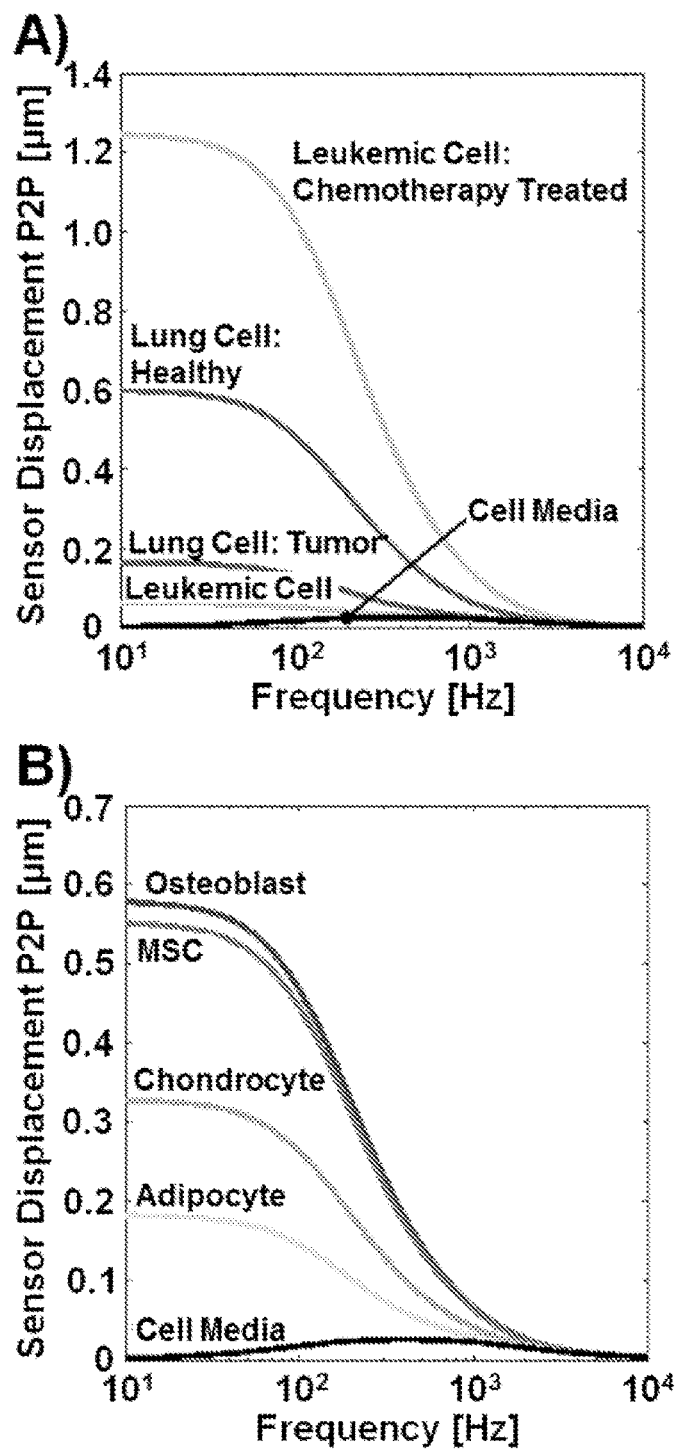
FIG. 33, panels A-C, illustrates candidate test materials and predicted sensor frequency responses. Panel A: Examples of cancerous test materials and expected sensor displacements. Panel B: MSCs and differentiated lineages. Panel C: Polymeric test materials. Note that that the y-axis is on a log scale in panel C. Sources for a-c are in Table 3.

Simulations of the Frequency Response of MAPS for Select Biological and Material Characterizations Candidate test materials and predicted sensor frequency responses are shown in FIG. 33. Model parameters for frequency response simulations are shown in Table 3.

TABLE 3

Model parameters for frequency response simulations

| Param. | Value | Units | Notes |
|---|---|---|---|
| $m_1$ | $3.40 \times 10^{-9}$ | kg | Assume Si density of 2.33 g cm$^{-3}$ |
| $m_2$ | $1.23 \times 10^{-9}$ | kg | Assume Si density of 2.33 g cm$^{-3}$ |
| $b_1$ | $1.25 \times 10^{-3}$ | N sec m$^{-1}$ | Empirical Estimate |
| $b_2$ | $0.625 \times 10^{-3}$ | N sec m$^{-1}$ | Empirical Estimate |
| $b_c$ | $2.00 \times 10^{-6}$ | N sec m$^{-1}$ | — |
| $k_1$ | 10 | N m$^{-1}$ | Assume Si modulus of 130 Gpa |
| $k_2$ | 0.5 | N m$^{-1}$ | Assume Si modulus of 130 Gpa |
| $k_c$ (Human Lung - Normal) | 0.0359 | N m$^{-1}$ | 2.075 kPa; assume Hertz model |
| $k_c$ (Human Lung - Tumor) | 0.00933 | N m$^{-1}$ | 0.54 kPa; assume Hertz model |
| $k_c$ (Human Leukemia - Mean - Chemo Treated) | 0.0812 | N m$^{-1}$ | 4.7 kPa; assume Hertz model |
| $k_c$ (Human Leukemia - Mean) | 0.00346 | N m$^{-1}$ | 0.2 kPa; assume Hertz model |
| $k_c$ (MSC) | 0.0328 | N m$^{-1}$ | 1.9 kPa; assume Hertz model |
| $k_c$ (Adipocyte) | 0.0104 | N m$^{-1}$ | 0.61 kPa; assume Hertz model |
| $k_c$ (Chondrocyte) | 0.019 | N m$^{-1}$ | 1.1 kPa; assume Hertz model |
| $k_c$ (Osteoblast) | 0.0346 | N m$^{-1}$ | 2.00 kPa; assume Hertz model |
| $k_c$ (3% polyacrylimide) | 0.00346 | N m$^{-1}$ | 0.2 kPa; assume Hertz model |
| $k_c$ (5% polyacrylimide) | 0.151 | N m$^{-1}$ | 8.73 kPa; assume Hertz model |
| $k_c$ (10% polyacrylimide) | 0.603 | N m$^{-1}$ | 34.88 kPa; assume Hertz model |
| $k_c$ (polystyrene) | $51.84 \times 10^3$ | N m$^{-1}$ | 3 GPa; assume Hertz model |

Example 3

A Large-Displacement, High-Frequency In-Situ Underwater MEMS Oscillator

I. Introduction.

The past two decades have brought a wealth of scientific studies of microsystems utilized to characterize and recapitulate native microenvironments. Although large in scope, we focus the discussion on mechanisms that actively impose forces at the microscale. These methods have uncovered important biological phenomena; probing the mechanical constituency of intracellular organelles, observing the physical and chemical responses to mechanical stimuli, and revealing the biomechanical signature of the malignant transformation of cancerous cells, to name a few. Also, active mechanisms have been utilized to route cells and lysed intracellular constituents for characterization by biochemical means by actively changing the flow patterns within massively parallel microfluidic networks.

One trend is towards faster, parallelized characterization and manipulation in an aqueous environment. However, typically the interacting surfaces (e.g. probe tips, syringe tips, laser spots) are of the microscale, but the supporting infrastructure is of the meso- to macroscale. A key example is atomic force microscopy (AFM) which has a nanoscale probe capable of exquisitely mapping cell topography, but is driven by a mesoscale piezo-actuator and is therefore incapable of being efficiently multiplexed throughout a parallelized network of actuators as the actuator has a large footprint. AFMs are of a class actuators that we term ex situ actuators that includes, inter alia, piezo-horns for surface acoustic wave generation, optical tweezers systems for particle positioning, and micromanipulators to position micropipettes and probes, and the like.

In situ actuators comprise a class of actuators that have a moving surface or force generated at or near the point of contact. These actuators are typically powered by a large, mesoscale source (such as an electrical or pressure source). However, intra-device vias can deliver energy to the in-situ actuator at the point of contact and hence multiple, parallelized actuators can be integrated into an actuator network. Quake style valves exemplify in-situ actuation, integrating hundreds of valves within a single microfluidic device. Other examples include electrostatic and thermal actuators.

This Example investigates electrostatic in situ actuation in an aqueous environment. Previous researchers have identified electrical signaling schemes to actuate underwater electrostatic actuators without electrolyzing water or suffering from charge shielding affects, however the designs focused on static deflections. We envision high-speed electrostatic actuators integrated in a massively parallel architecture within microfluidic devices. Hence, this investigative study synthesizes an optimal actuator architecture for large-displacement (>5 μm), high-frequency (>1 kHz) actuation within a compact footprint; to the best of our knowledge these characteristics have not been demonstrated.

The full utility of such actuators is still in its infancy. This example presents a study into underwater oscillator actuation. Viscous damping is large in an aqueous environment, as compared to actuation in air or vacuum, and the standard physics tools for actuator design in low-viscosity conditions do not apply for underwater actuators. Accordingly, new mathematical methods for analyzing and predicting performance are presented. Electrostatic underwater low-frequency high-displacement actuation and high-frequency low-displacement actuation are each readily achievable. To achieve high-displacement and high-frequencies, a novel angled comb drive was leveraged and optimized. Optimization considered over 6000 different design options to predict performance. The developed mathematical methods provide a facile tool for design iteration. We demonstrate the actual design, achieving a maximum displacement of over 9 μm at a frequency of 1 kHz.

II. Design.

An electrostatic force is generated when two surfaces at different electrical potentials are placed in proximity to each other. Designed microsystems exploit electrostatic forces to generate modulable movements at the microscale by controlling an applied voltage signal. Electrostatic force, F(X(t), V(t)), is a function of electrode gap, x(t), and applied voltage, V(t). Underwater, two deleterious effects preclude utility: electrolysis of water due to the voltage difference and charge shielding from the water molecules polarizing, hence shielding electrostatic forces.

Figure 34:
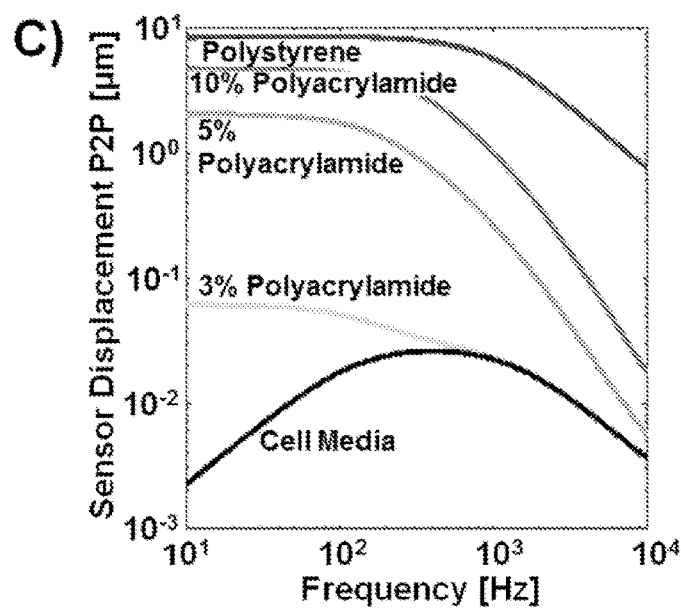
FIG. 34 illustrates an amplitude modulated cosine wave with a pulse function carrier wave.
Figure 34:
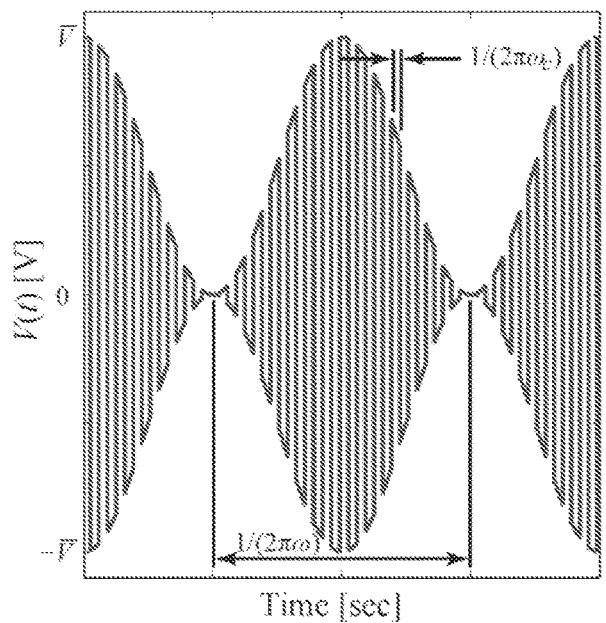

Electrolysis will occur at voltages approximately greater than about 8V and thus constrains the applied voltage. Charge shielding can be effectively obviated using a signaling scheme that flips the electrode polarity faster than water molecules reorient. An amplitude modulated signaling scheme (FIG. 34) in which the fundamental signal is within the bandwidth of the actuator, but has a carrier signal that is well above the bandwidth of the actuator and water molecules, permits the fundamental signal to be applied in an aqueous environment. For simple actuator designs, the position and voltage dependent components of the electrostatic force function are separable:

$$F(x(t), t) = f(x)V^2(t) \quad (1)$$

$$F(x(t), t) = f(x)\left(\frac{1}{2}\overline{V}(1+\cos\omega t \Pi t)\right)^2 = f(x)\overline{V}^2\left(\frac{3}{8} + \frac{1}{2}\cos\omega t + \frac{1}{8}\cos 2\omega t + H.F.T.\right)$$

where the voltage component is squared and the pulse function $$\Pi(t) = -\frac{4}{\Pi}\sum_{k=1}^{\infty}\frac{1}{2k-1}(-1)^k \cos\omega_c kt.$$

The pulse function yields an infinite sum of cosine functions at integer multiples of $\omega_c$ in when $\omega_c$ is chosen to be at a frequency that is three orders of magnitude larger than the bandwidth of the mechanical system. Hence these terms become an infinite sum of high frequency terms (H.F.T.) that are inconsequential to oscillator performance. Taken together, underwater actuation limits the maximum instantaneous voltage to approximately 8 V and enforces the use of an amplitude modulation signaling scheme.

A) Basic Dynamic and Static Mode
1) Linear Dynamic Model

Figure 35:
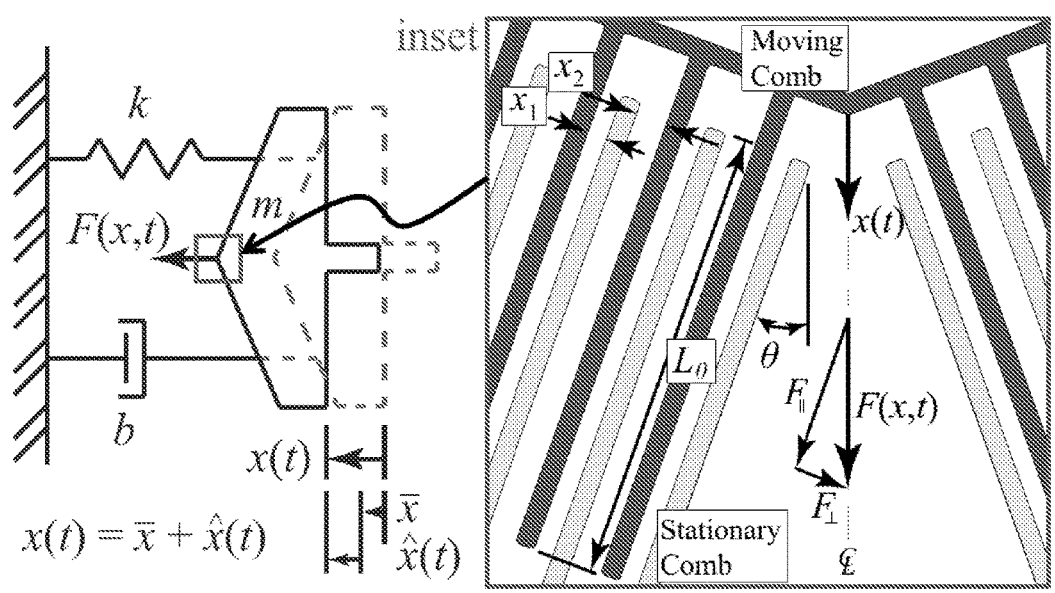
FIG. 35 illustrates a model of an angled comb drive in a viscous medium. The basic mass-spring-damper oscillator model is acted on by an exogenous electrostatic force. The electrostatic force F(x, t) is a function of time and position where the force is in the direction of the generalized coordinate x(t). F(x, t) is resolved from tangential F ∥ and perpendicular F ⊥ force components acting on the combs. The force perpendicular to F(x, t) is equal to zero in theory as the drive is symmetric about the centerline.
Figure 36A:
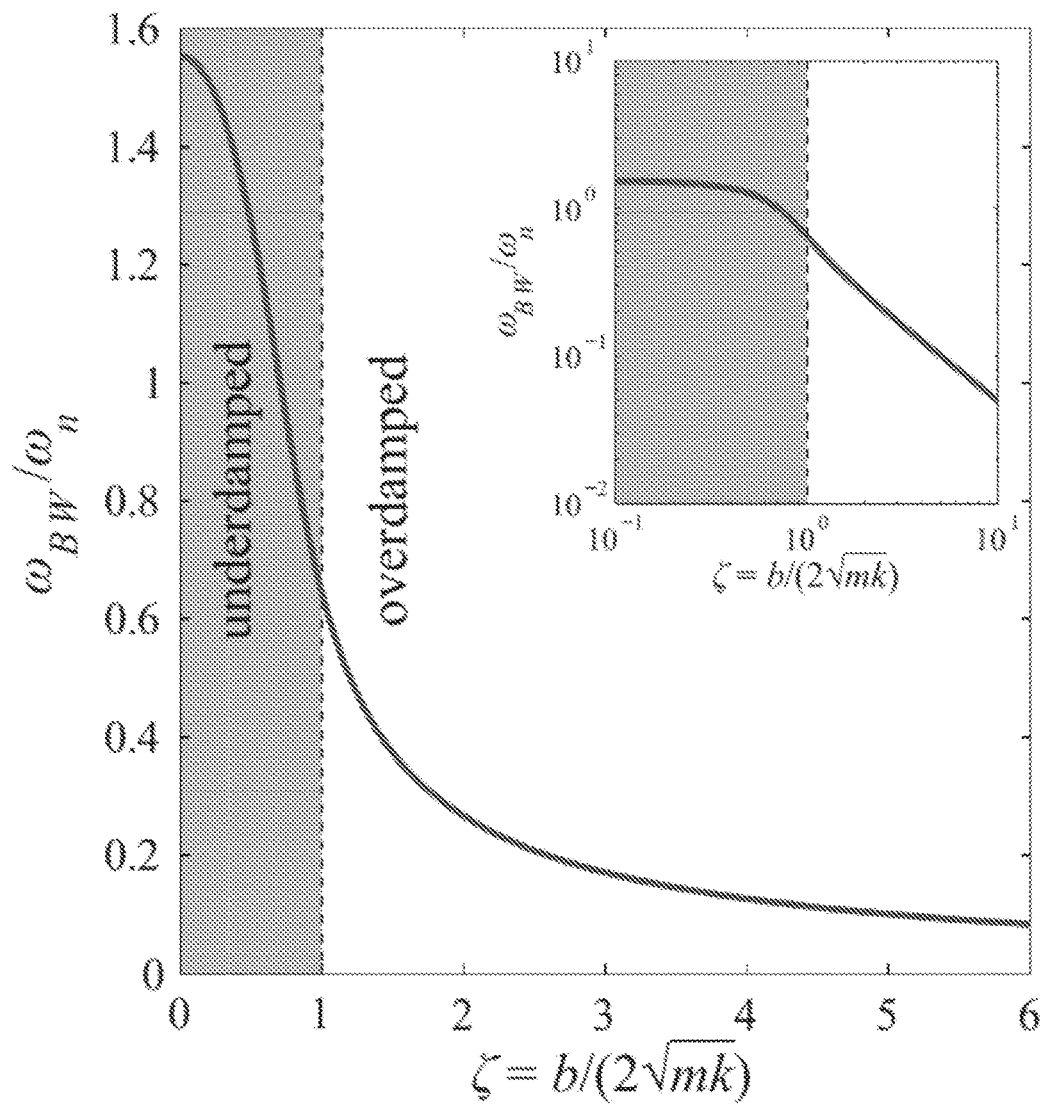
FIGS. 36A and 36B. Linear dynamics of an oscillator in a viscous medium.
Figure 36B:
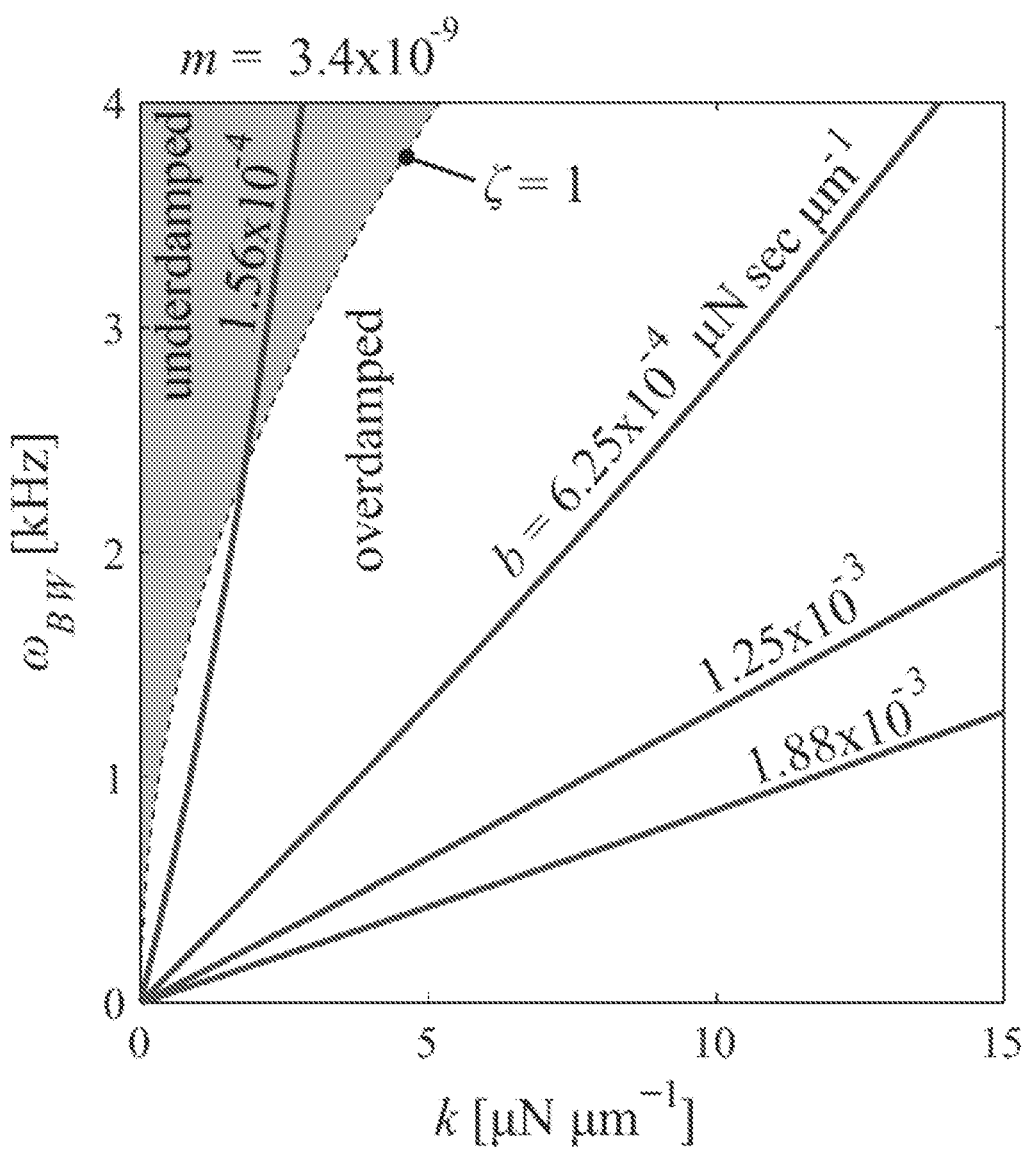

A sprung mass in a viscous medium with a single degree-of-freedom is simply modeled as a linear mass-spring-damper system (FIG. 35) with the equation of motion:

$$m\ddot{x}(t)+b\dot{x}(t)+kx(t)=F(x,t) \quad (2)$$

m is the oscillator mass assumed as a point-mass, b is the viscous damping parameter, k is the spring constant, x(t) is the generalized coordinate, and F(x,t) is an exogenous force applied to the point mass body in the direction of the generalized coordinate x. If we assume F(x,t) is purely a harmonic function in time, F(x,t)=½A(1+cos ωt), the steady-state solution to Eqn. (2) is also harmonic:

$$x(t) = \frac{1}{2}A\left(1/k + \frac{1/k}{\sqrt{\left(1-\frac{\omega^2}{\omega_n^2}\right)^2 + \left(2\zeta\frac{\omega}{\omega_n}\right)^2}}\cos(\omega t + \phi(\omega/\omega_n))\right) \quad (3)$$

where $$\omega_n = \sqrt{\frac{k}{m}}$$

and $\zeta=b/(2\sqrt{mk})$ are the natural frequency and damping coefficient, respectively, of a second-order underdamped oscillator, and $$\Phi\left(\frac{\omega}{\omega_n}\right)$$

is a frequency-dependent phase shift. Microresonators in air or vacuum are typically characterized by their $\omega_n$ and Q-factor. However, for large displacement, underwater oscillators, it is instructive to report bandwidth, $\omega_{BW}$, to characterize the achievable span of frequencies. Bandwidth is defined as the frequency at which the output signal has half the energy of the output signal when driven with a DC signal. Bandwidth can be expressed as a dimensionless parameter $\omega_{BW}/\omega_n$ which is a function of dimensionless $\zeta$:

$$\frac{\omega_{BW}}{\omega_n} = \sqrt{1 - 2\zeta^2 + \sqrt{4\zeta^4 - 4\zeta^2 + 2}} \quad (4)$$

where the oscillator is overdamped for $\zeta > 1$ (or $b > \sqrt{mk}$). The normalized bandwidth has an approximately asymptotic relationship with the damping coefficient (FIG. 36B), with bandwidth halving with a doubling in damping coefficient for $\zeta > 0.5$. Oscillator damping arises from squeeze film damping between the combed fingers [1] and drag losses between the sliding oscillator and static walls [2] [3]. Damping is detrimental to oscillator bandwidth and oscillator surface area should be minimized, as a general rule. However, a large displacement oscillator requires sufficient structural support at the combed fingers and probe base and a large suspending spring; hence, an underdamped response has not been demonstrated in an underwater oscillator with a displacement larger than 4 μm [4]. [5].

While the mass and damping coefficient values have a lower threshold as dictated by the structural robustness requirements, the spring constant is readily modulable through spring geometry design, spanning 3 orders of magnitude in reported oscillators [6], [7]. Bandwidth is approximately linearly proportional to spring constant for overdamped designs (FIG. 36B); the constitutive relationship:

$$\omega_{BW} \sim \frac{b - \sqrt{b^2 - 4mk}}{2m}; \text{ for } b > 2\sqrt{mk} \quad (5)$$

has a dominant linear term in the Taylor series expansion around k=0. Taken together, increasing k increases $\omega_{BW}$; however, at the expense of a larger requisite force to achieve the same displacement.

2) Nonlinear Static Model

The force F(x,t) is generated by a comb drive array. Two comb drive orientations are common in the literature, transverse and longitudinal, where a transverse drive corresponds to θ=90° and a longitudinal drive corresponds to θ=0° in FIG. 35. Transverse drives achieve higher forces than longitudinal drives for a similarly sized comb array, but have a displacement limited to ⅓ the comb gap ($x_1$ in FIG. 35) before the well-known 'pull-in' instability occurs [8], [9]. Longitudinal drives are not displacement limited, in theory, but achieve lower forces comparatively. A hybrid design achieves higher forces than a longitudinal drive and higher displacements than a transverse drive θ∈(0°, 90°) in FIG. 35). These characteristics yield a drive that generates large forces and displacements in a compact footprint, hence smaller surface area. Drive force is a function of variable drive displacement, x(t), and voltage, V(t), and constant geometric and physical parameters.

$$F(x(t), V(t)) = F_{\parallel}\cos\theta + F_{\perp}\sin\theta \quad (6)$$

$$F(x(t), V(t)) = \left(\left(\frac{1}{x_1 - x\sin\theta} + \frac{1}{x_2 + x\sin\theta}\right)\cos\theta + \frac{1}{2}\frac{(L_0 + x\cos\theta)(x_1 + x_2)(x_2 - x_1 + 2x\sin\theta)}{(x_1 - x\sin\theta)^2(x_2 + x\sin\theta)^2}\sin\theta\right)k\epsilon hNV^2$$

where F ∥ is the force parallel to the face of the combs [6] and F ⊥ is the force perpendicular to the face of the combs [8]. θ, $L_o$, $x_1$, and $x_2$, are geometric parameters (FIG. 35), h is the comb height, N is the number of comb pairs, κ is the dielectric constant of the comb gap medium (1 for air, 78 for deionized (DI) water), and $\in = 8.854 \times 10^{-12}$ $s^4A^2m^{-3}kg^{-1}$ is the permittivity of free space; Eqn. (6) is derived in the Appendix.

Figure 37A:
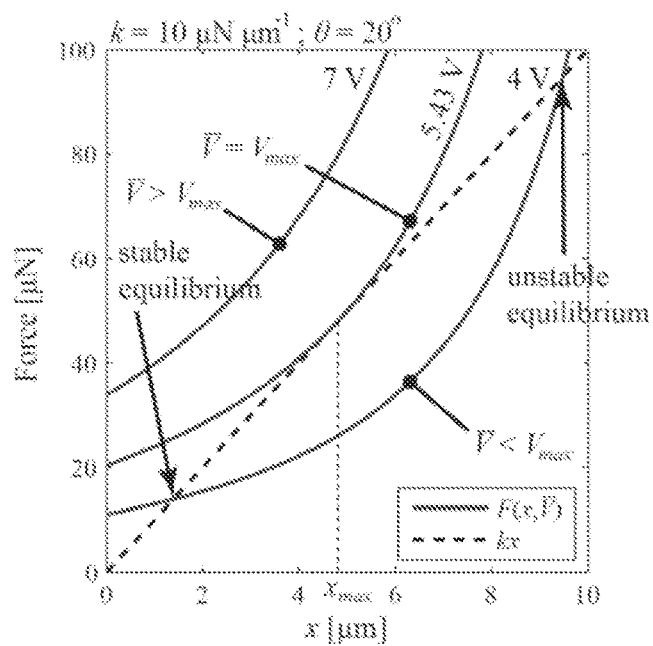
FIGS. 37A and 37B illustrate nonlinear static force optimization for displacement maximization.

Static oscillator displacement as a function of applied voltage is calculated by solving the nonlinear equation in Eqn. 6 for x. For a static $V(t) = \overline{V}$ such that:

$$F(x, \overline{V}) = kx \quad (7)$$

yields a solution, there is always on stable and one unstable solution (FIG. 37A). As $\overline{V}$ is increased to $\overline{V}_{max}$ the stable and unstable solutions converge to a double-root, $x_{max}$, which is the maximum stable displacement of the oscillator design.

Figure 37B:
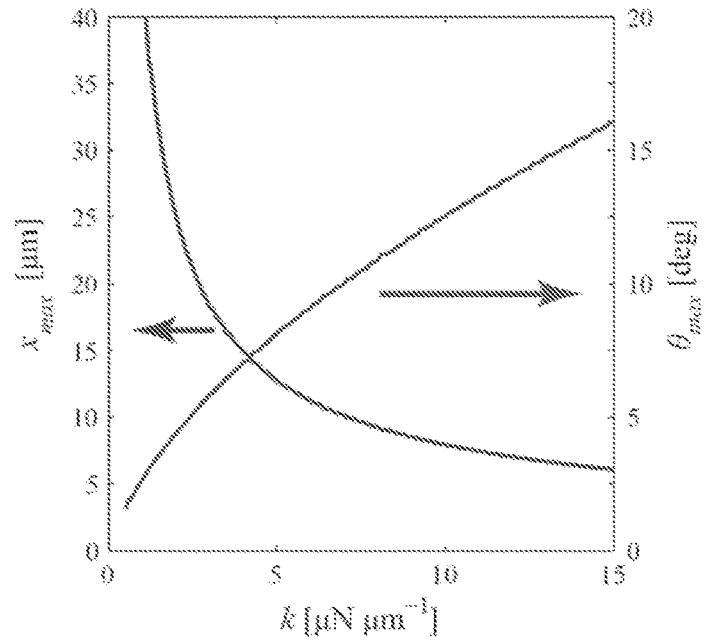

The solution to Eqn. (7) can be numerically solved across a design space to maximize displacement $x_{max}$. The design space is the range of all geometric parameters in FIG. 35, however we restrict the search to be the two most important parameters that influence displacement, k and θ. Underwater oscillators are force limited in that water in-between the charged combs will electrolyze if the electric field is too strong [6]; voltage is limited to 8 V. This design space presents the constrained optimization problem:

for $k \in (0, 30)$ find θ such that x is maximized subject to $\overline{V} \in [0, 8]$ $\theta_{max} = \theta$ $x_{max} = x$ end The optimal comb angle $\theta_{max}$ for every spring constant k lies along a monotonically increasing line (FIG. 37B). As k increases, the electrostatic force must be larger to counteract the spring force and therefore the optimal $\theta_{max}$ increases to generate a larger force with a $\overline{V}$ constrained by electrolysis bounds. At low k it is advantageous to have a more longitudinal design as this yields a larger displacement before the pull-in instability occurs.

B) Nonlinear Dynamic Model

1) Differential Equation Setup

The linear dynamic and nonlinear static analyses in Section II-A have conflicting design recommendations for underwater oscillators. A higher spring constant yields a higher bandwidth, but results in smaller displacement. The trade-off is exasperated by the $\overline{V} \in [0V, 8V]$ constraint that limits the generable force from small θ designs.

Additional design insights are realized by analyzing the full non-linear ordinary differential equation, (1) and (5), with $F(x, t)=F(X, V(t))$ and the voltage is harmonic, $V(t)=\frac{1}{2}\overline{V}(1+\cos \omega t)$. Electrostatic force is proportional to $V^2(t)$;

$$F(x, t) \propto \overline{V}\left(\frac{3}{8} + \frac{1}{2}\cos\omega t + \frac{1}{8}\cos 2\omega t\right).$$

The DC term of the driving voltage, $$\frac{3}{8}\overline{V},$$

imparts a DC offset in the position, $\hat{x}$, that can be solved by numerical methods. By a change of coordinates, x is rewritten as a deviation from the offset position, $x(t)=\overline{x}+\hat{x}(t)$, and Eqn. (1) is expanded as a Taylor series to the third-order, evaluated at $\overline{x}$.

$$m\ddot{\hat{x}} + b\dot{\hat{x}} + k(\hat{x}+\overline{x}) = \quad (8)$$

$$F(\overline{x}, V) + \frac{\partial F(\overline{x}, V)}{\partial x}\hat{x} + \frac{1}{2}\frac{\partial^2 F(\overline{x}, V)}{\partial x^2}\hat{x}^2 + \frac{1}{6}\frac{\partial^3 F(\overline{x}, V)}{\partial x^3}\hat{x}^3$$

Eqn. (7) is simplified by normalizing time by the driving frequency, $\tau=\omega t$, and pulling $$V(\tau)^2 = \overline{V}^2\left(\frac{3}{8} + \frac{1}{2}\cos\tau + \frac{1}{8}\cos 2\tau\right)$$

out of the coefficient terms. This yields the nonlinear, parameter-varying, inhomogeneous, ordinary differential equation:

$$\ddot{\hat{x}}+Q^{-1}\dot{\hat{x}}+(a_{10}+a_{11}\cos\tau+a_{12}\cos 2\tau)\hat{x}+(a_{20}+a_{21}\cos\tau+a_{22}\cos 2\tau)\hat{x}^2+(a_{30}+a_{31}\cos\tau+a_{32}\cos 2\tau)\hat{x}^3 = a_{01}\cos\tau+a_{02}\cos 2\tau \quad (9)$$

where the coefficient on $\ddot{\hat{x}}$ is divided through and the generic coefficients $\alpha_{(\cdot)}$ are constant parameters. All coefficients on the $\hat{x}$, $\hat{x}^2$, and $\hat{x}^3$ terms, except for $\alpha_{10}$, are less than 0. Therefore, the electrostatic forces act as a weakening spring. As the moving comb approaches the stationary spring the force returning the oscillator to the neutral position weakens.

Figure 38:
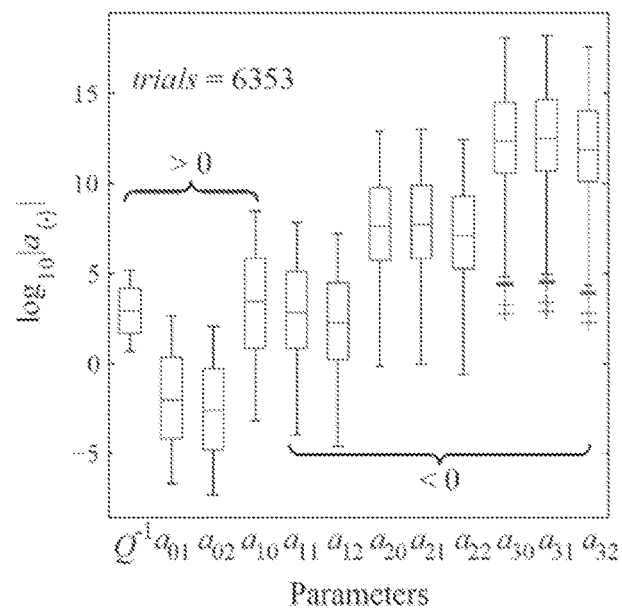
FIG. 38 illustrates parameter size ranges for Eqn. (9) for all candidate designs simulated.

The standard solution assumes that $Q^{-1}\ll 1$ and most of the $\alpha_{(\cdot)}\ll 1$ and solves (9) by perturbation methods [10]. Oscillators operated in air or vacuum typically have $Q\sim O(10^4\text{-}10^5)$ and the standard solution is valid [11], [12]. However, in an underwater operation scenario, viscous damping is approximately 6 orders of magnitude larger and, furthermore, all coefficients have non-negligible magnitudes (see, FIG. 38). Eqn. (9) is extremely stiff as the parameters and the states evolve on different time scales and therefore implicit and explicit solvers are too slow (~5 hr solution time) to be effectively leveraged in an optimization algorithm such as (II-A-2).

2) Fourier Series Solution

The differential equation (9) is a specific form of the Duffing equation[10] that is both parametrically driven and exogenously driven by harmonic functions. The basic Duffing equation has no known analytic solution [11], [12] and accordingly the solution to (9) requires a computational solution. Within the stable displacement limit the solution to (9) is also harmonic and can be solved by assuming a harmonic solution and solving for unknown coefficients [13]-[15].

$$x(t)=A_0+A_1\cos\tau+B_1\sin\tau+A_2\cos 2\tau+B_2\sin 2\tau+\ldots A_N\cos N\tau+B_N\sin N_\tau \quad (10)$$

The assumed solution is equivalently stated as vector algebra, $x(\tau)=T(\tau)X$, where:

$$T(\tau)=[1, \cos\tau, \sin\tau, \cos 2\tau, \sin 2\tau \ldots, \cos N\tau, \sin N\tau]$$

$$X=[A_0,A_1,B_1,A_2,B_2,\ldots,A_N,B_N]^T \quad (11)$$

$X\in\mathbb{R}^{2N+1\times 1}$ is a vector of unknown coefficients and $T(\tau)\in\mathbb{R}^{1\times 2N+1}$ is an orthogonal harmonic basis vector. The orthogonal basis is leveraged to rewrite (9) as matrix algebra:

$$T(\tau)\Delta^2 X+Q^{-1}T(\tau)\Delta X+T(\tau)(a_{10}+\alpha_{11}C_1+a_{12}C_2)X+T(\tau)(a_{20}+a_{21}C_1+a_{22}C_2)\Gamma(X)X+T(\tau)(a_{30}+a_{31}C_1+a_{32}C_2)\Gamma^2(X)X-T(\tau)G=0 \quad (12)$$

where $\Delta$ is the constant matrix that performs the operation $d/d\tau$, $C_1$ and $C_2$ are constant matrices that multiply $T(\tau)X$ by $\cos\tau$ and $\cos 2\tau$, respectively, $\Gamma(X)$ is a matrix of unknowns that performs the operation $x^2(\tau)\approx T(\tau)\Gamma(X)X$, and $G=[0, \alpha_{01}, \alpha_{02}, 0, \ldots]$. Matrix structures are detailed in the Appendix to Example 1. Eqn. (12) is simplified to the nonlinear matrix equation:

$$L(X)-F(X)-G=0 \quad (13)$$

The solution vector X is solved by the Newton-Raphson method:

$$X_{n+1} = X_n - \left(L+\frac{\partial F}{\partial X}(X_n)\right)^{-1}(LX_n+F(X_n)-G) \quad (14)$$

where n is the iteration index of the algorithm.

Given a stable operating voltage, (14) converges to a solution vector X in less than ten iterations, requiring approximately 30 seconds of computation time on a standard multi-core computer. Unstable operating voltages do not converge to a solution or converge to an infeasible solution outside the physical range of the oscillator.

Figure 39A:
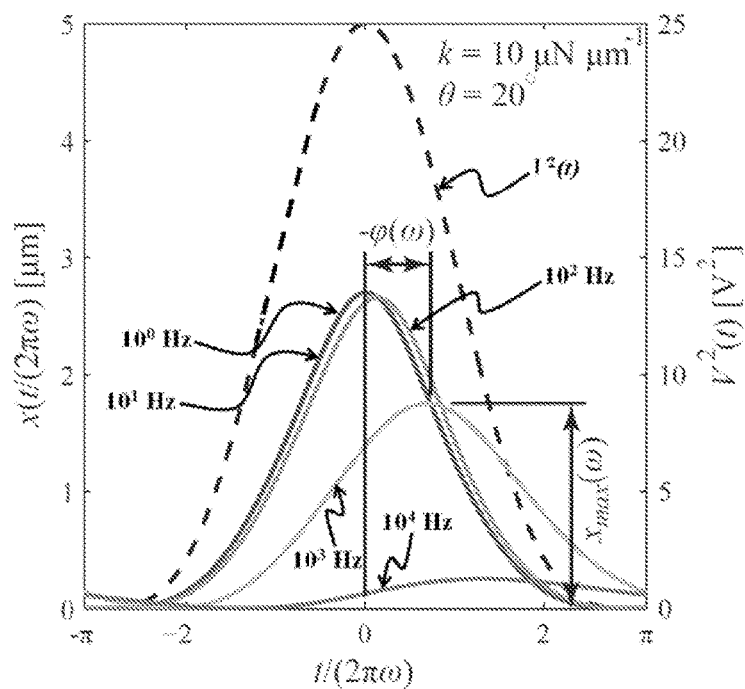
FIGS. 39A-39C illustrate a Fourier series solution to the equations of motion for an underwater oscillator (9).
Figure 39B:
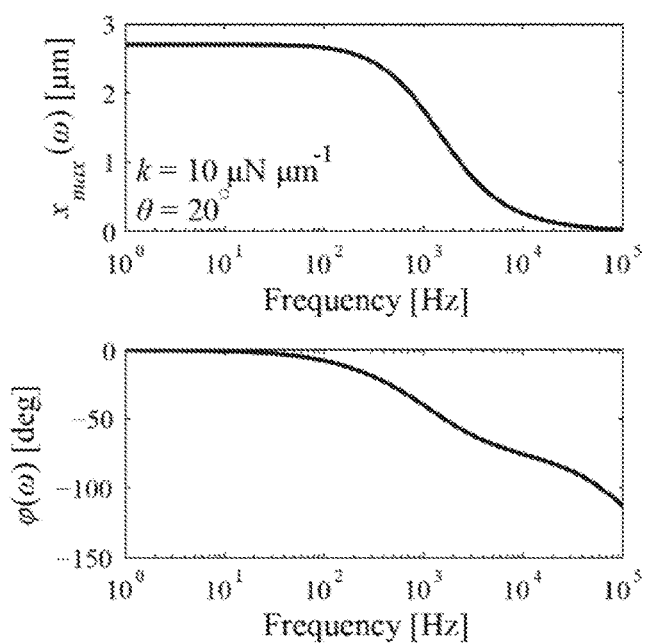
Figure 39C:
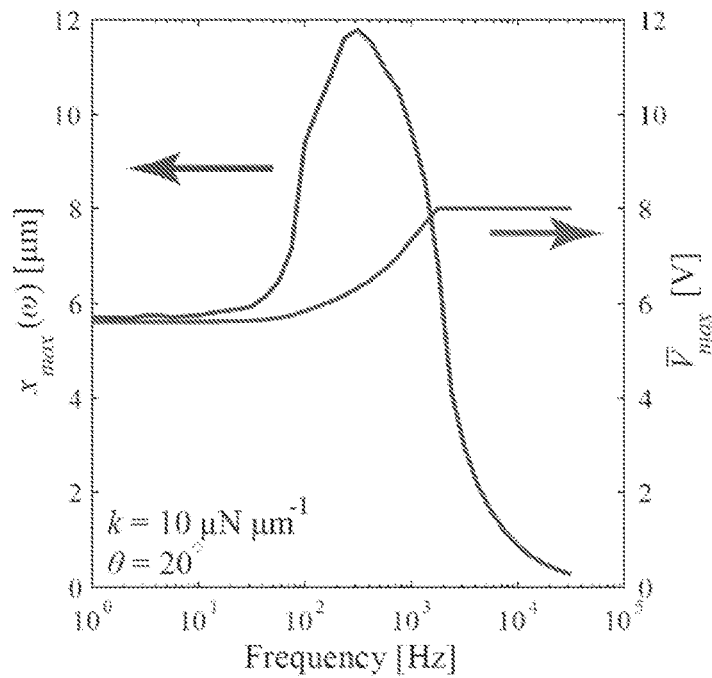

In the stable operating range, the underwater oscillator behaves as a second-order over-damped oscillator (FIG. 39A). For a set $\overline{V}=6V$ and oscillator design, $k=10$ μN μm$^{-1}$ and $\theta=20°$, the magnitude of response remains constant until approximately 500 Hz, whereafter the magnitude decreases with increasing frequency (FIG. 39A-39B). Accordingly, the phase shift increases with increasing frequency; importantly the phase shift at high frequencies enables an oscillator with a high stiffness spring to have a higher $x_{max}$ at high frequencies than at low frequencies. The parametrically driven terms (cost and cos 2τ terms on the left-hand side of (8)) are shifted out of phase with the inhomogenous driving terms and a higher voltage can be applied to the comb drive without introducing pull-in instabilities (FIG. 39C).

3) Dynamic Optimization.

In contrast to explicit and implicit solvers, the Fourier Series solution enables efficient optimization of the design variables k and θ to maximize displacement and achievable frequency range. The higher-level algorithm (15) solves the differential equation (8) 500-2000 times to optimize the parameter space. Optimized parameters are determined in less than one day.

for $k \in (0,15)$ and $\omega \in (2^{-1}, 2^{12})a$ find $\theta$ such that $x$ is maximized subject to $\overline{V} \in [0,8]$ $\theta_{max} = \theta$ $x_{max} = x$ end (15)

Figure 40A:
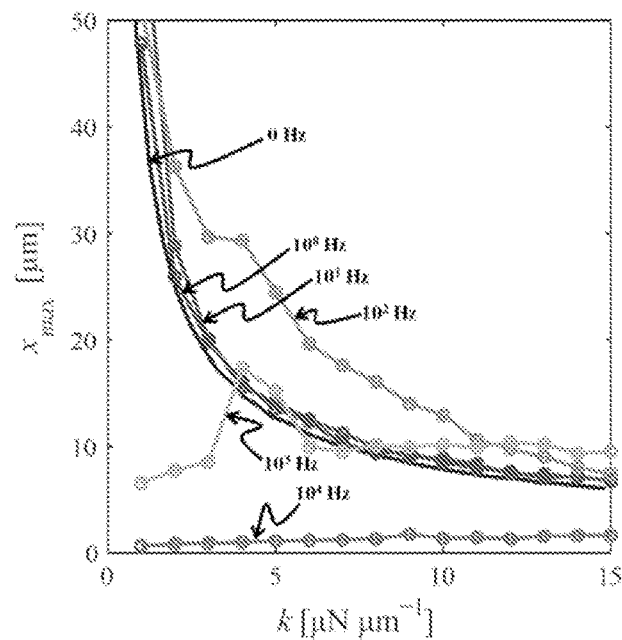
FIGS. 40A and 40B illustrate optimization of design parameters k and θ for a displacement larger than 5 μm at a frequency greater than 1 kHz.
Figure 40B:
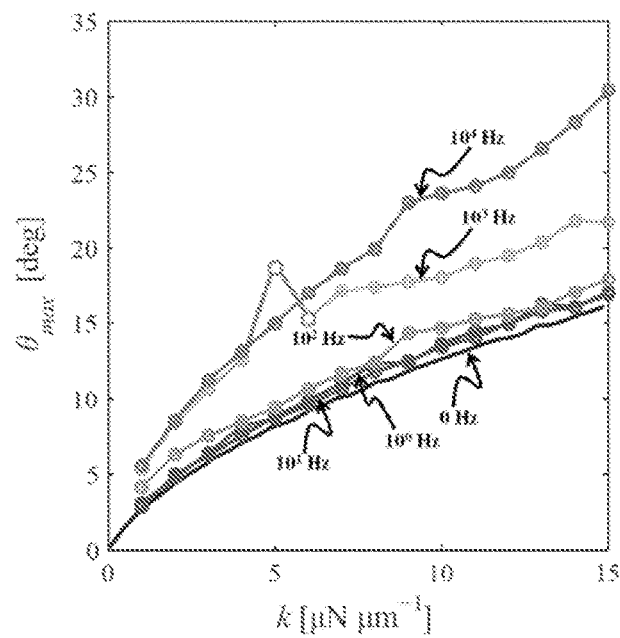

The static optimization demonstrated in FIG. 37B is elucidated with the additional dynamic optimization realized by the algorithm (15) (FIGS. 40A and 40B). At low-frequencies the maximum displacement $x_{max}$ and optimal drive angle $\theta$ are approximately the same as the static nonlinear case. At higher-frequencies, the behavior deviates from the static case; a higher spring stiffness and larger $\theta$ permit high-displacement, high-frequency actuation.

The spring constant k and drive angle $\theta$ are set by the design, while the voltage magnitude $\overline{V}$ is modulable. Given a displacement and actuation frequency objective, FIGS. 40A and 40B provide a map for k and 8 selection. For a general high-frequency underwater manipulation application we imposed a design objective of an $x_{max} > 8$ μm at a frequency greater than 1 kHz. Furthermore, the probe tip on the oscillator will be interacting with passaging particles in a fluid cross-stream and therefore must be robust to particle-tip interactions and stochasticity in flow. Accordingly, we chose an oscillator design with a stiff spring (k=10 μN μm$^{-1}$) to be insensitive to these perturbations and a drive angle ($\theta$=20°) that is optimized for actuation above 1 kHz.

Discussion.

This silicon-based electrostatic actuator achieves higher frequency actuation than polymeric actuators precisely because silicon has a Young's modulus to density ratio that is over three orders of magnitude larger than polydimethylsiloxane (PDMS), the standard material for polymeric, pressure-driven values. As the natural frequency of an oscillator is $$\omega_n = \sqrt{\frac{k}{m}}$$

where k is the spring constant and m is the oscillator mass, we accordingly achieve actuator frequencies that are 1.5 orders of magnitude larger than polymeric actuators. We envision tremendous utility in high-frequency valving and actuators for particle and cell manipulation, measurement of cell mechanical properties at high-throughputs, underwater in situ acoustic generators, and high switching frequency optical modulators for underwater optics.

APPENDIX TO EXAMPLE 3

A) Matrix Forms
1) Matrix Constructions:

$$\Delta = \begin{bmatrix} 0 & 0 & 0 & 0 & 0 & \ldots & 0 & 0 \\ 0 & 0 & 1 & 0 & 0 & \ldots & 0 & 0 \\ 0 & -1 & 0 & 0 & 0 & \ldots & 0 & 0 \\ 0 & 0 & 0 & 0 & 2 & \ldots & 0 & 0 \\ 0 & 0 & 0 & -2 & 0 & \ldots & 0 & 0 \\ \vdots & \vdots & \vdots & \vdots & \vdots & \ddots & \vdots & \vdots \\ 0 & 0 & 0 & 0 & 0 & \ldots & 0 & N \\ 0 & 0 & 0 & 0 & 0 & \ldots & -N & 0 \end{bmatrix} \quad (16)$$

$$C_1 = \begin{bmatrix} 0 & \frac{1}{2} & 0 & 0 & 0 & \ldots & 0 & 0 & 0 \\ 1 & 0 & 0 & \frac{1}{2} & 0 & \ldots & 0 & 0 & 0 \\ 0 & 0 & 0 & 0 & \frac{1}{2} & \ldots & 0 & 0 & 0 \\ 0 & \frac{1}{2} & 0 & 0 & 0 & \ldots & 0 & 0 & 0 \\ 0 & 0 & \frac{1}{2} & 0 & 0 & \ldots & 0 & 0 & 0 \\ \vdots & \vdots & \vdots & \vdots & \vdots & \ddots & \vdots & \vdots & \vdots \\ 0 & 0 & 0 & 0 & 0 & \ldots & 0 & 0 & \frac{1}{2} \\ 0 & 0 & 0 & 0 & 0 & \ldots & 0 & 0 & 0 \\ 0 & 0 & 0 & 0 & 0 & \ldots & \frac{1}{2} & 0 & 0 \end{bmatrix} \quad (17)$$

$$C2 = 2C_2^2 - I \quad (18)$$

2) Derivation of $\Gamma(X)$:

Given a vector of unknown harmonic magnitude components $X = [A_0, A_1, B_1, \ldots, A_N; B_N]$, $\Gamma(X)$ such that $x^2(\tau) \approx T(\tau)\tau(X)X$ is:

$$\Gamma(X) = FX^\dagger \quad (19)$$

F is a vector with entries that are nonlinear in terms of X.

$$F_0 = X_0^2 + \frac{1}{2}\sum_{i=1}^{2N} X_j^2 \quad (20)$$

$$F_j = \sum_{k=0}^{N} A_k A_{k+j} + \sum_{k=0}^{N} B_k B_{k+j} +$$

$$\frac{1}{2}\sum_{k=1}^{j-1} A_k A_{j-k} - \frac{1}{2}\sum_{k=1}^{j-1} B_k B_{j-k} \text{ for } j \text{ even}$$

$$F_j = \sum_{k=0}^{N} A_k B_{k+j} - \sum_{k=0}^{N} A_{k+j} B_k + \frac{1}{2}\sum_{k=1}^{j-1} A_k B_{j-k} +$$

$$\frac{1}{2}\sum_{k=1}^{j-1} B_{j-k} B_k \text{ for } j \text{ odd}$$

Each $X_j$ term in (20) must exist in the basis X. Terms exceeding this basis are truncated: $X_j=0$ for j>2N. Therefore that $x^2(\tau) \approx T(\tau)\Gamma(X)X$ is only an approximate solution.

B MEMS Fabrication

Silicon-on-glass micro-oscillators are fabricated by a multi-step lithographic process based on a procedure detailed in [16]. For the current design, we desired to image device motion with an inverted microscope, as per the standard for microfluidic device research. However, the fabrication workflow for designs not requiring a transparent substrate can be made more efficient by utilizing standard silicon-on-insulator wafers. The following section provides one illustrative MEMS fabrication procedure (FIG. 41).

Procedure:

1) Anodically bond (Karl-Suss SB6 Bonder) a low-resistance (0.005-0.020 Ω-cm) p-type silicon wafer with <1-0-0> orientation (Ultrasil, Hayward, Calif.) to a Pyrex 7740 glass wafer (Plan Optik, Elsoff, Germany).

2) Thin the Si side to 50 μm by lapping and polishing to the industry standard finish (RMS~1 nm; performed by Aptek Industries, San Jose, Calif.).

3) Deposit a Cr/Au film on the silicon surface by electron beam evaporation (CHA Solution; Fremont, Calif.; 8.5 nm Cr, 392 nm Au).

4) Pattern an etch mask by spin coating with photoresist (SPR700-1.2), exposing to UV, and developing to open the features to be etched. Note that devices are oriented such that the oscillator and sensor move parallel to the <1-0-0> plane.

5) Selectively etch Cr/Au film in a timed acid etch (TFA Gold Etchant (Transene, Danvers, Mass.) followed by CR-7S (Cyantek, Fremont, Calif.)).

6) Deposit a 750 nm $SiO_2$ film by PECVD (Plasma-therm 790, St. Petersburg, Fla.).

7) Fabricate device layer etch mask by photolithography and dry etching (Oxford 80+; Oxfordshire, United Kingdom).

8) DRIE silicon features through to the glass (Plasma-Therm SLR 770 ICP, St. Petersburg, Fla.).

9) Separate individual dies by wafer dicing.

10) Release moveable MEMS members from the glass layer by a timed HF wet etch of the glass layer (1:1 HF:$H_2O$, solution stirred at 100 rpm). This step also removes the remaining $SiO_2$ etch mask.

11) Dry MEMS devices by critical point drying (Tousimis 915B; Rockville, Md.).

REFERENCES FOR EXAMPLE 3

[1] M. Bao and H. Yang (2007) "Squeeze film air damping in MEMS," *Sensors and Actuators A*, 136: 3-27.

[2] C. Vančura, I. Dufour, S. M. Heinrich, F. Josse, and A. Hierlemann (2008) "Analysis of resonating microcantilevers operating in a viscous liquid environment," *Sensors and Actuators A*, 141: 43-51.

[3] Y.-B. Yi, A. Rahafrooz, and S. Pourkamali (2009) "Modeling and testing of the collective effects of thermoelastic and fluid damping on silicon MEMS resonators," *J. Micro/Nanolithography MEMS and MOEMS*, 8(2): 023010.

[4] N.-T. Nguyen, X. Huang, and T. K. Chuan (2002) "MEMS-micropumps: A review," *J. Fluids Engineering*, 124: 384-392.

[5] J. H. Seo and O. Brand (2008) "High Q-factor in-plane-mode resonant microsensor platform for gaseous/liquid environment," *J. Microelectromechanical Systems*, 17(2): 483-493.

[6] V. Mukundan and B. L. Pruitt (2009) "MEMS electrostatic actuation in conducting biological media," *J. Micromechanics Microengineering*, 18(2): 405-413.

[7] J. Tamayo, A. Humphris, A. Malloy, and M. Miles (2001) "Chemical sensors and biosensors in liquid environment based on microcantilevers with amplified quality factor," *Ultramicroscopy*, 86: 167-173.

[8] Y. Sun, D. Piyabongkarn, A. Sezen, B. Nelson, and R. Rajamani, (2002) "A high-aspect-ratio two-axis electrostatic microactuator with extended travel range," *Sensors and Actuators A*, 102: 49-60.

[9] A.-S. Rollier, B. Legrand, D. Collard, and L. Buchaillot (2006) "The stabilty and pull-in voltage of electrostatic parallel-plate actuators in liquid solutions," *J. Micromechanics and Microengineering*, 16: 794-801.

[10] R. Lifshitz and M. Cross (2008) Review of Nonlinear Dynamics and Complexity. Wiley.

[11] M. Agarwal, H. Mehta, R. N. Candler, S. Chandorkar, B. Kim, M. A. Hoperoft, R. Melamud, G. Bahl, G. Yama, T. W. Kenny, and B. Murmann (2007) "Scaling of amplitude-frequency-dependence nonlinearities in electrostatically transduced microresonators," *J. Appl. Physics*, 102: 074903.

[12] J. F. Rhoads, S. W. Shaw, and K. L. Turner (2010 "Nonlinear dynamics and its applications to micro- and nanoresonators," *J. Dynamic Systems, Measurement, and Control*, 132: 034001.

[13] L. K. Forbes (1987) "Periodic solutions of high accuracy to the forced Duffing equation: Perturbation series in the forcing amplitude," *J. Australian Mathematical Society. Series B.*, 29(1): 21-38.

[14] V. Méndez, D. Sans, Cristina an Campos, and I. Llopis (2010) "Fourier series expansion for nonlinear hamiltonian oscillators," *Physical Review E*, 81: 006201.

[15] M. Guskov, J.-J. Sinou, and F. Thouverez 92006) "Duffing oscillator under multiharmonic excitation," in 2006 Conference and Exposition on Structural Dynamics.

[16] J. Chae, H. Kulah, and K. Najafi (2005) "A CMOS-compatible high aspect ratio silicon-on-glass in-plane micro-accelerometer," *J. Micromechanics and Microengineering*, 15: 336-345.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of measuring the elastic modulus or stiffness of a cell, said method comprising:
   providing a device comprising:
      a microfluidic channel comprising a first side wall and a second side wall where a fluid flows through said microfluidic channel between said first side wall and said second side wall:
      an oscillating element on the first side wall of said channel, where said oscillating element comprises a comb drive; and
      a detecting element on the second side wall of said channel where said detecting element comprises a comb, and where said detecting element is directly across said channel from said oscillating element and said oscillating element and said detecting element define a probe interface;
   passing said cell in said fluid through said microfluidic channel so that said cell is passes through said probe interface and is in contact with said oscillating element and said detecting element;
   operating said oscillating element to apply a force to said cell inside said microfluidic channel; and
   operating said detecting element to detect said force transmitted through said cell by determining displacement of comb fingers comprising said comb by detecting capacitance changes produced by said comb in response to said displacement of comb fingers, wherein said displacement provides a measure of the elastic modulus or stiffness of said cell.

2. The method of claim 1, wherein said device is operated with a fundamental frequency of 400 Hz and a carrier frequency of 0.5 MHz.

3. The method of claim 1, wherein said oscillating element oscillates at a frequency ranging from 60 Hz up to 4 kHz.

4. The method of claim 1, wherein the width of said microfluidic channel is sufficient to pass a single cell.

5. The method of claim 1, wherein the width of said microfluidic channel ranges from 1 μm to 300 μm.

6. The method of claim 1, wherein said device comprises a cell-centering microfluidic structure.

7. The method of claim 6, wherein said cell-centering microfluidic structure comprises said microfluidic channel in fluid communication with a plurality of lateral channels.

8. The method of claim 1, wherein said oscillating element is configured to oscillate in response to a varying potential.

9. The method of claim 1, wherein the comb drive comprising said oscillating element further comprises beam springs that return comb fingers to a neutral position.

10. The method of claim 1, wherein said device comprises a second channel or fluid line that carries deionized or distilled water across the oscillating or detecting elements.

11. The method of claim 1, wherein said device comprises a second channel or fluid line that carries a fluid with a lower dielectric constant than said first fluid in the microfluidic channel.

12. The method of claim 1, wherein said device comprises a fabricated block within which is formed, embedded or molded said microfluidic channel.

13. The method of claim 12, wherein the block material from which the device is fabricated is selected from the group consisting of polydimethylsiloxane (PDMS), polyolefin plastomer (POP), perfluoropolyethylene (PFPE), polyurethane, polyimides, and cross-linked phenol formaldehyde polymer resins, borosilicate glass, SF11 glass, SF12 glass, polystyrene, PMMA, and polycarbonate.

14. The method of claim 1, wherein said device comprises a pump or pressure system to move cells through or into said first microfluidic channel.

15. The method of claim 1, wherein the comb comprising said detecting element further comprise beam springs that return comb fingers to a neutral position.

* * * * *